United States Patent
Sircar et al.

(10) Patent No.: US 7,282,518 B2
(45) Date of Patent: *Oct. 16, 2007

(54) BENZIMIDAZOLE COMPOUNDS FOR MODULATING IGE AND INHIBITING CELLULAR PROLIFERATION

(75) Inventors: Jagadish C. Sircar, San Diego, CA (US); Mark L. Richards, San Diego, CA (US)

(73) Assignee: Avanir Pharmaceuticals, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/795,006

(22) Filed: Mar. 5, 2004

(65) Prior Publication Data

US 2004/0214821 A1 Oct. 28, 2004

Related U.S. Application Data

(62) Division of application No. 10/090,044, filed on Feb. 27, 2002, now Pat. No. 6,759,425.

(60) Provisional application No. 60/275,260, filed on Mar. 12, 2001.

(51) Int. Cl.
*A61K 31/4402* (2006.01)
*A61K 31/4427* (2006.01)
*A61K 31/4439* (2006.01)
*C07D 401/12* (2006.01)
*C07D 403/12* (2006.01)

(52) U.S. Cl. .................................. 514/444; 546/268.1
(58) Field of Classification Search ................ 514/444; 546/268.1
See application file for complete search history.

(56) References Cited

U.S. PATENT DOCUMENTS

| | | | |
|---|---|---|---|
| 4,510,158 A | 4/1985 | Bailey | |
| 4,582,837 A | 4/1986 | Hauel et al. | |
| 4,696,931 A | 9/1987 | Hauel et al. | |
| 5,017,467 A | 5/1991 | Masukawa et al. | |
| 5,124,336 A | 6/1992 | Bru-Magniez et al. | |
| 5,322,847 A | 6/1994 | Marfat et al. | |
| 5,380,865 A | 1/1995 | Cramp et al. | |
| 5,643,893 A | 7/1997 | Benson et al. | |
| 5,712,392 A | 1/1998 | Thurkauf et al. | |
| 5,821,258 A * | 10/1998 | Matsunaga et al. ......... 514/394 |
| 5,935,983 A | 8/1999 | Muller-Gliemann et al. | |
| 6,093,728 A | 7/2000 | McMahon et al. | |
| 6,100,282 A | 8/2000 | Alig et al. | |
| 6,100,283 A | 8/2000 | Griffin et al. | |
| 6,153,631 A | 11/2000 | Petrie et al. | |
| 6,271,249 B1 | 8/2001 | Romine et al. | |
| 6,271,390 B1 | 8/2001 | Sircar et al. | |
| 6,288,101 B1 | 9/2001 | Glennon | |
| 6,303,645 B1 | 10/2001 | Sircar et al. | |
| 6,369,091 B1 | 4/2002 | Sircar et al. | |
| 6,387,938 B1 | 5/2002 | Mizuguchi et al. | |
| 6,451,829 B2 | 9/2002 | Sircar et al. | |
| 6,486,153 B1 | 11/2002 | Castro Pineiro et al. | |
| 6,503,938 B1 | 1/2003 | Von Angerer et al. | |
| 6,509,365 B1 | 1/2003 | Lubisch et al. | |
| 6,537,994 B2 | 3/2003 | Ashwell et al. | |
| 6,759,425 B2 | 7/2004 | Sircar et al. | |
| 6,911,462 B2 | 6/2005 | Sircar et al. | |
| 6,919,366 B2 | 7/2005 | Sircar et al. | |
| 2002/0010343 A1 | 1/2002 | Sircar et al. | |
| 2002/0132808 A1 | 9/2002 | Sircar et al. | |
| 2003/0004203 A1 | 1/2003 | Sircar et al. | |
| 2003/0100582 A1 | 5/2003 | Sircar et al. | |
| 2004/0116466 A1 | 6/2004 | Sircar et al. | |
| 2004/0180946 A1 | 9/2004 | Sircar et al. | |
| 2004/0229927 A1 | 11/2004 | Sircar et al. | |
| 2005/0075343 A1 | 4/2005 | Sircar et al. | |
| 2005/0197375 A1 | 9/2005 | Sircar et al. | |
| 2005/0256179 A1 | 11/2005 | Sircar et al. | |
| 2005/0277686 A1 | 12/2005 | Sircar et al. | |

FOREIGN PATENT DOCUMENTS

| | | |
|---|---|---|
| EP | 0 221 146 A1 | 5/1987 |
| EP | 0 221 346 A1 | 5/1987 |
| EP | 0 232 199 A2 | 8/1987 |
| EP | 0 353 606 A2 | 2/1990 |
| EP | 0 415 886 A2 | 8/1990 |
| EP | 0 385 850 A2 | 9/1990 |
| EP | 0 469 477 A1 | 2/1992 |
| EP | 0 497 564 A1 | 5/1992 |
| EP | 0694535 | 1/1996 |
| EP | 0 700 906 A1 | 3/1996 |
| EP | 719765 | 3/1996 |
| EP | 0 719 765 A2 | 7/1996 |
| EP | 0719 765 A2 | 7/1996 |
| EP | 1 077 700 | 2/2001 |
| EP | 1 123 295 | 8/2001 |
| EP | 1 125 936 A2 | 8/2001 |
| JP | 06 263993 A | 9/1994 |
| SU | 1316559 | 6/1983 |
| WO | WO90/09989 | 9/1990 |
| WO | WO92 02500 | 2/1992 |
| WO | WO93/25517 | 12/1993 |

(Continued)

OTHER PUBLICATIONS

Yildir et al. "Synthesis of 2-(Substitutedphenyl)Benzimidazole Derivatives and Their Sedative Activity: Structure-Activity Relationships". J. Fac. Pharm. Gazi, vol. 7, No. 2, 1990, pp. 111-124.

(Continued)

*Primary Examiner*—Rita Desai
(74) *Attorney, Agent, or Firm*—Knobbe Martens olson & Bear LLP

(57) ABSTRACT

The present invention is directed to small molecule inhibitors of the IgE response to allergens, which are useful in the treatment of allergy and/or asthma or any diseases where IgE is pathogenic. This invention also relates to benzimidazole molecules that are cellular proliferation inhibitors and thus are useful as anticancer agents.

16 Claims, 1 Drawing Sheet

FOREIGN PATENT DOCUMENTS

| WO | WO98/17267 | 4/1998 |
|---|---|---|
| WO | WO98/47890 | 10/1998 |
| WO | WO98/56761 | 12/1998 |
| WO | WO99 61020 | 2/1999 |
| WO | WO9961019 | 2/1999 |
| WO | WO8906975 | 8/1999 |
| WO | WO99 61013 A1 | 12/1999 |
| WO | WO99 61019 | 12/1999 |
| WO | WO99 61020 | 12/1999 |
| WO | WO 00/26192 | 5/2000 |
| WO | WO 00/29384 | 5/2000 |
| WO | WO 0026192 | 5/2000 |
| WO | WO 0029384 | 5/2000 |
| WO | WO 00/32579 | 6/2000 |
| WO | WO 00/64878 | 11/2000 |
| WO | WO 00/68206 | 11/2000 |
| WO | WO 01/12169 | 2/2001 |
| WO | WO 01/14342 | 3/2001 |
| WO | WO 01 14342 A1 | 3/2001 |
| WO | WO 01 72737 A1 | 10/2001 |
| WO | WO 02 72090 | 9/2002 |
| WO | WO 02/072539 | 9/2002 |
| WO | WO 02/072574 | 9/2002 |
| WO | WO 04 024896 | 3/2004 |

OTHER PUBLICATIONS

Related pending PCT Patent Application No. PCT/US03/05985, filed Feb. 25, 2003. Title: Use of Benzimidazole Analogs in the Treatment of Cell Proliferation. Inventors: Jagadish C. Sircar et al.

Related pending U.S. Appl. No. 10/661,139, filed Sep. 12, 2003. Title: Phenyl-Indole Compounds for Modulating IgE and Inhibiting Cellular Proliferation. Inventors: Jagadish C. Sircar et al.

Related pending U.S. Appl. No. 10/661,296, filed Sep. 12, 2003. Title: Phenyl-Aza-Benzimidazole Compounds for Modulating IgE and Inhibiting Cellular Proliferation. Inventors: Jagadish C. Sircar et al.

Ashton, Michael et al., "New Low-Density Lipoprotein Receptor Upregulators Acting via a Novel Mechanism", Journal of Medicinal Chemistry vol. 39, pp. 3343-3356, 1996.

Cheney, B. Vernon, "Structure-Activity Correlations for a Series of Antiallergy Agents. 3. Development of a Quantitative Model", Journal of Medicinal Chemistry vol. 26, pp. 726-737, 1983.

Karag'ozov, S., "Synthesis of N-acyl Derivatives of 6-amino-1-4-benzodioxane", Farmatsiya vol. 39, No. 2, pp. 5-8, 1989. (Bulgaria).

Pozdnyakov et al., "Mass Spectrometric Study of Dissociative Ionization of Low-Molecular Modules of Aromatice Polyamides", Khim. Vys. Energ., vol. 21, No. 1, pp. 38-44, 1987. (Russia).

Japanese Application No. 10273013 entitled, Antagonist for Gonadotrophic Hormone-Releasing Hormone, filed on Sep. 28, 1998, English abstract only.

Database Crossfire Beilstein 'Online!, Beilstein Institut zur Forderung der Chemischen Wissenchaften, Frankfurt am Main, DE; Beilstein Registry No. 563073 & Khim. Farm. ZH., vol. 22, No. 6, 1988, pp. 697-699.

Denny W A et al., "Potential antitumor agents. 59. Structure-activity relationships for 2-phenylbenzimidazole-4-carboxamides, a new class of "minimal" DNA-intercalating agents which may not act via topoisomerase II", Journal of Medicinal Chemistry, vol. 33, No. 2, Feb. 1990, pp. 814-819.

White A W et al., "Resistance-modifying agents. 9. Synthesis and biological properties of benzimidazole inhibitors of the DNA repair enzyme poly(ADP-ribose) polymerase", Journal of Medicinal Chemistry, vol. 43, No. 2, Nov. 2, 2000, pp. 4084-4097.

Database Caplus 'Online! Chemical Abstracts Service, Columbus, Ohio, US; Database accession No. 2000:214835 & JP 2000 095767 (Takeda Chemical Industries, Ltd.), Apr. 4, 2000.

Kreimeyer A et al., "Suramin analogues with a 2-phenylbenzimidazole moiety as partyial structure; potential anti HIV-and angiostic drugs, 2: Sulfanilic acid, benzendisulfonic, and naphthalenetrisulfonic acid analogues" Archi Der Pharmazie, vol. 331, No. 3, Mar. 1998, pp. 97-103.

Chilean Office Action with Search Report for the Chilean counterpart of the U.S. Appl. No. 10/795,006.

Related pending U.S. Appl. No. 10/821,667, filed Apr. 9, 2004. Title: Imidazole Derivatives for Treatment of Allergic and Hyperproliferative Disorders. Inventors: Jagadish C. Sircar et al.

Related pending U.S. Appl. No. 10/915,722, filed Aug. 9, 2004. Title: Selective Pharmacologic Inhibition of Protein Trafficking and Related Methods of Treating Human Diseases. Inventors: Jagadish C. Sircar et al.

Related pending U.S. Appl. No. 10/508,968, filed Sep. 24, 2004. Title: Use of Benzimidazole Analogs in the Treatment of Cell Proliferation. Inventors: Jagadish C. Sircar et al.

Related pending U.S. Appl. No. 10/951,515, filed Sep. 28, 2004. Title: Benzimidazole Derivatives as Modulators of IgE. Inventors: Jagadish C. Sircar et al.

Related pending U.S. Appl. No.11/168,711, filed Jun. 28, 2005. Title: Benzimidazole Compounds for Regulating IgE. Inventors: Jagadish C. Sircar et al.

Manecke et al., Über Polyamide mit 2,4-Imidazolidiyl-Bausteinen, Die Makromolekulare Chemie 176, pp. 3551-3563 (1975), Apr. 29, 1975, Institut für Organische Chemie der Freien Universität Berline, D-1 Berlin 33.

Cheney B V, et al., "Structure-activity Correlations for a Series of Antiallergy Agents. 3. Development of a Quantitative Model," Journal of Medicinal Chemistry, vol. 26, No. 5, 1983, pp. 726-737.

Pozdnyakov et al., "Mass Spectrometric Study of Dissociative Ionization of Low-molecular Models of Aromatic Polyamides," Khim. Vys. Energ. (1987), 21(1), 38-44 Coden; Khvkao; ISSN: 0023-1193, 1987.

English language abstract of Pozdnyakov, et al. (1987) "Mass spectrometric study of dissociative ionization of low-molecular models of aromatic polyamides," vol. 21 (1); pp. 38-44.

Database Crossifre Beilstein 'Online!, Beilstein Institut zur Forderung der Chemischen Wissenchaften, Frankfurt am Main, DE; Beilstein Registry No. 563073 & Khim. Farm. ZH., vol. 22, No. 6, 1988, pp. 697-699.

Karag'ozov S, "Synthesis of N-acyl Derivatives of 6-amino-1-4-benzodioXane," STN International, vol. 39, No. 1989 pp. 5-8, Abstract only.

Masukawa et al., Calplus 111:31259 (EP 304856, Mar. 1, 1989).

Denny W A et al., "Potential antitumor agents. 59. Structure-activity relationships for 2-phenylbenzimidazole-4-carboXamides, a new class of "minimal" DNA-intercalating agents which may not act via topoisomerase II", Journal of Medicinal Chemistry, vol. 33, No. 2, Feb. 1990, pp. 814-819.

Yildir I, "Synthesis of 32-(subtitutephenyl) Benzimidazole Derivatives and their Sedative Activity: Structure-activity Relationships," Journal FaX. Pharm. Gazi Uni., vol. 7, No. 2, 1990, pp. 111-114.

Timothy F. Gallagher, et al., "2,4,5-Triarylimidazole Inhibitors of IL-1 Biosynthesis," Bioorganic & Medicinal Chemistry Letters, vol. 5, No. 11, pp. 1171-1176, 1995.

Ashton et al., "New Low-Density Lipoprotein Receptor Upregulators Acting via a Novel Mechanism," Journal of Medicinal Chemistry, vol. 39, Jan. 1, 1996, pp. 3343-3356.

Krieg et al., ber einige neue Imidazolderivate, Chem. Ber. 100, pp. 4042-4049 (1967), Jun. 28, 1997, Jahrg. 100, Aus dem Institut für Organische Chemie der Freien Universität Berlin, Berlin-Dahlem.

Kreimeyer A et al., "Suramin analogues with a 2-phenylbenzimidazole moiety as partyial structure; potential anti HIV-and angiostic drugs, 2: Sulfanilic acid, benzendisulfonic, and naphthalenetrisulfonic acid analogues" Archi Der Pharmazie, vol. 331, No. 3, Mar. 1998, pp. 97-103.

Japanese Application No. 10273013, entitled Antagonist for Gonadotrophic Hormone-Releasing Hormone, filed on Sep. 28, 1998, English abstract only.

Database Caplus 'Online! Chemical Abstracts Service, Columbus, Ohio, US; Database accession No. 2000:214835 & JP 2000 095767 (Takeda Chemical Industries, Ltd.), Apr. 4, 2000.

White A W et al., "Resistance-modifying agents. 9. Synthesis and biological properties of benzimidazole inhibitors of the DNA repair enzyme poly(ADP-ribose) polymerase", Journal of Medicinal Chemistry, vol. 43, No. 2, Nov. 2, 2000, pp. 4084-4097.

Chemical structure database (CA, Caplus, Chemcats) search results for bis-5,4'-dibenzanilide-2-phenylbenzimidazole (Registry No. 98806-53-2).

* cited by examiner

BENZIMIDAZOLE COMPOUNDS FOR MODULATING IGE AND INHIBITING CELLULAR PROLIFERATION

RELATED APPLICATIONS

This application is a division of prior application Ser. No. 10/090,044, filed on Feb. 27, 2002, now U.S. Pat. No. 6,759,425 which claims priority under 35 U.S.C. §119(e) to U.S. Provisional Application No. 60/275,260, filed on Mar. 12, 2001, the prior application Ser. No. 10/090,044 is also a continuation-in-part of U.S. application Ser. No. 09/422,304, filed on Oct. 21, 1999, now U.S. Pat. No. 6,369,091.

BACKGROUND OF THE INVENTION

1. Field of the Invention

This invention relates to small molecule inhibitors of the IgE response to allergens that are useful in the treatment of allergy and/or asthma or any diseases where IgE is pathogenic. This invention also relates to small molecules that are proliferation inhibitors and thus they are useful as anticancer agents.

2. Description of the Related Art

Allergies and Asthma

An estimated 10 million persons in the United States have asthma, about 5% of the population. The estimated cost of asthma in the United States exceeds $6 billion. About 25% of patients with asthma who seek emergency care require hospitalization, and the largest single direct medical expenditure for asthma has been inpatient hospital services (emergency care), at a cost of greater than $1.6 billion. The cost for prescription medications, which increased 54% between 1985 and 1990, was close behind at $1.1 billion (Kelly, *Pharmacotherapy* 12:13S–21S (1997)).

According to the National Ambulatory Medical Care Survey, asthma accounts for 1% of all ambulatory care visits, and the disease continues to be a significant cause of missed school days in children. Despite improved understanding of the disease process and better drugs, asthma morbidity and mortality continue to rise in this country and worldwide (U.S. Department of Health and Human Services; 1991, publication no. 91-3042). Thus, asthma constitutes a significant public health problem.

The pathophysiologic processes that attend the onset of an asthmatic episode can be broken down into essentially two phases, both marked by bronchoconstriction, that causes wheezing, chest tightness, and dyspnea. The first, early phase asthmatic response is triggered by allergens, irritants, or exercise. Allergens cross-link immunoglobulin E (IgE) molecules bound to receptors on mast cells, causing them to release a number of pre-formed inflammatory mediators, including histamine. Additional triggers include the osmotic changes in airway tissues following exercise or the inhalation of cold, dry air. The second, late phase response that follows is characterized by infiltration of activated eosinophils and other inflammatory cells into airway tissues, epithelial desquamonon, and by the presence of highly viscous mucus within the airways. The damage caused by this inflammatory response leaves the airways "primed" or sensitized, such that smaller triggers are required to elicit subsequent asthma symptoms.

A number of drugs are available for the palliative treatment of asthma; however, their efficacies vary markedly. Short-acting $\beta_2$-adrenergic agonists, terbutaline and albuterol, long the mainstay of asthma treatment, act primarily during the early phase as bronchodilators. The newer long-acting $\beta_2$-agonists, salmeterol and formoterol, may reduce the bronchoconstrictive component of the late response. However, because the $\beta_2$-agonists do not possess significant antiinflammatory activity, they have no effect on bronchial hyperreactivity.

Numerous other drugs target specific aspects of the early or late asthmatic responses. For example, antihistamines, like loratadine, inhibit early histamine-mediated inflammatory responses. Some of the newer antihistamines, such as azelastine and ketotifen, may have both antiinflammatory and weak bronchodilatory effects, but they currently do not have any established efficacy in asthma treatment. Phosphodiesterase inhibitors, like theophylline/xanthines, may attenuate late inflammatory responses, but there is no evidence that these compounds decrease bronchial hyperreactivity. Anticholinergics, like ipratopium bromide, which are used in cases of acute asthma to inhibit severe bronchoconstriction, have no effect on early or late phase inflammation, no effect on bronchial hyperreactivity, and therefore, essentially no role in chronic therapy.

The corticosteroid drugs, like budesonide, are the most potent antiinflammatory agents. Inflammatory mediator release inhibitors, like cromolyn and nedocromil, act by stabilizing mast cells and thereby inhibiting the late phase inflammatory response to allergen. Thus, cromolyn and nedocromil, as well as the corticosteroids, all reduce bronchial hyperreactivity by minimizing the sensitizing effect of inflammatory damage to the airways. Unfortunately, these antiinflammatory agents do not produce bronchodilation.

Several new agents have been developed that inhibit specific aspects of asthmatic inflammation. For instance, leukotriene receptor antagonists (ICI-204, 219, accolate), specifically inhibit leukotriene-mediated actions. The leukotrienes have been implicated in the production of both airway inflammation and bronchoconstriction.

Thus, while numerous drugs are currently available for the treatment of asthma, these compounds are primarily palliative and/or have significant side effects. Consequently, new therapeutic approaches which target the underlying cause rather than the cascade of symptoms would be highly desirable. Asthma and allergy share a common dependence on IgE-mediated events. Indeed, it is known that excess IgE production is the underlying cause of allergies in general and allergic asthma in particular (Duplantier and Cheng, *Ann. Rep. Med. Chem.* 29:73–81 (1994)). Thus, compounds that lower IgE levels may be effective in treating the underlying cause of asthma and allergy.

None of the current therapies eliminate the excess circulating IgE. The hypothesis that lowering plasma IgE may reduce the allergic response, was confirmed by recent clinical results with chimeric anti-IgE antibody, CGP-51901, and recombinant humanized monoclonal antibody, rhuMAB-E25. Indeed, three companies, Tanox Biosystems, Inc., Genentech Inc. and Novartis AG are collaborating in the development of a humanized anti-IgE antibody (BioWorld® Today, Feb. 26, 1997, p. 2) which will treat allergy and asthma by neutralizing excess IgE. Tanox has already successfully tested the anti-IgE antibody, CGP-51901, which reduced the severity and duration of nasal symptoms of allergic rhinitis in a 155-patient Phase II trial (Scrip #2080, Nov. 24, 1995, p.26). Genentech recently disclosed positive results from a 536 patient phase-II/III trials of its recombinant humanized monoclonal antibody, rhuMAB-E25 (BioWorld® Today, Nov. 10, 1998, p. 1). The antibody, rhuMAB-E25, administered by injection (highest dose 300 mg every 2 to 4 weeks as needed) provided a 50% reduction in the number of days a patient required additional "rescue" medicines (antihistimines and decongestants), compared to placebo. More recently, Dr. Henry Milgrom et. al. of the National Jewish Medical and Research Center in Denver, Colo., published the clinical results of rhuMAB-25 in moderate to severe asthma patients (317 patients for 12 weeks, iv injection every two weeks) and concluded that this drug is "going to be a breakthrough" (New England Journal of Medicine, Dec. 23, 1999). A Biologics License Application (BLA) for this product has been submitted to the FDA in June, 2000 jointly by Novartis Pharmaceuticals Corporation, Tanox Inc., and Genetech, Inc. The positive results from anti-IgE antibody trials suggest that therapeutic strategies aimed at IgE down-regulation may be effective.

Cancer and Hyperproliferation Disorders

Cellular proliferation is a normal process that is vital to the normal functioning of most biological processes. Cellular proliferation occurs in all living organisms and involves two main processes: nuclear division (mitosis), and cytoplasmic division (cytokinesis). Because organisms are continually growing and replacing cells, cellular proliferation is essential to the vitality of the healthy cell. The disruption of normal cellular proliferation can result in a variety of disorders. For example, hyperproliferation of cells may cause psoriasis, thrombosis, atherosclerosis, coronary heart disease, myocardial infarction, stroke, smooth muscle neoplasms, uterine fibroid or fibroma, and obliterative diseases of vascular grafts and transplanted organs. Abnormal cell proliferation is most commonly associated with tumor formation and cancer.

Cancer is a major disease and is one of the leading causes of mortality both in the United States and internationally. Indeed, cancer is the second leading cause of death in the United States. According to the National Institute of Health, the overall annual cost for cancer is approximately $107 billion, which includes $37 billion for direct medical costs, $11 billion for indirect costs of lost productivity due to illness and $59 billion for indirect costs of lost productivity due to premature death. Not surprisingly, considerable efforts are underway to develop new treatments and preventative measures to combat this devastating illness.

Currently, cancer is primarily treated using a combination of surgery, radiation and chemotherapy. Chemotherapy involves the use of chemical agents to disrupt the replication and metabolism of cancerous cells. Chemotherapeutic agents which are currently being used to treat cancer can be classified into five main groups: natural products and their derivatives; anthacyclines; alkylating agents; antiproliferatives and hormonal agents.

One embodiment of the present invention discloses benzimidazole compounds that modulate IgE and inhibit cell proliferation. Benzimidazole compounds are known in the prior art, for example in European Patent No. 719,765 and U.S. Pat. No. 5,821,258. Both references, however, disclose compounds that contain an active ingredient that acts on DNA, and are structurally different from the benzimidazole derivatives of the current invention. The compounds of the prior art alkylate DNA and there is no suggestion in the references that the disclosed benzimidazole compounds modulate IgE or inhibit the cell proliferation. Further, the compounds described in both references are described as anticancer, antiviral or antimicrobial agents. The anti-allergy or anti-asthma properties of the benzimidazole compounds of the current invention have not previously been recognized. Further, in describing the anticancer properties of benzimidazole compounds, these references disclose chemotherapeutic agents that are DNA alkylating agents. The inhibition of cell proliferation using compounds of the present invention is not disclosed.

SUMMARY OF THE INVENTION

The present invention discloses several compounds that are active in down-regulating the IgE response to allergens and other provocative stimuli. One compound disclosed for use in the treatment of a condition associated with an excess IgE level and/or abnormal cell proliferation has a formula:

Genus I

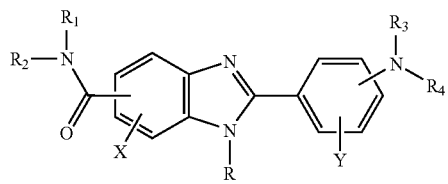

wherein R is selected from the group consisting of H, $C_1$–$C_5$ alkyl, benzyl, p-fluorobenzyl and di-alkylamino alkyl, wherein said. $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, OH, $OCH_3$, COOH, COOR' COR', CN, $CF_3$, $OCF_3$, $NO_2$, NR'R', NHCOR' and CONR'R';

wherein $R_3$ and $R_4$ are independently selected from the group consisting of H, alkyl, aryl, heteroaryl and COR';

wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein X and Y are independently selected from the group consisting of H, halogens, alkoxy, substituted alkoxy, alkyl, substituted alkyl, dialkylaminoalkyl, hydroxyalkyl, OH, $OCH_3$, COOH, CN, $CF_3$, $OCF_3$, $NO_2$, COOR", CHO and COR"; and wherein R" is a $C_1$–$C_8$ alkyl, wherein said $C_1$–$C_8$ alkyl is selected from the group consisting of a straight chain, branched or cyclic alkyl.

A compound of the aforementioned genus may contain a polycyclic aliphatic group which is selected from the group consisting of adamantyl, bicycloheptyl, camphoryl, bicyclo[2,2,2]octanyl and norbornyl.

A compound of the aforementioned genus may contain a heteroaryl and a substituted heteroaryl which is selected from the group consisting of pyridines, thiazoles, isothiazoles, oxazoles, pyrimidines, pyrazines, furans, thiophenes, isoxazoles, pyrroles, pyridazines, 1,2,3-triazines, 1,2,4-triazines, 1,3,5-triazines, pyrazoles, imidazoles, indoles, quinolines, iso-quinolines, benzothiophines, benzofurans, parathiazines, pyrans, chromenes, pyrrolidines, pyrazolidines, imidazolidines, morpholines, thiomorpholines, and the corresponding heterocyclics.

Specific compounds of Genus I are also disclosed in accordance with the current invention. These compounds are identified as Compounds I.1 to I.192 and their representative structures are illustrated below.

Another compound for use in the treatment of a condition associated with an excess IgE level and/or abnormal cell proliferation is disclosed in accordance with the present invention. The compound has a formula:

Genus II

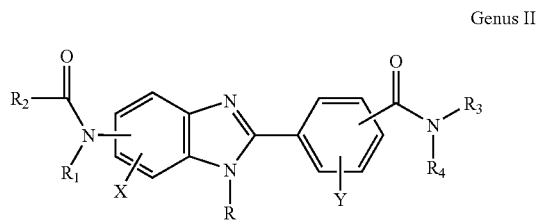

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, OH, $OCH_3$, COOH, COOR' COR', CN, $CF_3$, $OCF_3$, $NO_2$, NR'R', NHCOR' and CONR'R';

wherein $R_3$ and $R_4$ are independently selected from the group consisting of H, alkyl, aryl, heteroaryl and COR';

wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein X and Y are independently selected from the group consisting of H, halogens, alkoxy, substituted alkoxy, alkyl, substituted alkyl, dialkylaminoalkyl, hydroxyalkyl, OH, $OCH_3$, COOH, CN, $CF_3$, $OCF_3$, $NO_2$, COOR", CHO and COR"; and wherein R" is a $C_1$–$C_8$ alkyl, wherein said $C_1$–$C_8$ alkyl is selected from the group consisting of a straight chain, branched or cyclic alkyl.

A compound of the aforementioned genus may contain a polycyclic aliphatic group which is selected from the group consisting of adamantyl, bicycloheptyl, camphoryl, bicyclo[2,2,2]octanyl and norbornyl.

A compound of the aforementioned genus may contain a heteroaryl and a substituted heteroaryl which is selected from the group consisting of pyridines, thiazoles, isothiazoles, oxazoles, pyrimidines, pyrazines, furans, thiophenes, isoxazoles, pyrroles, pyridazines, 1,2,3-triazines, 1,2,4-triazines, 1,3,5-triazines, pyrazoles, imidazoles, indoles, quinolines, iso-quinolines, benzothiophines, benzofurans, parathiazines, pyrans, chromenes, pyrrolidines, pyrazolidines, imidazolidines, morpholines, thiomorpholines, and the corresponding heterocyclics.

Specific compounds of Genus II are also disclosed in accordance with the current invention. These compounds are identified as Compounds II.1 to II.90 and their representative structures are illustrated below.

Another compound for use in the treatment of a condition associated with an excess IgE level and/or abnormal cell proliferation is disclosed in accordance with the present invention. The compound has a formula:

Genus III

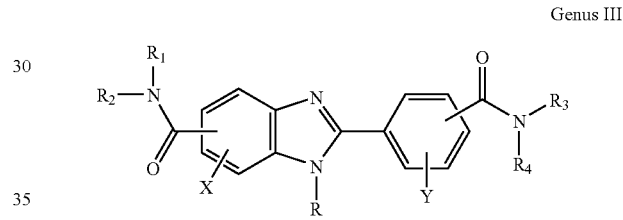

wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, OH, $OCH_3$, COOH, COOR' COR', CN, $CF_3$, $OCF_3$, $NO_2$, NR'R', NHCOR' and CONR'R';

wherein $R_3$ and $R_4$ are independently selected from the group consisting of H, alkyl, aryl, heteroaryl and COR';

wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein X and Y are independently selected from the group consisting of H, halogens, alkoxy, substituted alkoxy, alkyl, substituted alkyl, dialkylaminoalkyl, hydroxyalkyl, OH, OCH$_3$, COOH, CN, CF$_3$, OCF$_3$, NO$_2$, COOR", CHO and COR"; and wherein R" is a C$_1$–C$_8$ alkyl, wherein said C$_1$–C$_8$ alkyl is selected from the group consisting of a straight chain, branched or cyclic alkyl.

A compound of the aforementioned genus may contain a polycyclic aliphatic group which is selected from the group consisting of adamantyl, bicycloheptyl, camphoryl, bicyclo[2,2,2]octanyl and norbornyl.

A compound of the aforementioned genus may contain a heteroaryl and a substituted heteroaryl which is selected from the group consisting of pyridines, thiazoles, isothiazoles, oxazoles, pyrimidines, pyrazines, furans, thiophenes, isoxazoles, pyrroles, pyridazines, 1,2,3-triazines, 1,2,4-triazines, 1,3,5-triazines, pyrazoles, imidazoles, indoles, quinolines, iso-quinolines, benzothiophines, benzofurans, parathiazines, pyrans, chromenes, pyrrolidines, pyrazolidines, imidazolidines, morpholines, thiomorpholines, and the corresponding heterocyclics.

Specific compounds of Genus III are also disclosed in accordance with the current invention. These compounds are identified as Compounds III.1 to III.154 and their representative structures are illustrated below.

For each chemical structure disclosed herein, the hydrogen atoms on the heteroatoms have been omitted for clarity purposes. Where open valences on heteroatoms are indicated, it is assumed that these valences are filled by hydrogen atoms.

A method for treating a disease condition associated with excess IgE and/or abnormal cell proliferation (i.e. cancer) in a mammal is also disclosed. In one aspect, the method comprises the step of administering to the mammal an IgE-suppressing amount or anti-cell proliferation amount of a pharmaceutical formulation comprising at least one benzimidazole compound from the above-disclosed small molecule families.

In accordance with a variation of the method of treatment, the small molecule IgE-suppressing compound may be administered in conjunction with at least one additional agent, which is active in reducing a symptom associated with an allergic reaction. In one embodiment, the small molecule inhibitor may be mixed with at least one additional active ingredient to form a pharmaceutical composition. Alternatively, the small molecule inhibitor may be co-administered at the same time or according to different treatment regimens with the at least one additional active agent.

The at least one additional active ingredient may be a short-acting β$_2$-adrenergic agonist selected from the group consisting of terbutaline and albuterol; a long-acting β$_2$-adrenergic agonist selected from the group consisting of salmeterol and formoterol; an antihistamine selected from the group consisting of loratadine, azelastine and ketotifen; a phosphodiesterase inhibitor, an anticholinergic agent, a corticosteroid, an inflammatory mediator release inhibitor or a leukotriene receptor antagonist.

In another embodiment, the benzimidazole compound may be administered in conjunction with at least one additional active agent. These active agents include antifungals, antivirals, antibiotics, anti-inflammatories, and anticancer agents. Anticancer agents include, but are not limited to, alkylating agents (lomustine, carmustine, streptozocin, mechlorethamine, melphalan, uracil nitrogen mustard, chlorambucil cyclophosphamide, iphosphamide, cisplatin, carboplatin mitomycin thiotepa dacarbazine procarbazine, hexamethyl melamine, triethylene melamine, busulfan, pipobroman, and mitotane); antimetabolites (methotrexate, trimetrexate pentostatin, cytarabine, ara-CMP, fludarabine phosphate, hydroxyurea, fluorouracil, floxuridine, chlorodeoxyadenosine, gemcitabine, thioguanine, and 6-mercaptopurine); DNA cutters (bleomycin); topoisomerase I poisons (topotecan irinotecan and camptothecin); topoisomerase II poisons (daunorubicin, doxorubicin, idarubicin, mitoxantrone, teniposide, and etoposide); DNA binders (dactinomycin, and mithramycin); and spindle poisons (vinblastine, vincristine, navelbine, paclitaxel, and docetaxel).

In another embodiment, the benzimidazole compounds of the current invention are administered in conjunction with one or more other therapies. These therapies include, but are not limited to radiation, immunotherapy, gene therapy and surgery. These combination therapies may be administered simultaneously or sequentially. For example, radiation may be administered along with the administration of benzimidazole compounds, or may be administered at any time before or after administration of benzimidazole compounds.

A dose of about 0.01 mg to about 100 mg per kg body weight per day of the small molecule IgE inhibitory compound is preferably administered in divided doses daily.

A method for treating a disease condition associated with excess IgE or abnormal cell proliferation in a mammal is also disclosed which comprises the step of administering to the mammal an therapeutic amount of a pharmaceutical formulation comprising at least one compound selected from Genus I, Genus II and/or Genus III.

The methods provided herein for treating diseases and processes mediated by undesired, uncontrolled or abnormal cell proliferation, such as cancer, involve administering to a mammal a composition of the benzimidazole compounds disclosed herein to inhibit cell proliferation. The method is particularly useful for preventing or treating tumor formation and progresson. In one embodiment of the invention, the compounds and methods disclosed are especially useful in treating estrogen receptor positive and estrogen receptor negative type breast cancers.

Other variations within the scope of the present invention may be more fully understood with reference to the following detailed description.

DETAILED DESCRIPTION OF THE PREFERRED EMBODIMENT

Figure 1:
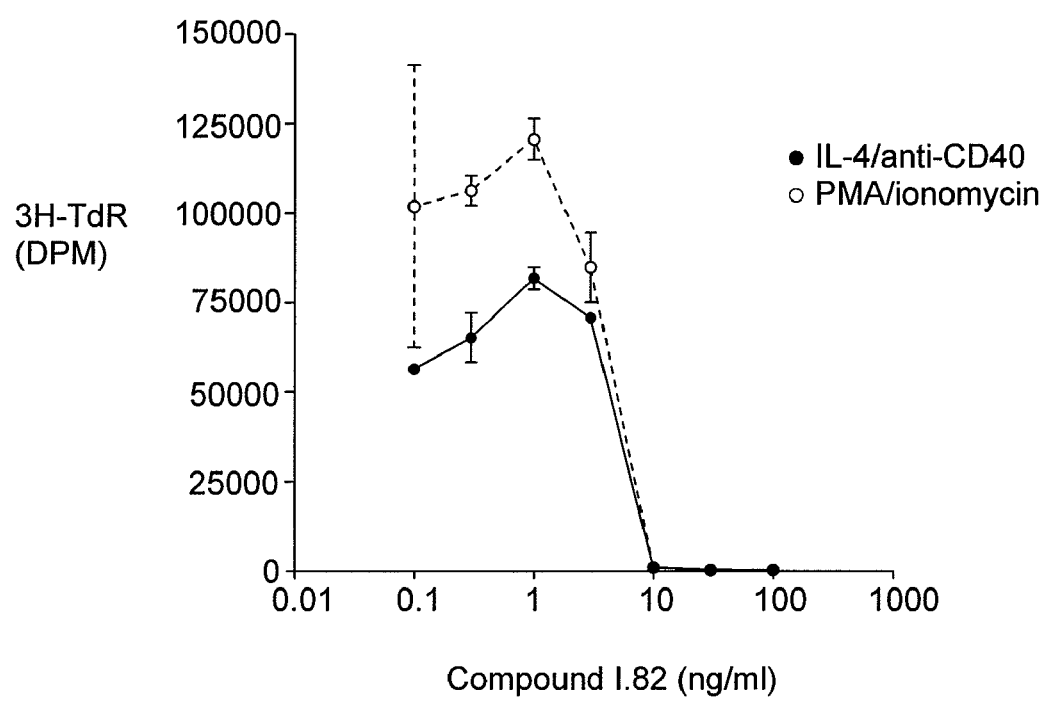
FIG. 1 shows suppression of spleen cell proliferation responses by Compound I.82. Spleen cell cultures were established from naive BALB/c mice and incubated for 4 days in the presence of stimulus and drug. Cultures were pulsed for 4 hours with 3H-thymidine and harvested.

The present invention is directed to small molecule inhibitors of IgE which are useful in the treatment of allergy and/or asthma or any diseases where IgE is pathogenic. The inhibitors may affect the synthesis, activity, release, metabolism, degradation, clearance and/or pharmacokinetics of IgE. The particular compounds disclosed herein were identified by their ability to suppress IgE levels in both ex vivo and in vivo assays. The compounds disclosed in the current invention are also useful in the treatment of diseases associated with abnormal cellular proliferation, including, but not limited to, tumorgenesis and other proliferative diseases such as cancers, inflammatory disorders and circulatory diseases.

Development and optimization of clinical treatment regimens can be monitored by those of skill in the art by reference to the ex vivo and in vivo assays described below.

Ex Vivo Assay

This system begins with in vivo antigen priming and measures secondary antibody responses in vitro. The basic protocol was documented and optimized for a range of parameters including: antigen dose for priming and time span following priming, number of cells cultured in vitro, antigen concentrations for eliciting secondary IgE (and other Ig's) response in vitro, fetal bovine serum (FBS) batch that will permit optimal IgE response in vitro, the importance of primed CD4+ T cells and hapten-specific B cells, and specificity of the ELISA assay for IgE (Marcelletti and Katz, *Cellular Immunology* 135:471–489 (1991); incorporated herein by reference).

The actual protocol utilized for this project was adapted for a more high throughput analyses. BALB/cByj mice were immunized i.p. with 10 μg DNP-KLH adsorbed onto 4 mg alum and sacrificed after 15 days. Spleens were excised and homogenized in a tissue grinder, washed twice, and maintained in DMEM supplemented with 10% FBS, 100 U/ml penicillin, 100 μg/ml streptomycin and 0.0005% 2-mercaptoethanol. Spleen cell cultures were established (2–3 million cells/ml, 0.2 ml/well in quadruplicate, 96-well plates) in the presence or absence of DNP-KLH (10 ng/ml). Test compounds (2 μg/ml and 50 ng/ml) were added to the spleen cell cultures containing antigen and incubated at 37° C. for 8 days in an atmosphere of 10% $CO_2$.

Culture supernatants were collected after 8 days and Ig's were measured by a modification of the specific isotype-selective ELISA assay described by Marcelletti and Katz (supra). The assay was modified to facilitate high throughput. ELISA plates were prepared by coating with DNP-KLH or DNP-OVA overnight. After blocking with bovine serum albumin (BSA), an aliquot of each culture supernatant was diluted (1:4 in phosphate buffered saline (PBS) with BSA, sodium azide and Tween 20), added to the ELISA plates, and incubated overnight in a humidified box at 4° C. IgE levels were quantitated following successive incubations with biotinylated-goat antimouse IgE (b-GAME), AP-streptavidin and substrate.

Antigen-specific IgG1 was measured similarly, except that culture supernatants were diluted 200-fold and biotinylated-goat antimouse IgG1 (b-GAMG1) was substituted for b-GAME. IgG2a was measured in ELISA plates that were coated with DNP-KLH following a 1:20 dilution of culture supernatants and incubation with biotinylated-goat antimouse IgG2a (b-GAMG2a). Quantitation of each isotype was determined by comparison to a standard curve. The level of detectability of all antibody was about 200–400 pg/ml and there was less than 0.001% cross-reactivity with any other Ig isotype in the ELISA for IgE.

In Vivo Assay

Compounds found to be active in the ex vivo assay (above) were further tested for their activity in suppressing IgE responses in vivo. Mice receiving low-dose radiation prior to immunization with a carrier exhibited an enhanced IgE response to challenge with antigen 7 days later. Administration of the test compounds immediately prior to and after antigen sensitization, measured the ability of that drug to suppress the IgE response. The levels of antigen specific IgE, IgG1 and IgG2a in serum were compared.

Female BALB/cByj mice were irradiated with 250 rads 7 hours after initiation of the daily light cycle. Two hours later, the mice were immunized i.p. with 2 μg of KLH in 4 mg alum. Two to seven consecutive days of drug injections were initiated 6 days later on either a once or twice daily basis. Typically, i.p. injections and oral gavages were administered as suspensions (150 μl/injection) in saline with 10% ethanol and 0.25% methylcellulose. Each treatment group was composed of 5–6 mice. On the second day of drug administration, 2 μg of DNP-KLH was administered i.p. in 4 mg alum, immediately following the morning injection of drug. Mice were bled 7–21 days following DNP-KLH challenge.

Antigen-specific IgE, IgG1 and IgG2a antibodies were measured by ELISA. Periorbital bleeds were centrifuged at 14,000 rpm for 10 min, the supernatants were diluted 5-fold in saline, and centrifuged again. Antibody concentrations of each bleed were determined by ELISA of four dilutions (in triplicate) and compared to a standard curve: anti-DNP IgE (1:100 to 1:800), anti-DNP IgG2a (1:100 to 1:800), and anti-DNP IgG1 (1:1600 to 1:12800).

Active Compounds of the Present Invention

The following series of compounds, identified under subheadings Genus I, Genus II and Genus III, were found to be potent inhibitors of IgE in both ex-vivo and in vivo models. These compounds also exhibit anti-proliferative effects, and, as such, may be used as agents to treat hyperproliferation disorders, including cancer.

Compounds of Genus I

One family of small molecule IgE inhibitors in accordance with the present invention include benzimidazole carboxamides, defined by the following genus (Genus I):

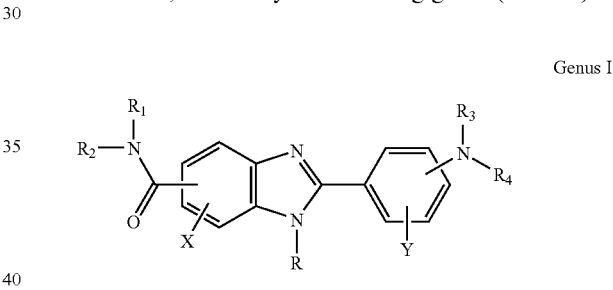

Genus I wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, OH, $OCH_3$, COOH, COOR' COR', CN, $CF_3$, $OCF_3$, $NO_2$, NR'R', NHCOR' and CONR'R';

wherein $R_3$ and $R_4$ are independently selected from the group consisting of H, alkyl, aryl, heteroaryl and COR';

wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein X and Y are independently selected from the group consisting of H, halogens, alkoxy, substituted alkoxy, alkyl, substituted alkyl, dialkylaminoalkyl, hydroxyalkyl, OH, OCH$_3$, COOH, CN, CF$_3$, OCF$_3$, NO$_2$, COOR", CHO and COR"; and wherein R" is a C$_1$–C$_8$ alkyl, wherein said C$_1$–C$_8$ alkyl is selected from the group consisting of a straight chain, branched or cyclic alkyl.

The following specific compounds are encompassed within the definition of the benzimidazole carboxamide genus (Genus I):

I.1

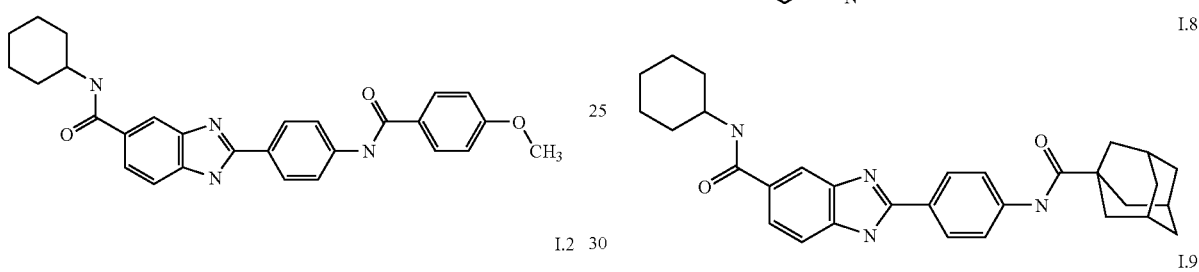

I.2

I.3

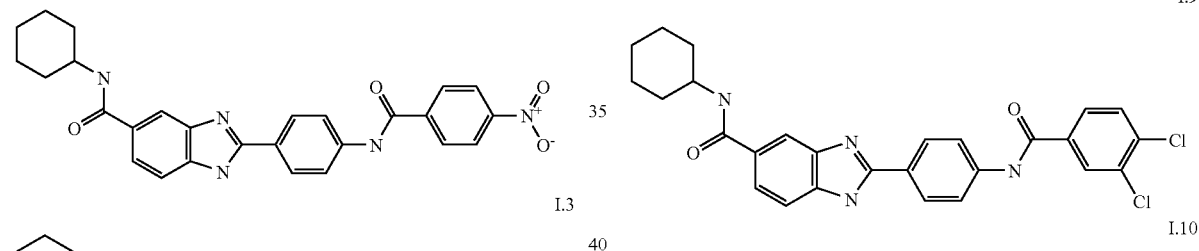

I.4

I.5

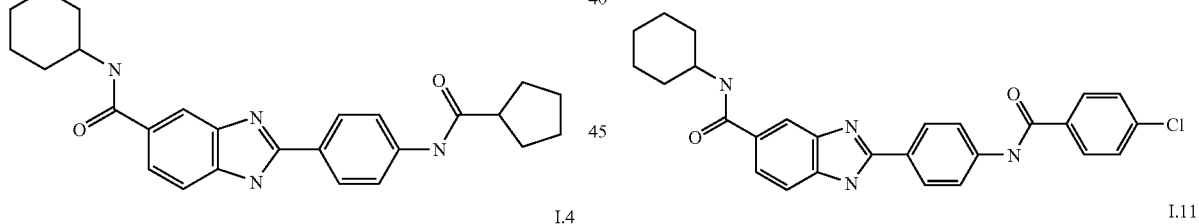

I.6

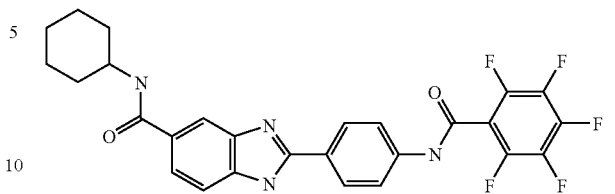

I.7

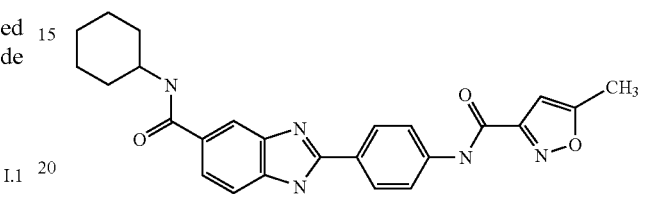

I.8

I.9

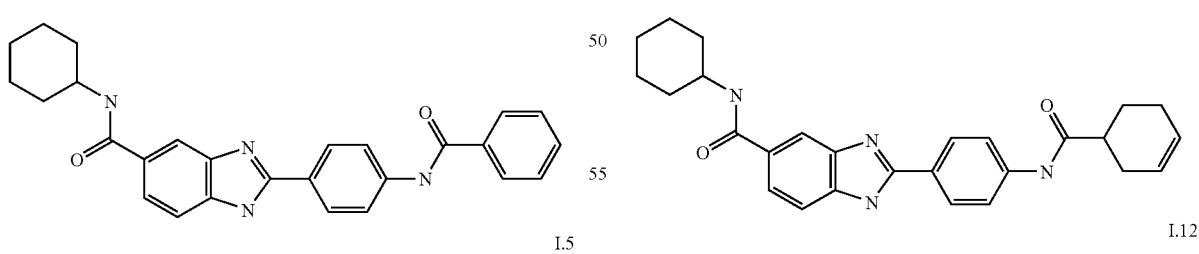

I.10

I.11

I.12

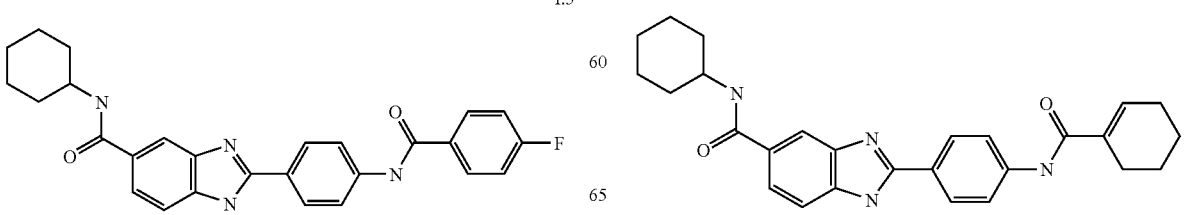

-continued

I.13
I.14
I.15
I.16
I.17
I.18
I.19
I.20
I.21
I.22
I.23
I.24
I.25
I.26

-continued
I.27
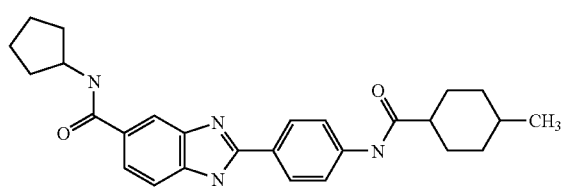
I.28
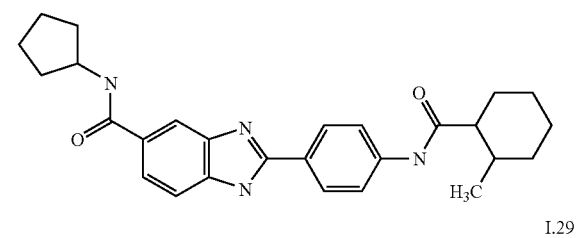
I.29
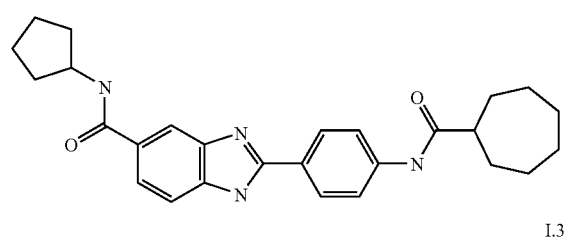
I.30
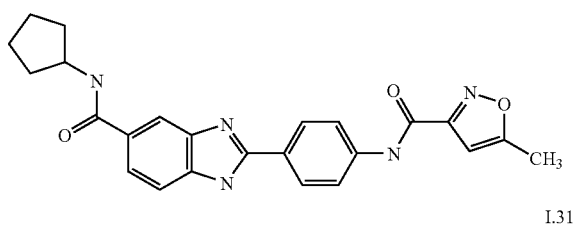
I.31
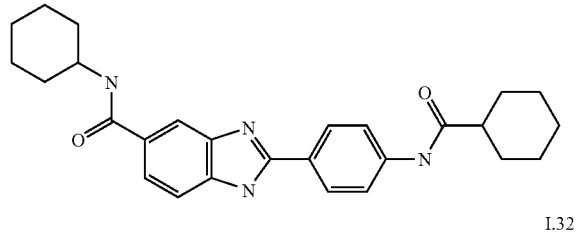
I.32
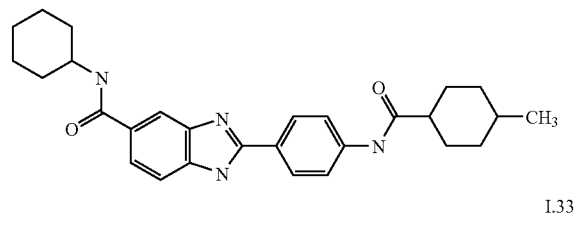
I.33
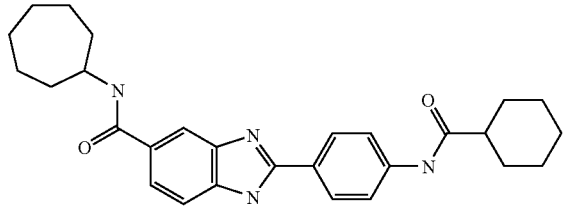
-continued
I.34
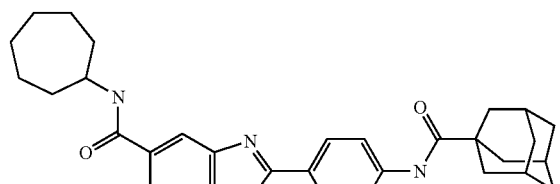
I.35
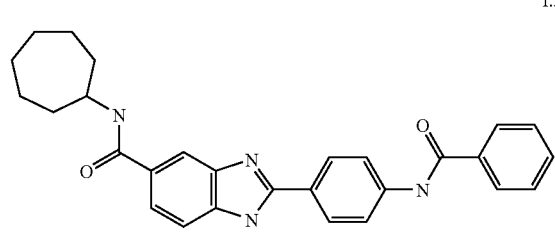
I.36
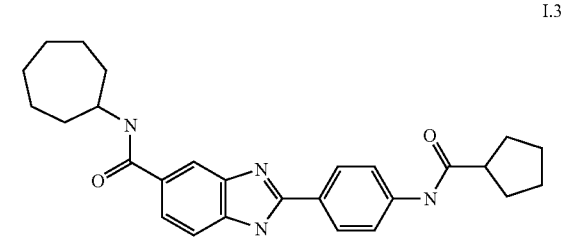
I.37
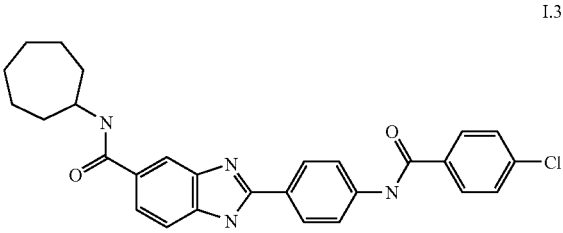
I.38
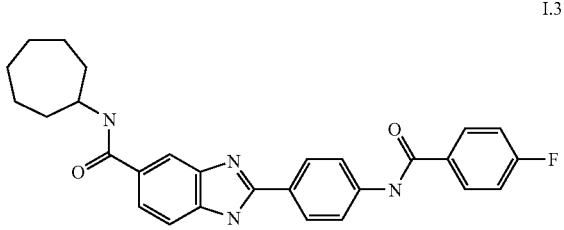
I.39
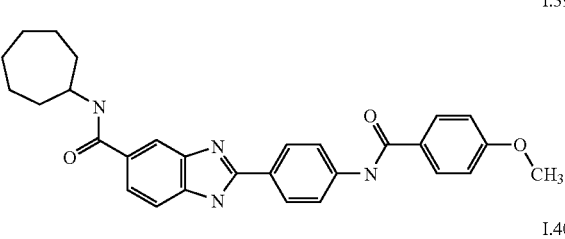
I.40
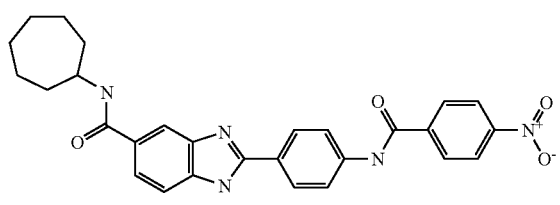

-continued
I.41
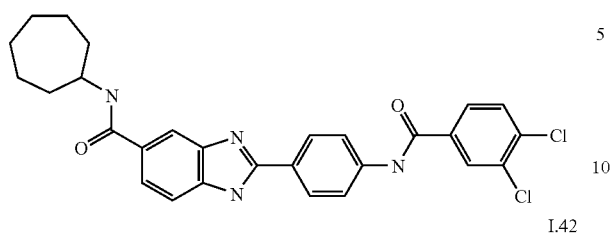
I.42
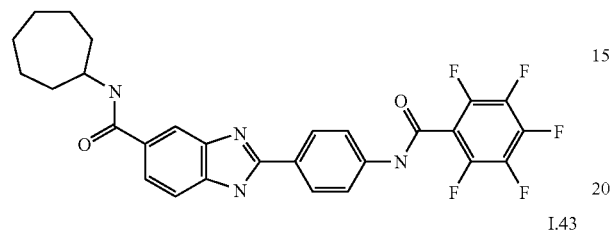
I.43
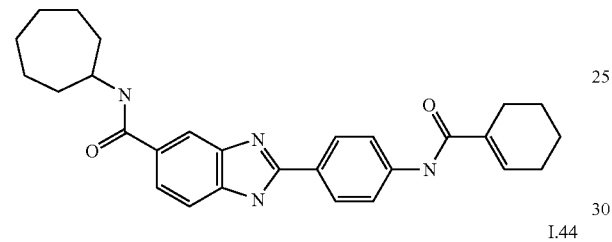
I.44
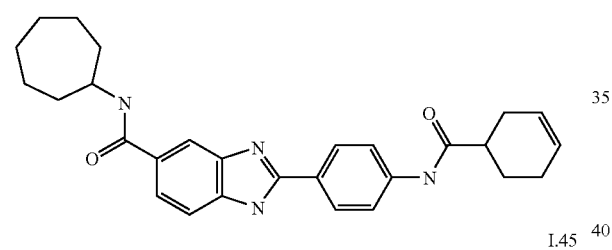
I.45
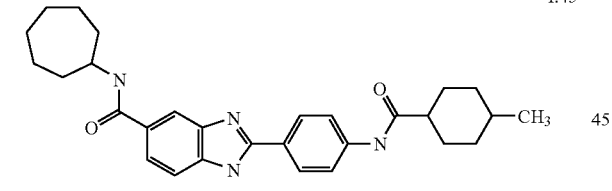
I.46
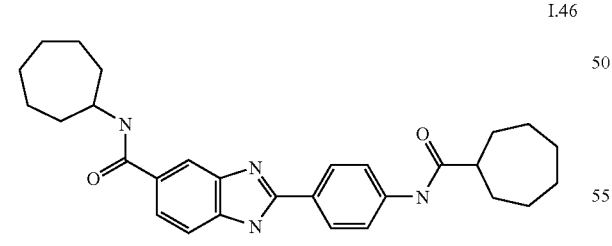
I.47
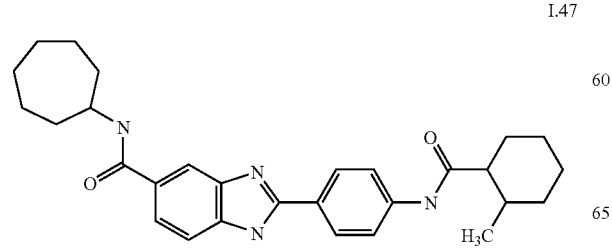
-continued
I.48
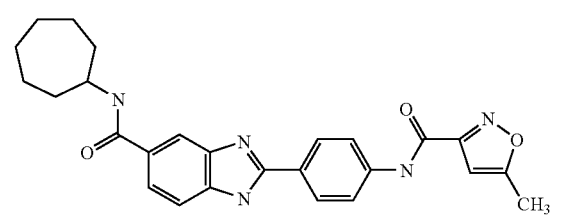
I.49
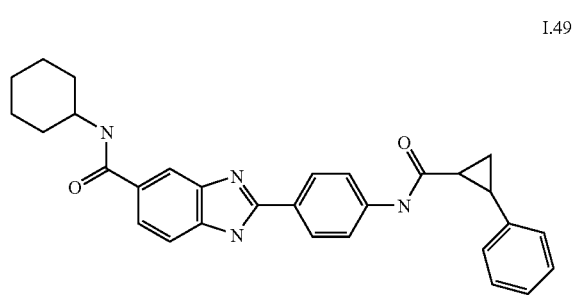
I.50
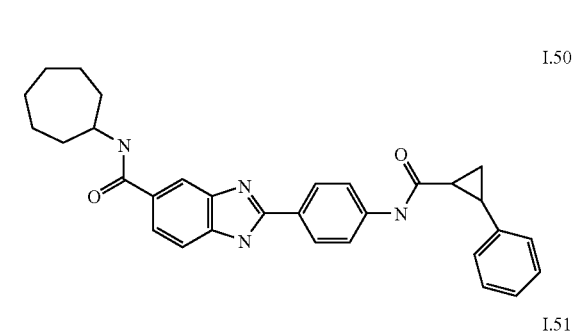
I.51
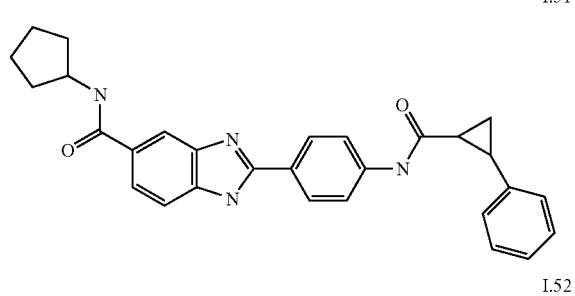
I.52
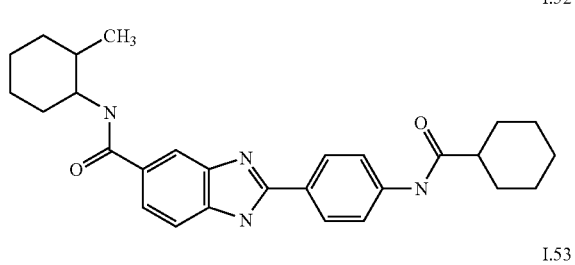
I.53
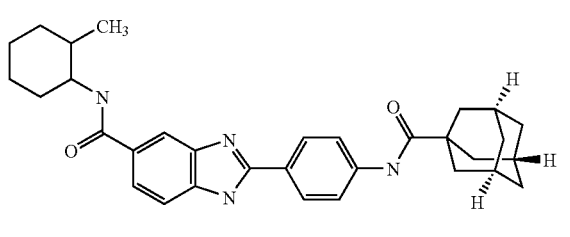

-continued
I.54
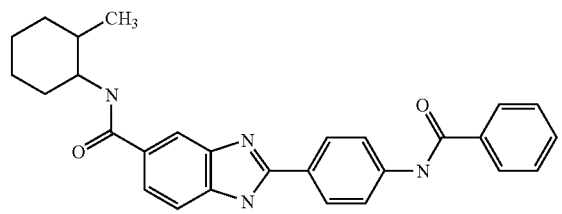
I.55
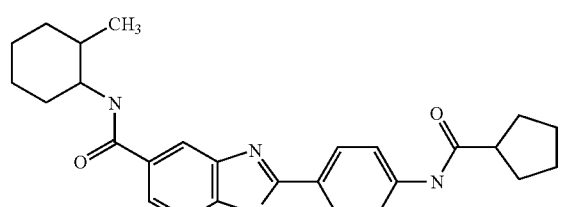
I.56
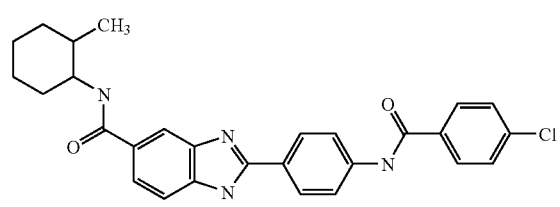
I.57
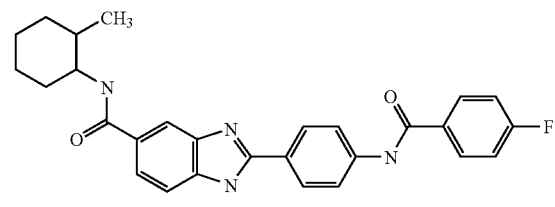
I.58
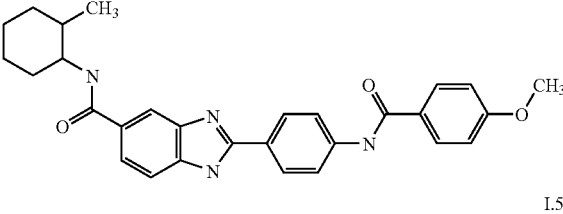
I.59
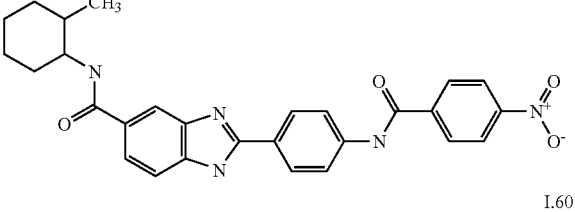
I.60
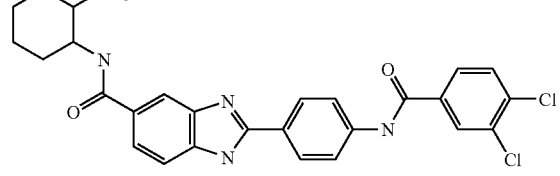
-continued
I.61
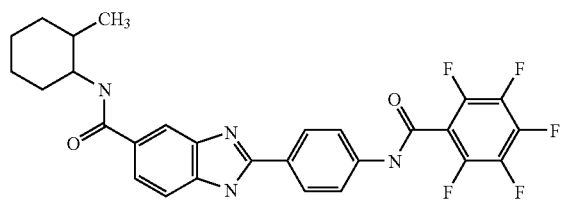
I.62
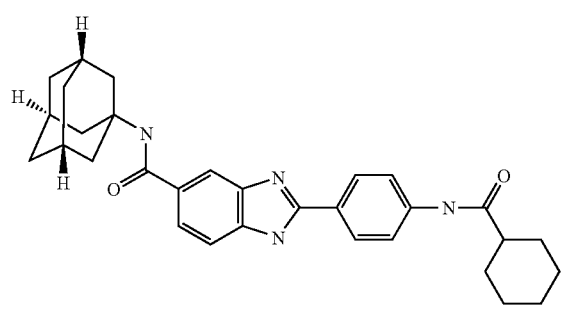
I.63
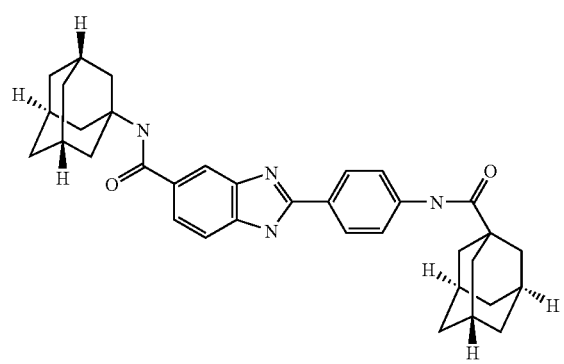
I.64
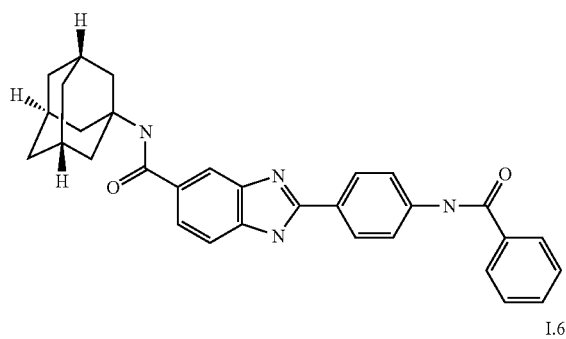
I.65
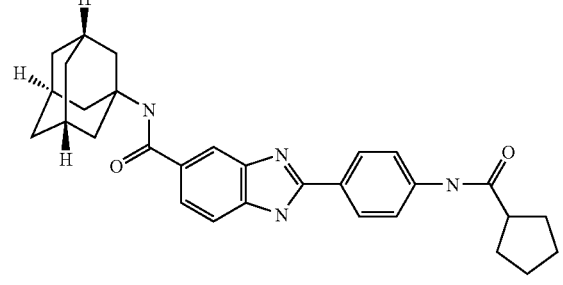

-continued
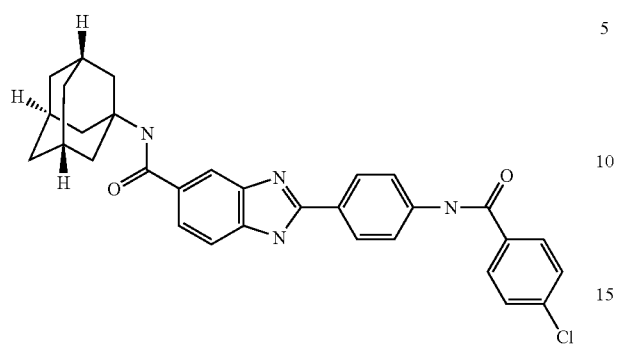
I.66
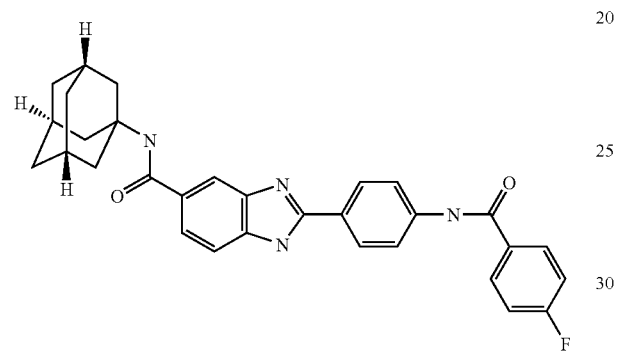
I.67
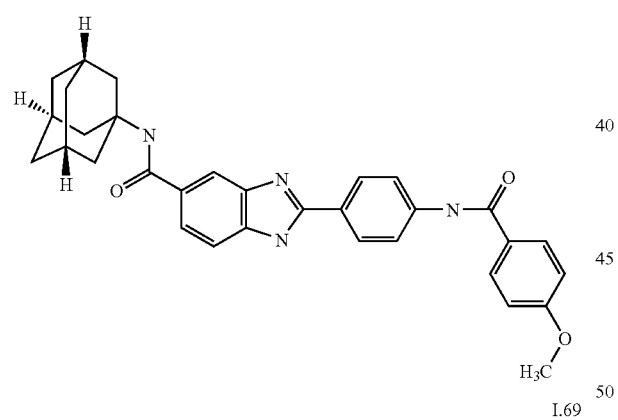
I.68
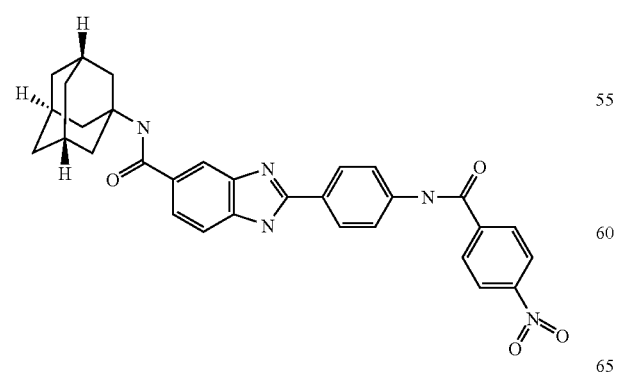
I.69
-continued
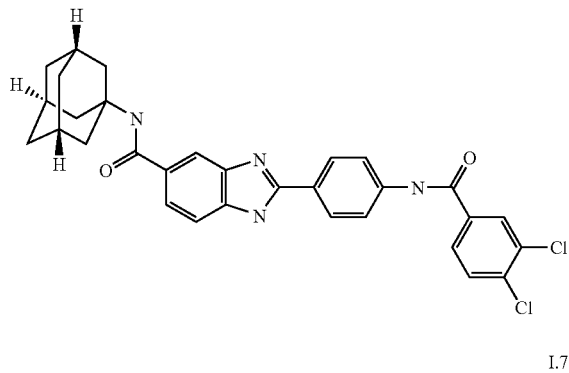
I.70
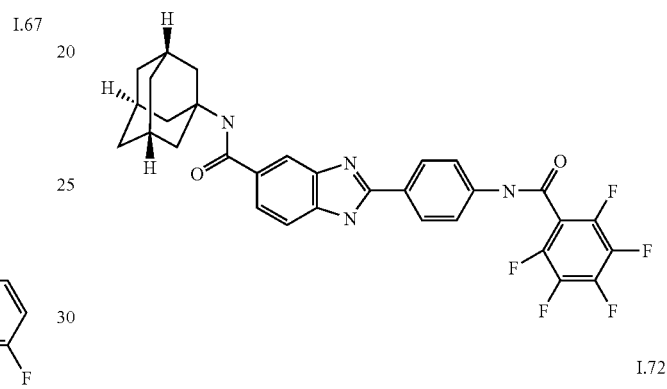
I.71
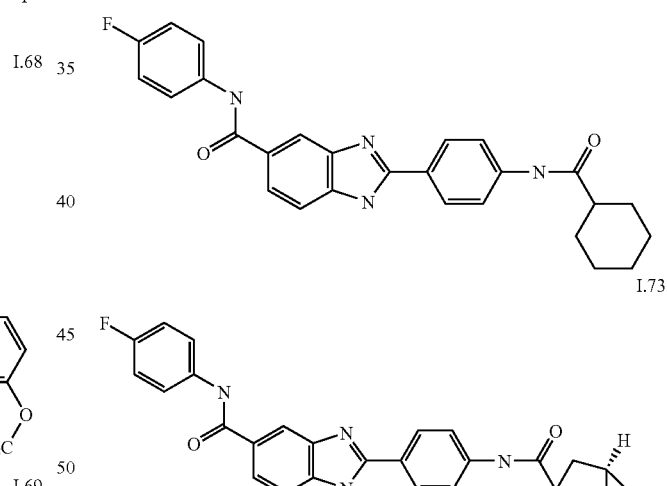
I.72
I.73
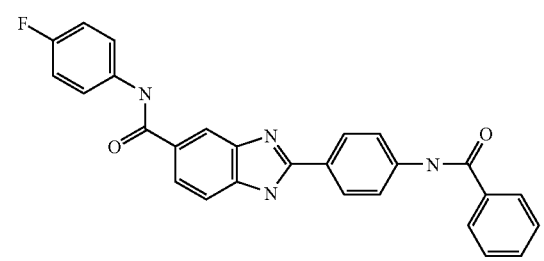
I.74

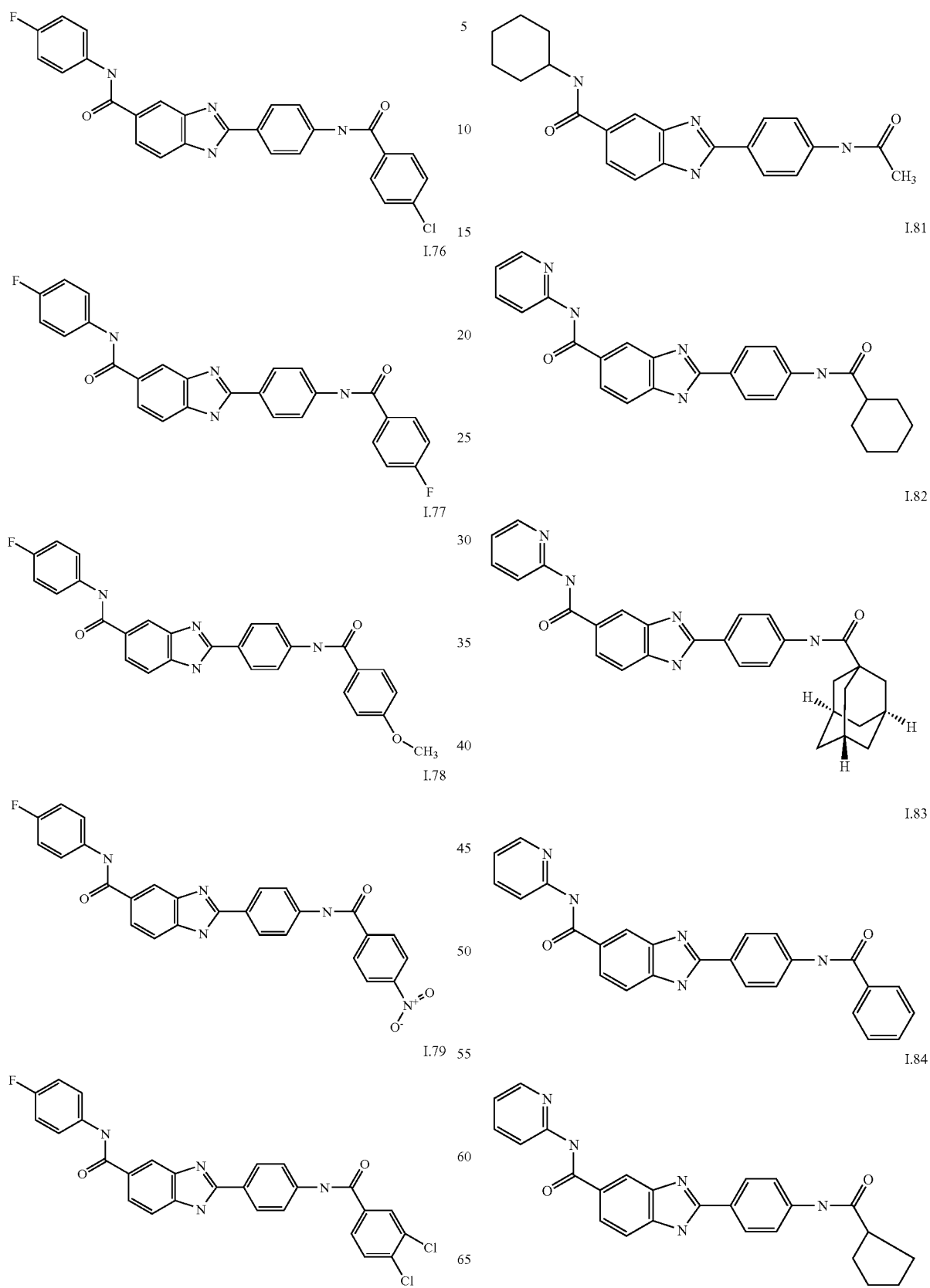

I.85
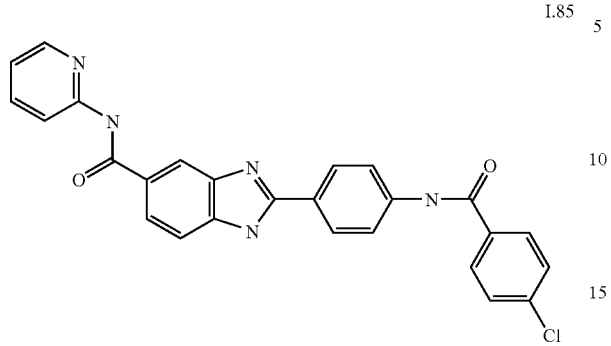
I.89
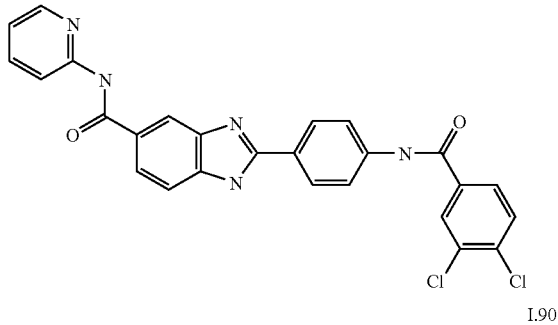
I.86
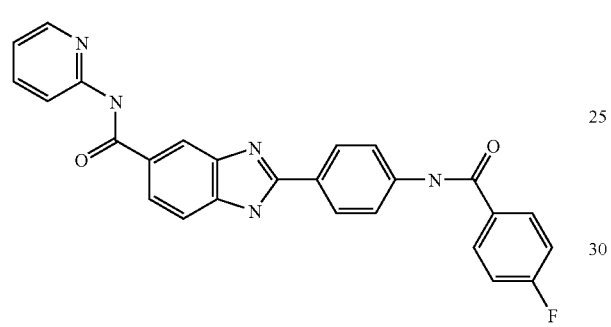
I.90
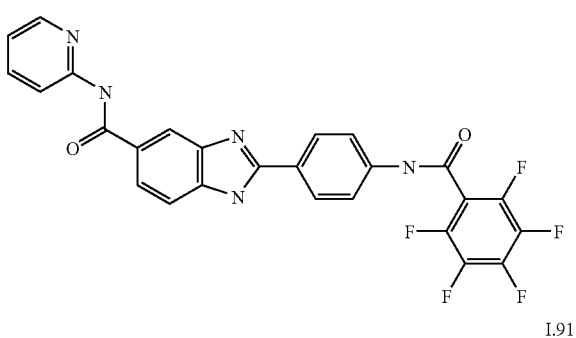
I.91
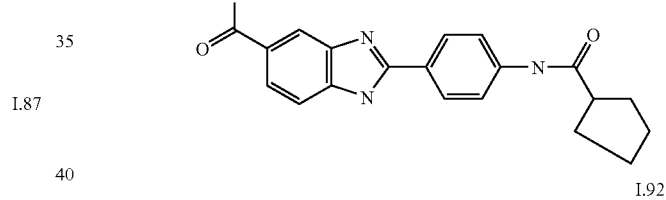
I.87
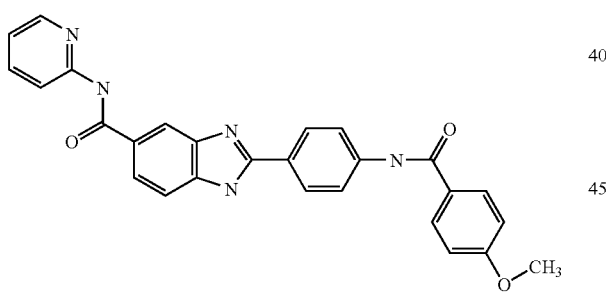
I.92
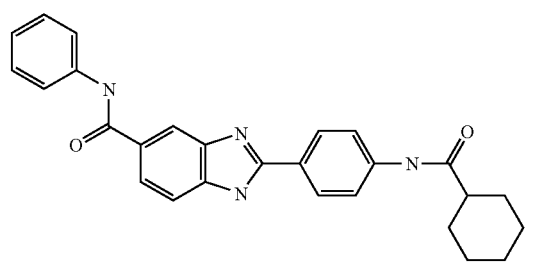
I.93
I.88
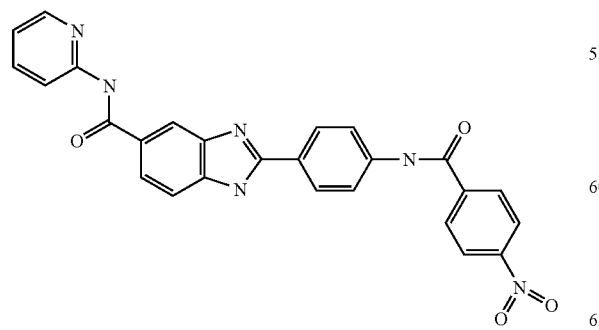
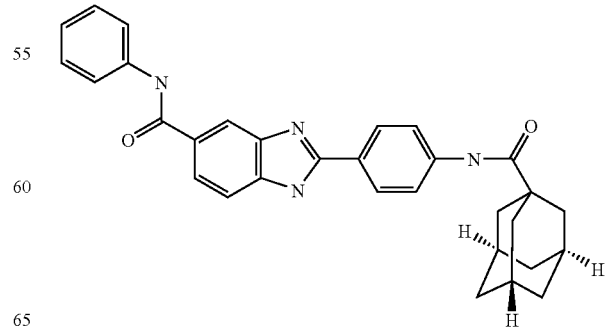

I.94
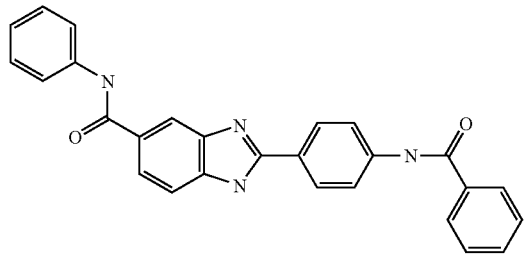
I.95
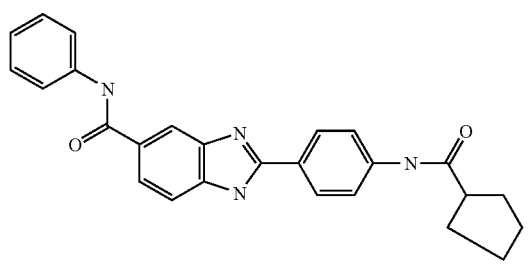
I.96
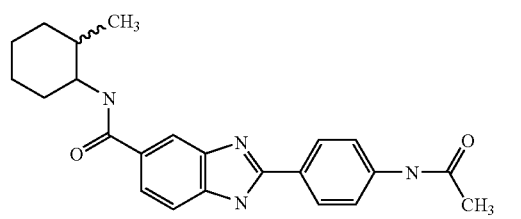
I.97
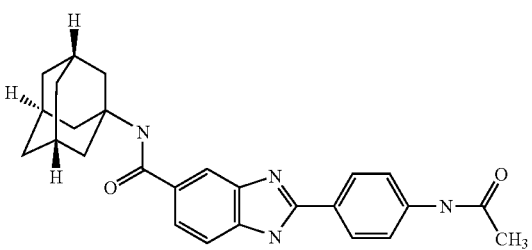
I.98
I.99
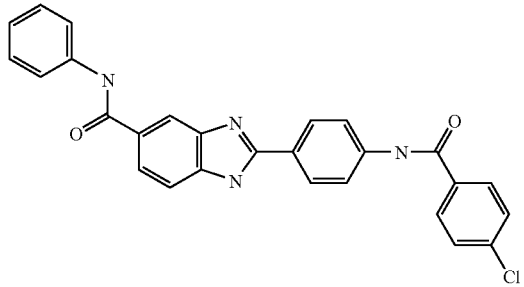
I.100
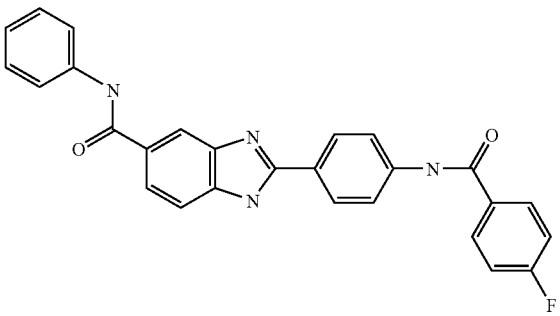
I.101
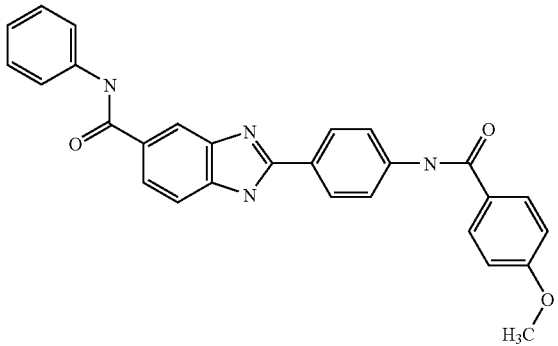
I.102
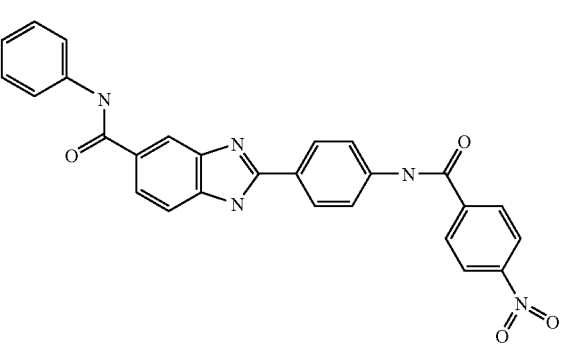

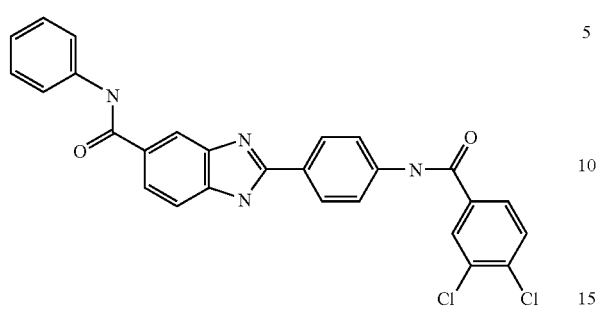
I.103
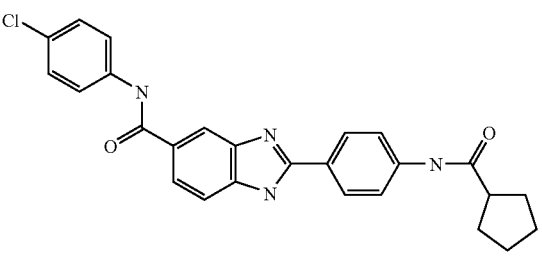
I.108
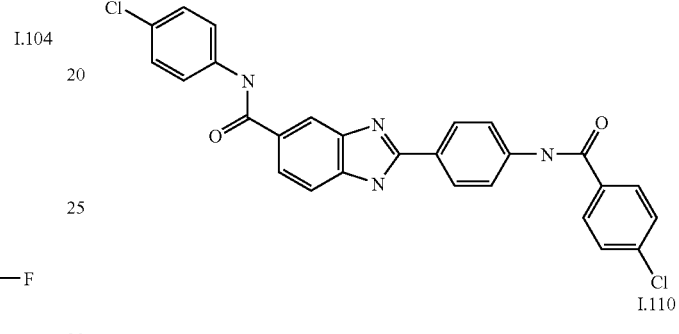
I.104, I.109, I.110
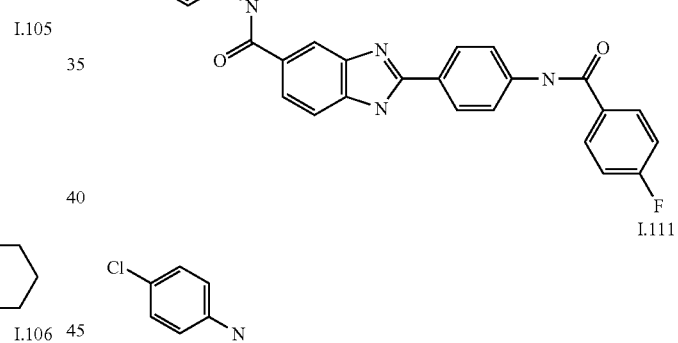
I.105, I.111
I.106
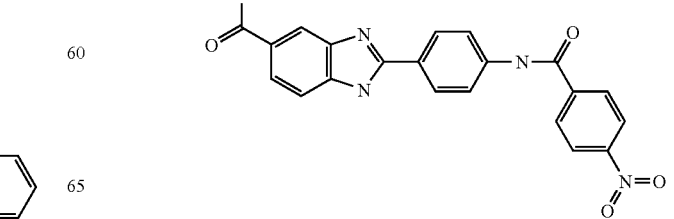
I.107, I.112

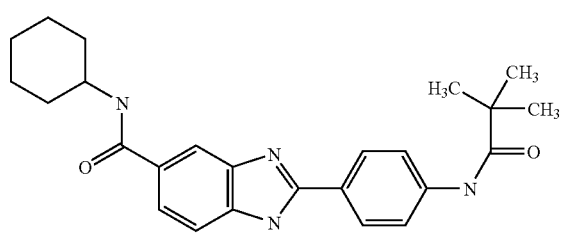
I.113
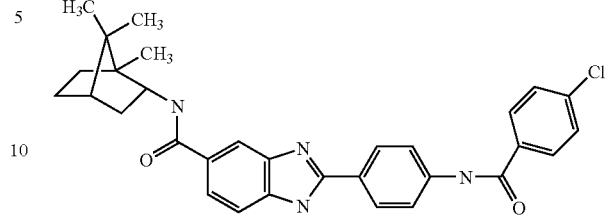
I.119
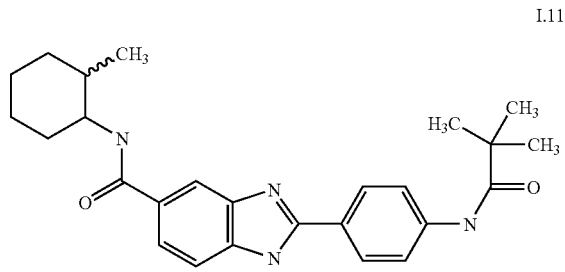
I.114
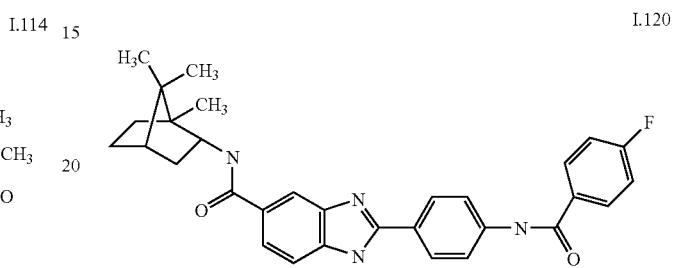
I.120
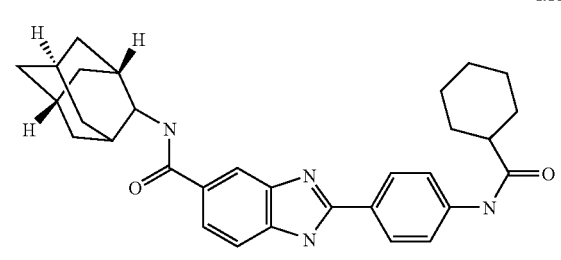
I.115
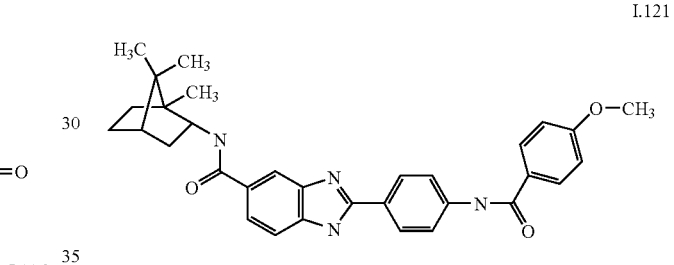
I.121
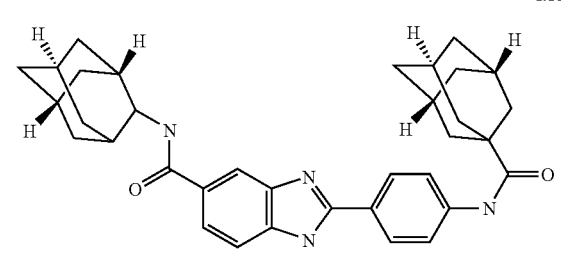
I.116
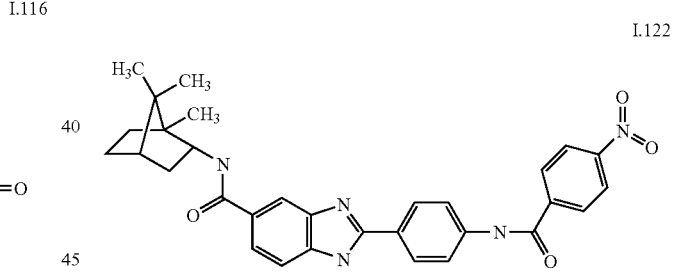
I.122
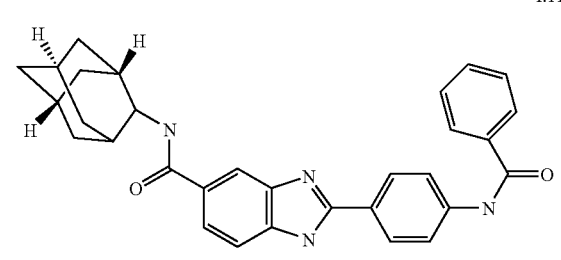
I.117
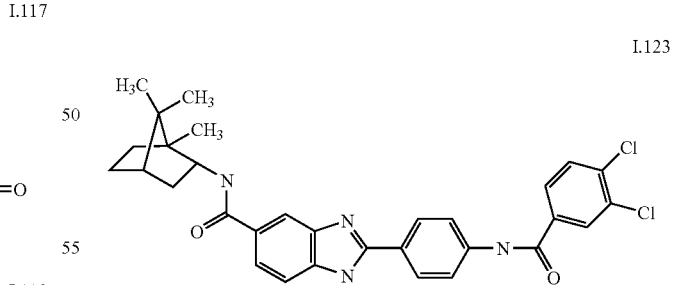
I.123
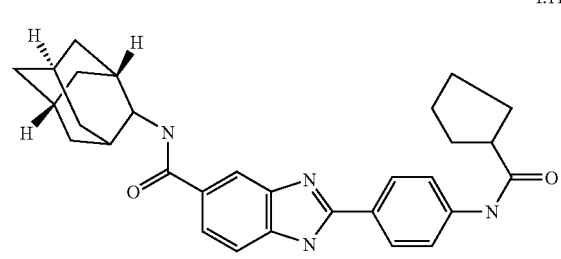
I.118
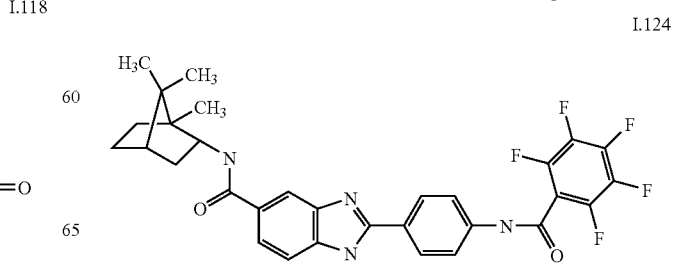
I.124

I.125
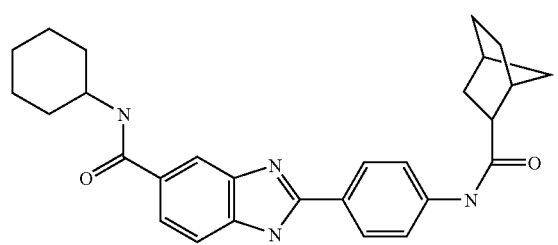
I.126
I.131
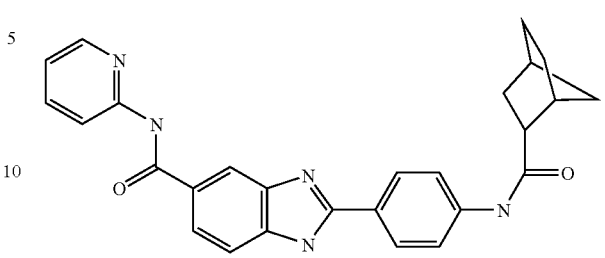
I.132
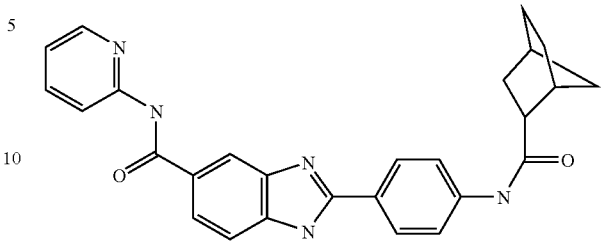
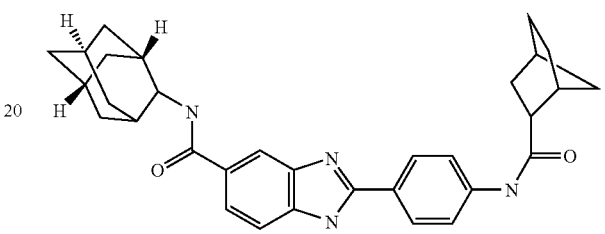
I.127
I.133
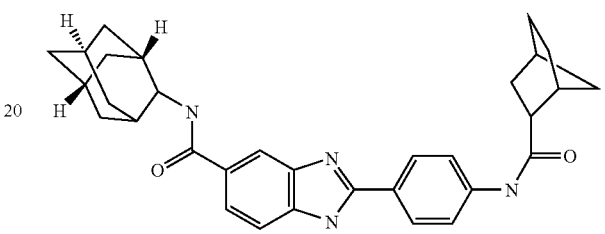
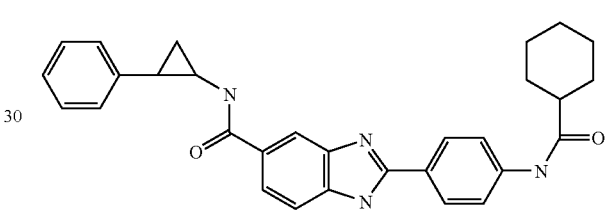
I.128
I.134
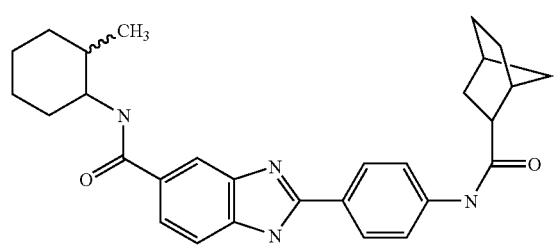
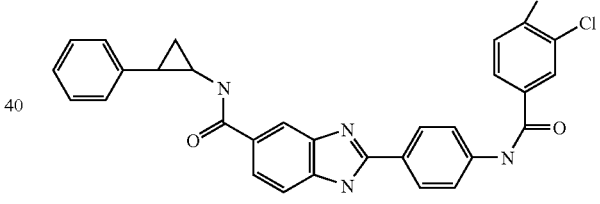
I.129
I.135
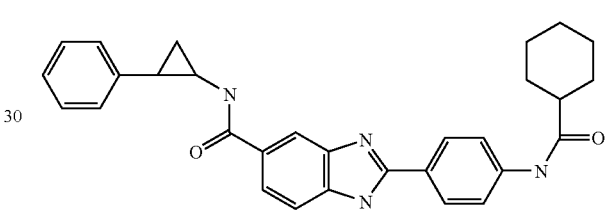
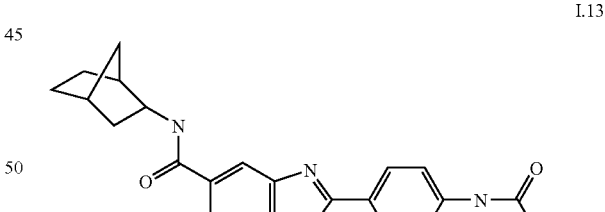
I.130
I.136
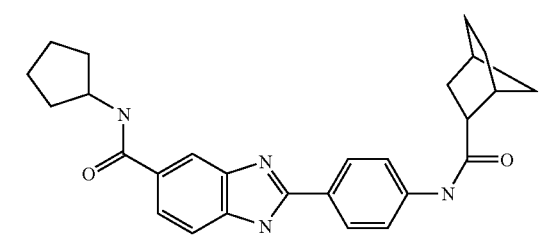
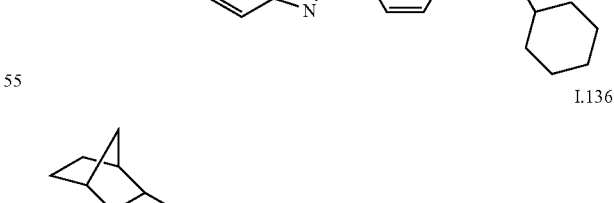

I.137
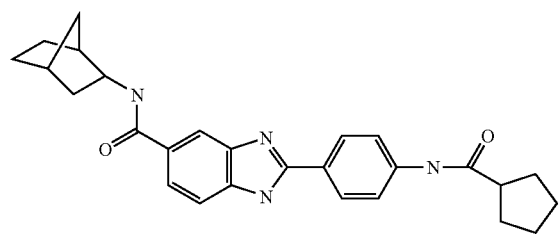
I.138
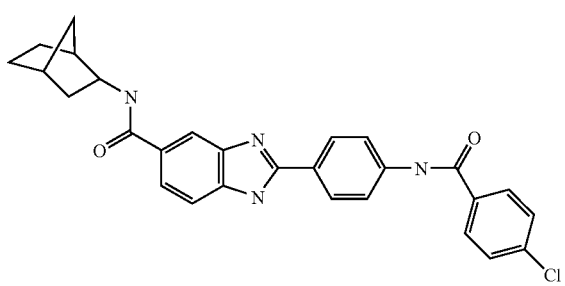
I.139
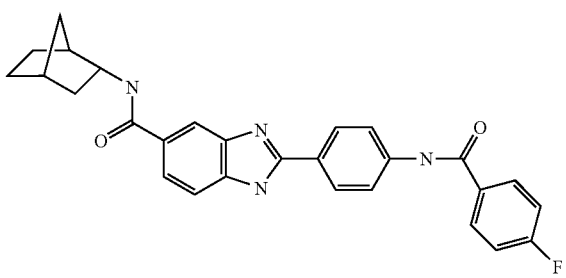
I.140
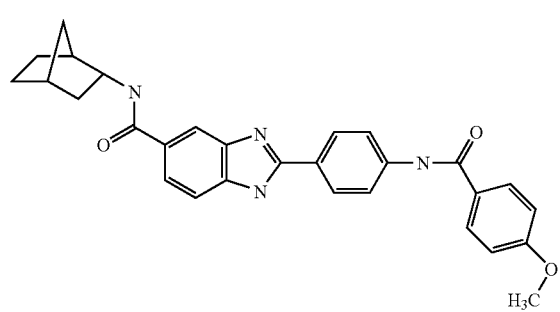
I.141
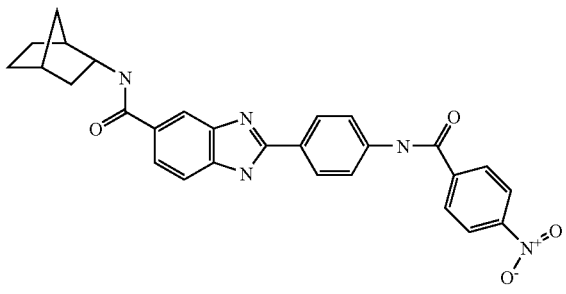
I.142
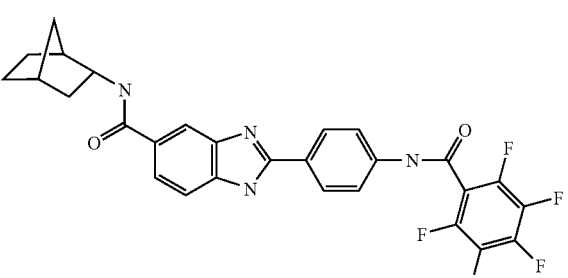
I.143
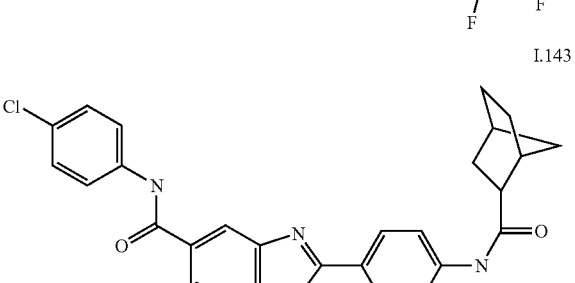
I.144
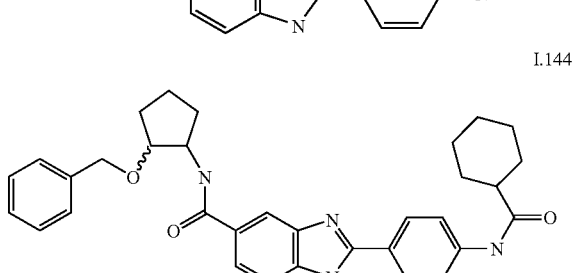
I.145
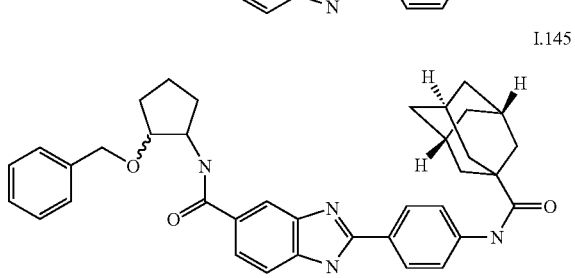
I.146
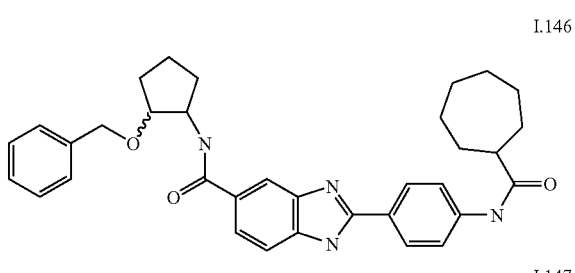
I.147
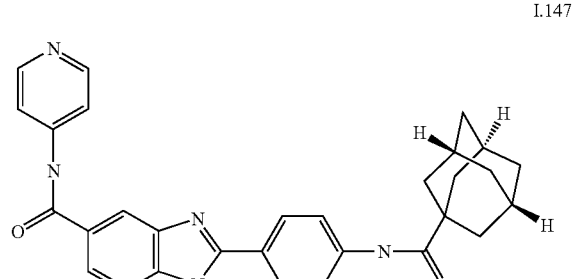

-continued

I.148
I.149
I.150
I.151
I.152
I.153
I.154
I.155
I.156
I.157

-continued
I.158
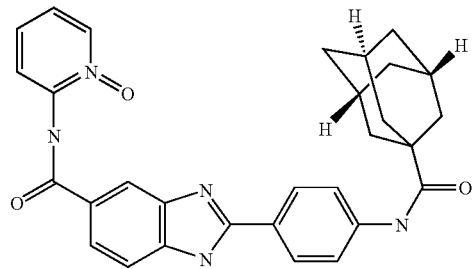
I.163
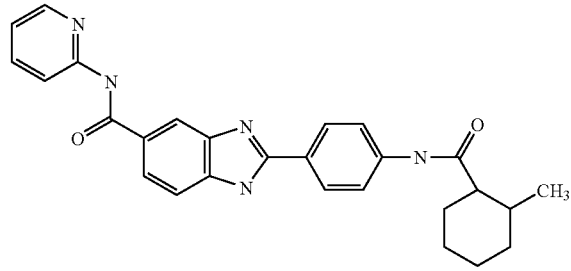
I.159
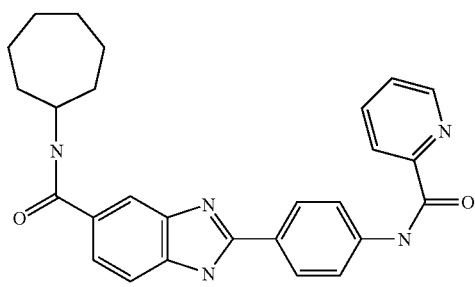
I.164
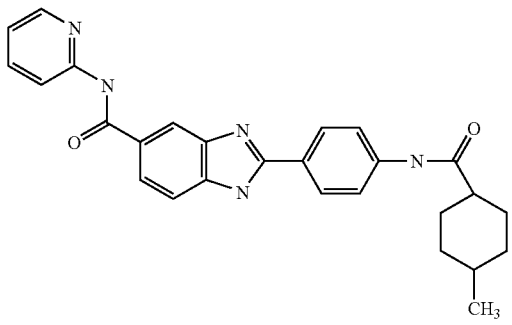
I.160
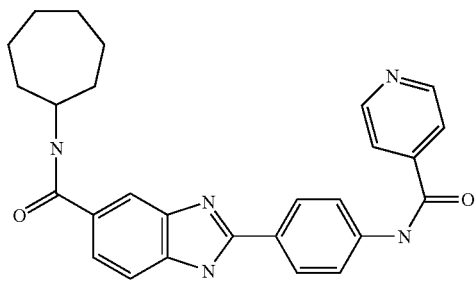
I.165
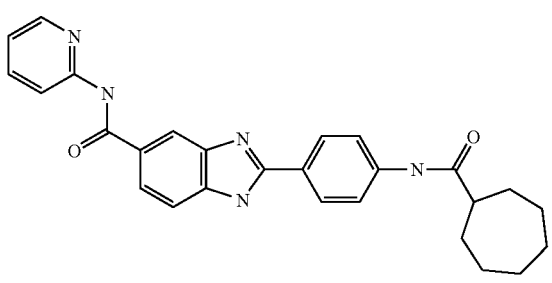
I.161
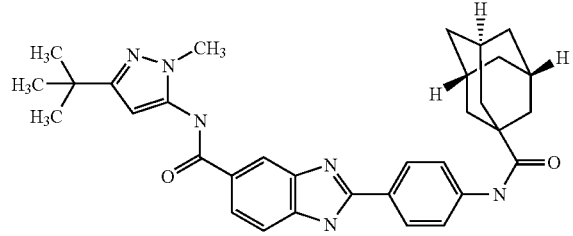
I.166
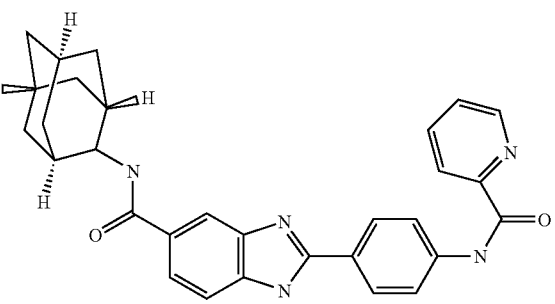
I.162
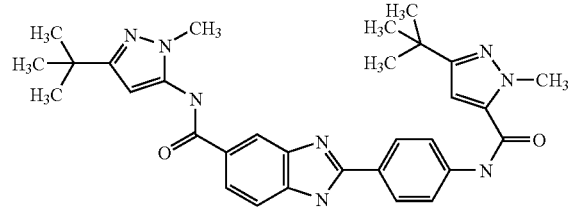
I.167
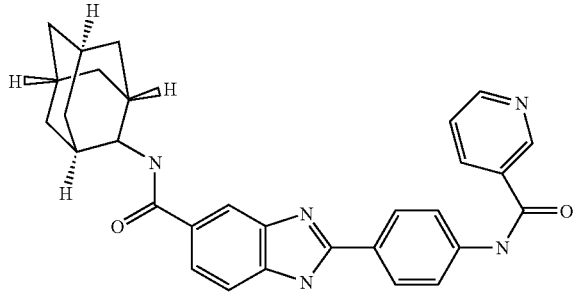

-continued
I.168
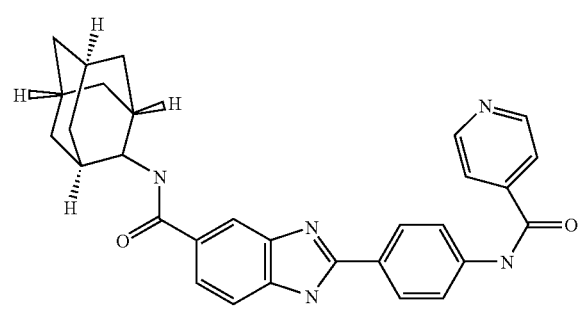
I.169
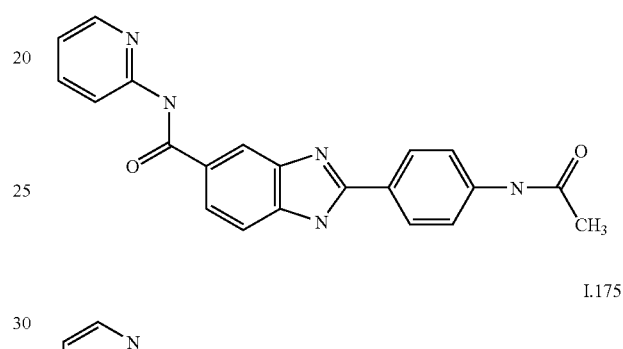
I.170
I.171
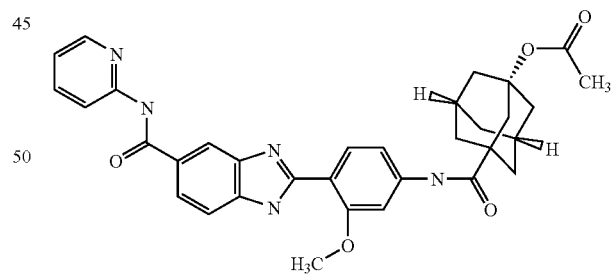
I.172
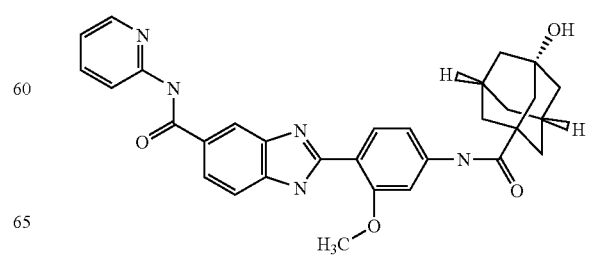
-continued
I.173
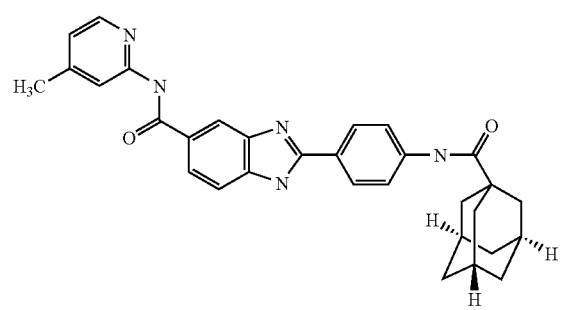
I.174
I.175
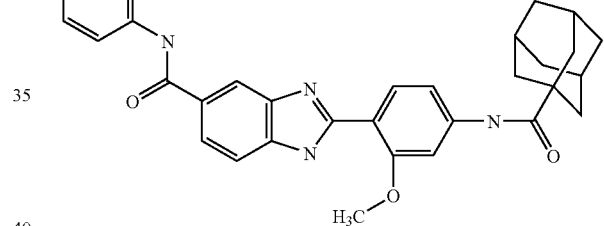
I.176
lp;1p
I.177

-continued
I.178
I.179
I.180
I.181
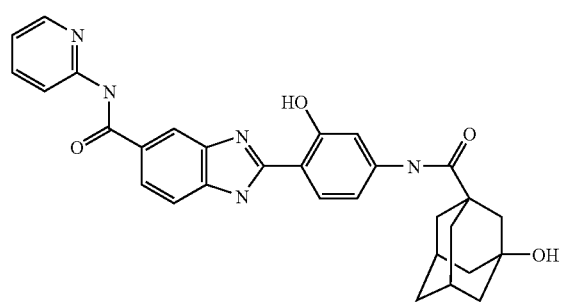
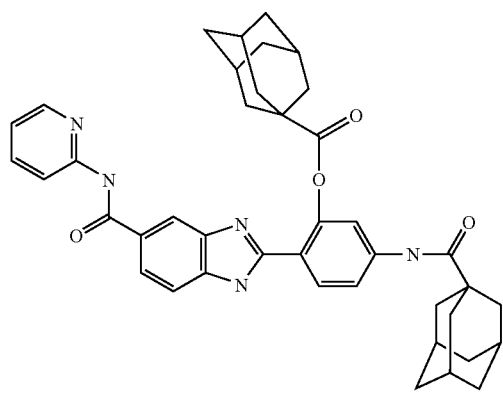
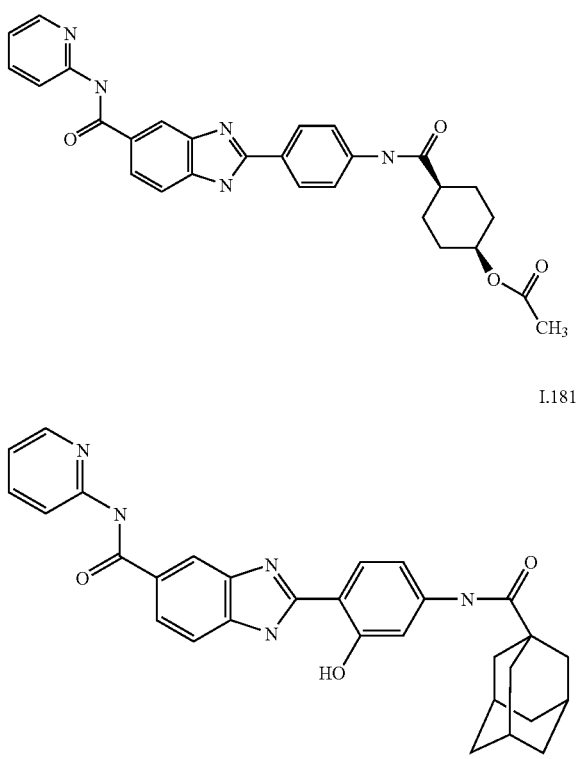
-continued
I.182
I.183
I.184
I.185
I.186
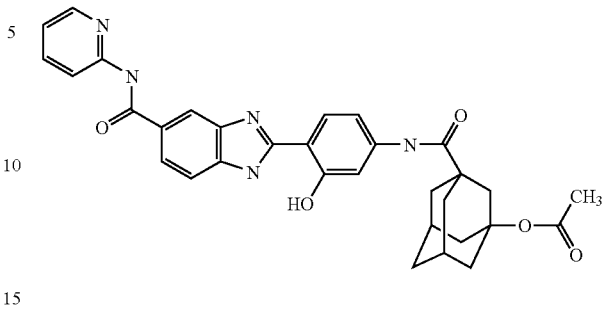

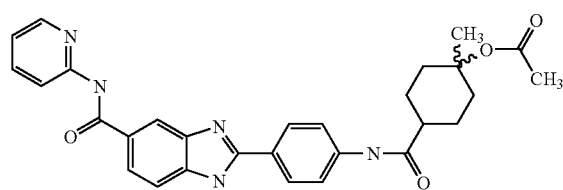
I.187
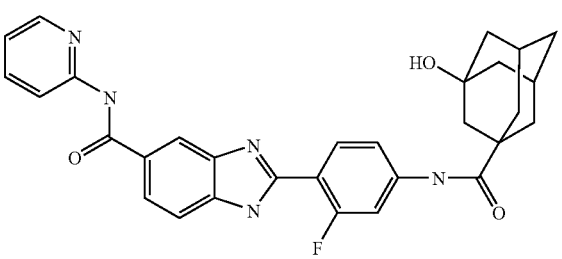
I.190
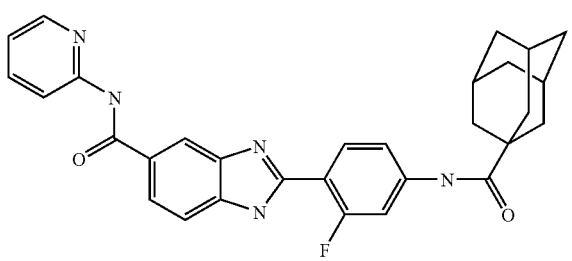
I.188
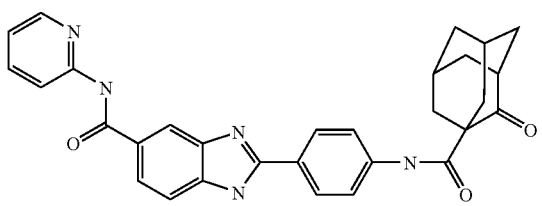
I.191
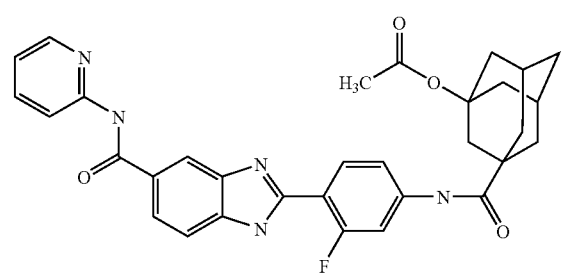
I.189
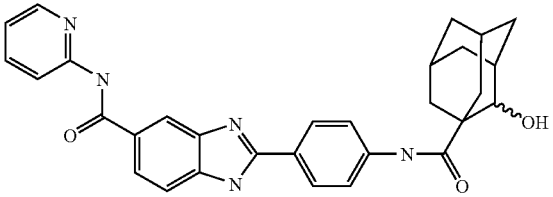
I.192
Compounds of Genus I may be synthesized by any conventional reactions known in the art. Examples of syntheses include the following reactions, designated Synthetic Scheme I:
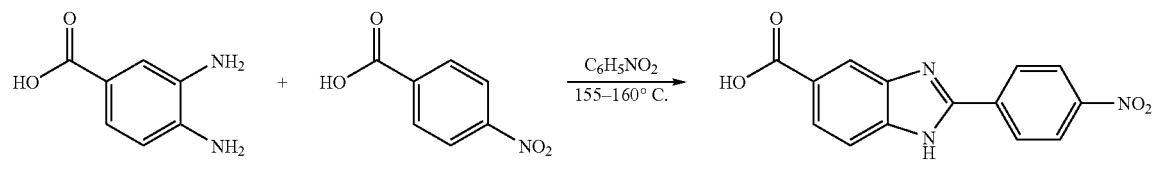
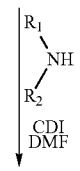

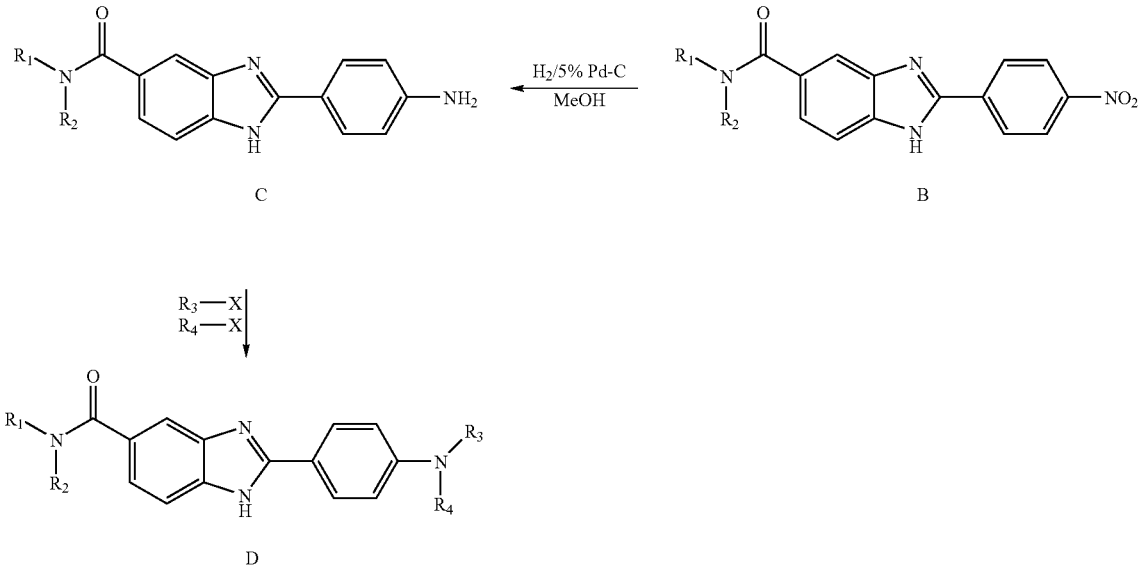

Synthesis of the Compounds of Genus 1

Synthetic Scheme I shows one method that can be used to prepare the compounds of Genus I. One skilled in the art will appreciate that a number of different synthetic reaction schemes may be used to synthesize the compounds of Genus I. Further, one skilled in the art will understand that a number of different solvents, coupling agents and reaction conditions can be used in the syntheses reactions to yield comparable results.

In step one, compound A or salt thereof is prepared from a cyclocondensation reaction of 3,4-diaminobenzoic acid or salt thereof and 4-nitrobenzaldehyde. The cyclocondensation reaction may be prepared in a solvent with heat. An example of the solvent is nitrobenzene. The temperature of the cyclocondensation reaction is from about 100° C. to about 200° C., preferably about 155° C. to about 160° C. The same compound can be prepared by a two-step process, as follows: reacting the diamine with p-nitrobenzoyl chloride in the presence of a base such as tri-ethylamine, DIEP, DMAP, or pyridine, or other such base; and, cyclizing the resulting amide (by elimination of a mole of water) with PPA, $H_2SO_4$ or other dehydrating agents at an ambient temperature to generate the benzimidazole ring.

In step 2, compound A or salt thereof is treated with ammonia or amine to obtain compound B or salt thereof. The amide formation reaction may occur in the presence of a coupling agent, or by converting it to an acid chloride and then reacting it with an amine (such as aromatic amines, aliphatic amines, heterocyclic amines and the like) in a solvent in presence of another base to absorb the acid produced. This can be carried out with or without heating. An example of the coupling agent is 1,1'-carbonyldiimidazole (CDI), EDC, and other similar coupling agents. An example of the solvent is N,N-dimethylformamide (DMF), THF, pyridine, triethylamine or mixed solvent system such as DMF and THF, and the like.

In step 3, compound B or salt thereof can undergo reduction to yield compound C or salt thereof. The reduction may be accomplished by catalytic hydrogenation in the presence of a catalyst in a solvent system. The catalysts are Pd, Ni, Pt, and the like. An example of the agent used for catalytic hydrogenation is hydrogen in the presence of 5% Pd—C. The reduction can occur in a hydroxylic solvent, such as methanol or ethanol, or a mixed solvent system such as DMF-MeOH, or in acetic acid, or in the presence of some acid in a hydroxylic solvent, and the like.

In step 4, compound C or salt thereof is alkylated or acylated at the amine by treatment with the appropriate reagents. In Synthetic Scheme I, compound C is shown to react with $R_3$—X and $R_4$—X to alkylate or acylate the amine. It is understood that $R_3$ and $R_4$ are groups that alkylate the amine and X is a leaving group. The amino group can be acylated with reagents, such as acyl halides, anhydrides, carboxylic acid, carboxylic esters, or amides. The amino group can be alkylated with alkyl halides in the presence of a base, preferably for the production of a tertiary or hindered amine and the like. An alternative method to alkylating the amino group is to reductive aminate. In a reductive amination, the amine condenses with an aldehyde or ketone to give an imine. Subsequently, the imine is reduced to yield an alkylated amine. In a reductive amination, the $R_3$ and $R_4$ groups may not have leaving groups upon reaction with the amine. Still another alternative method is reaction of the amine with a diazo compound. The acidity of amines is not great enough for the reaction to proceed without a catalyst, but $BF_3$, which converts the amine to a complex, enables the reaction to take place. Cuprous cyanide can also be used as a catalyst.

Compound D is representative of the compounds in Genus I.

One skilled in the art will appreciate variations in the sequence and further, will recognize variations in the appropriate reaction conditions from the analogous reactions shown or otherwise known which may be appropriately used in the processes above to make compounds of compounds A–D.

In the processes described herein for the preparation of compounds A–D of this invention, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds A–D described above are prepared by reacting the appropriate base or acid with a stoichiometric equivalent of the compounds of compounds A–D.

Compounds of Genus II

Another family of small molecule IgE inhibitors in accordance with the present invention include benzimidazole-2-benzamides, defined by the following genus (Genus II):

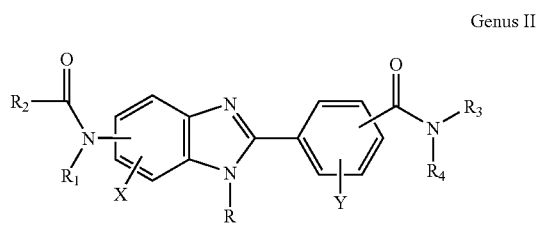

Genus II wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, OH, $OCH_3$, COOH, COOR' COR', CN, $CF_3$, $OCF_3$, $NO_2$, NR'R', NHCOR' and CONR'R';

wherein $R_3$ and $R_4$ are independently selected from the group consisting of H, alkyl, aryl, heteroaryl and COR';

wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein X and Y are independently selected from the group consisting of H, halogens, alkoxy, substituted alkoxy, alkyl, substituted alkyl, dialkylaminoalkyl, hydroxyalkyl, OH, $OCH_3$, COOH, CN, $CF_3$, $OCF_3$, $NO_2$, COOR", CHO and COR"; and wherein R" is a $C_1$–$C_8$ alkyl, wherein said $C_1$–$C_8$ alkyl is selected from the group consisting of a straight chain, branched or cyclic alkyl.

The following specific compounds are encompassed within the definition of Genus II:

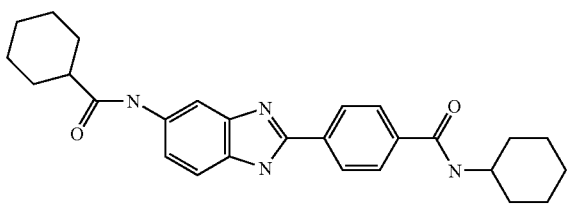

II.1

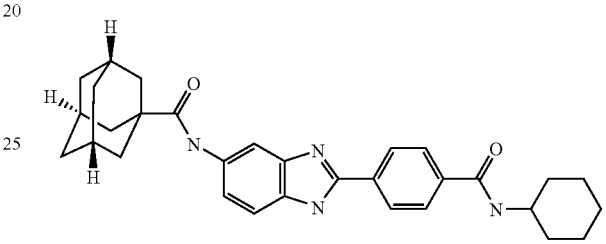

II.2

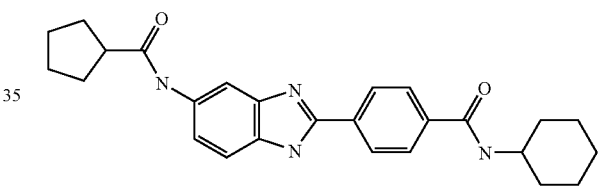

II.3

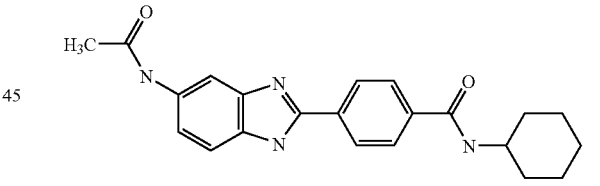

II.4

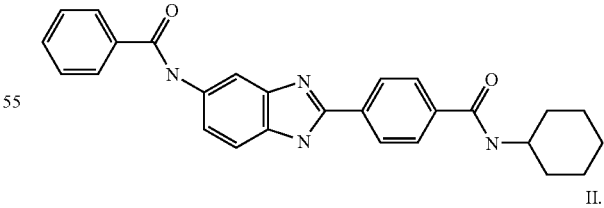

II.5

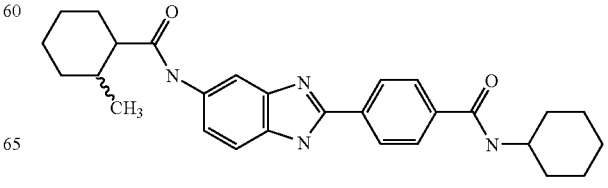

II.6

-continued
II.7
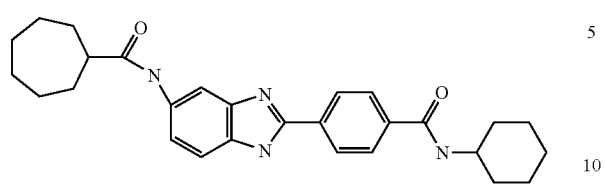
II.8
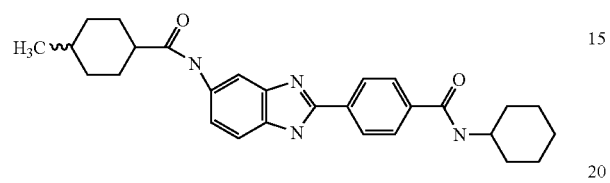
II.9
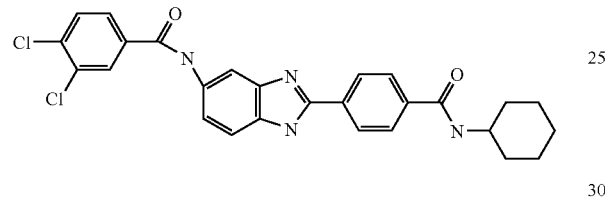
II.10
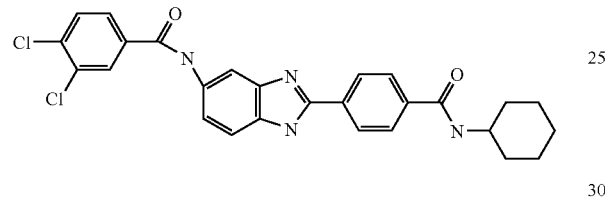
II.11
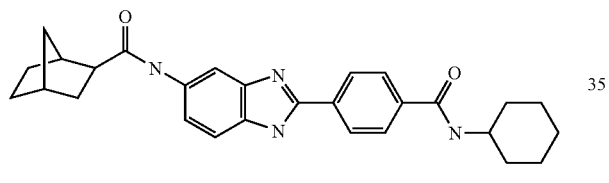
II.12
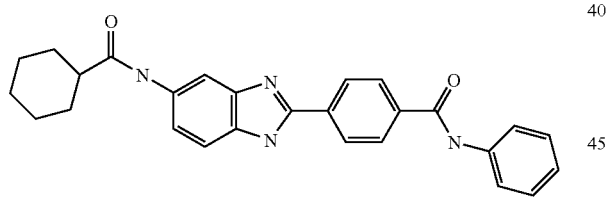
II.13
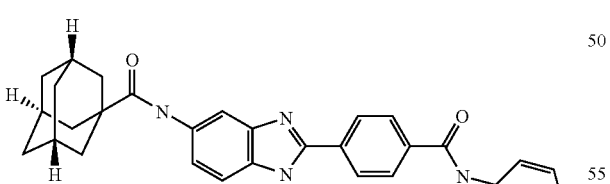
-continued
II.14
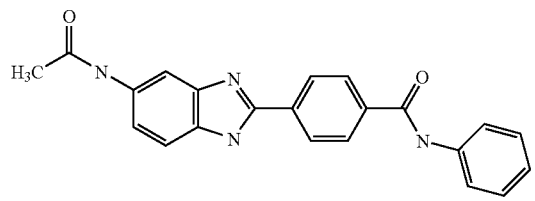
II.15
II.16
II.17
II.18
II.19

-continued
II.20
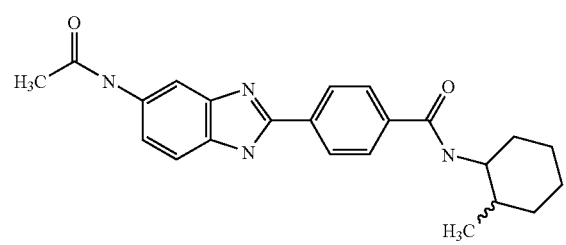
II.21
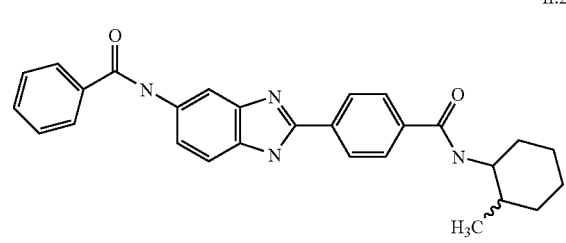
II.22
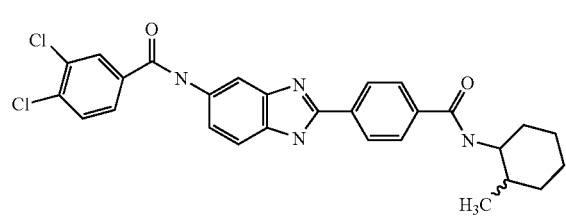
II.23
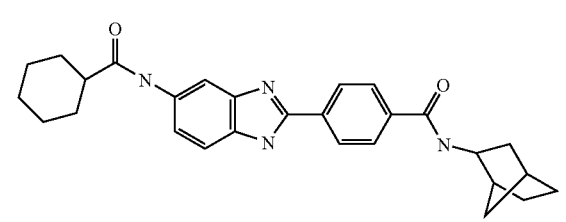
II.24
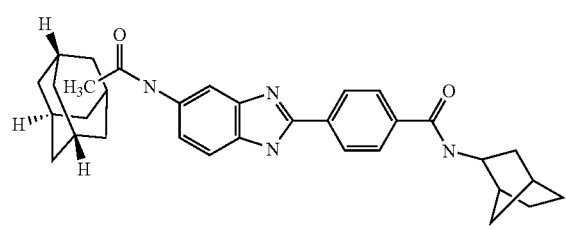
II.25
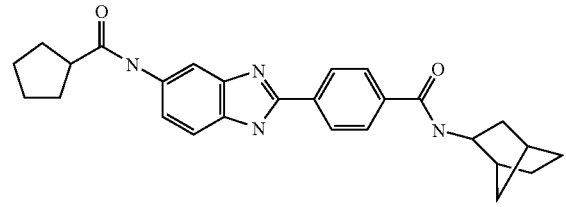
-continued
II.26
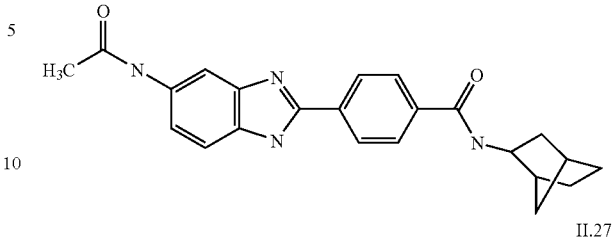
II.27
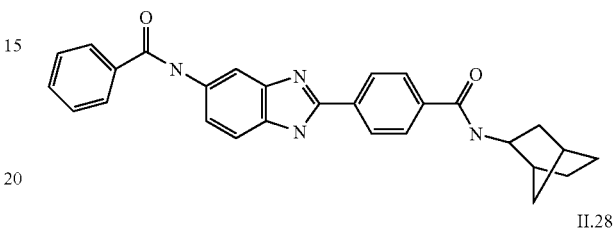
II.28
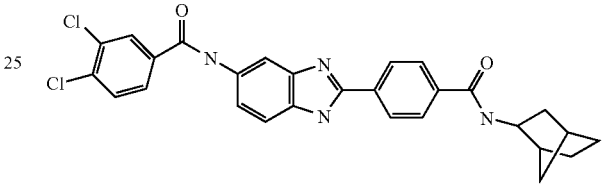
II.29
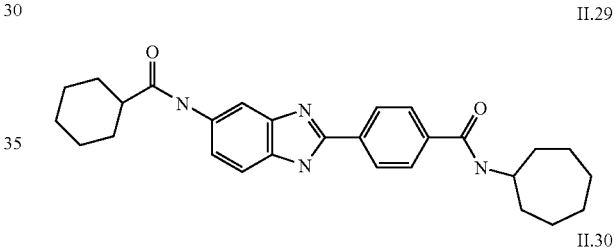
II.30
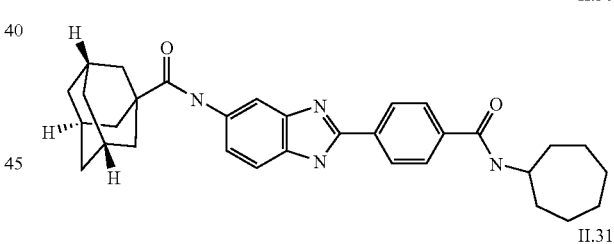
II.31
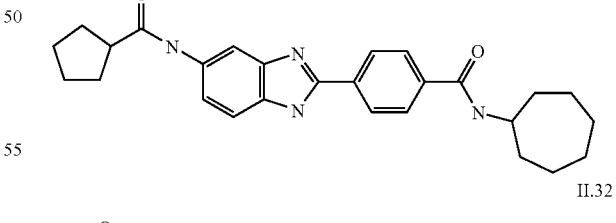
II.32
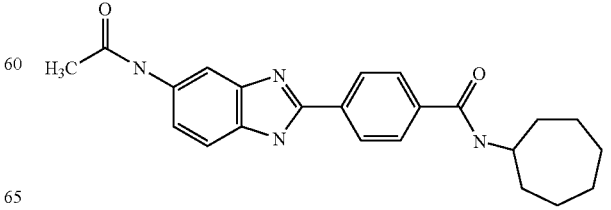

II.33
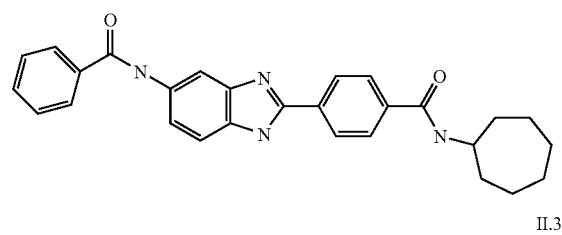
II.34
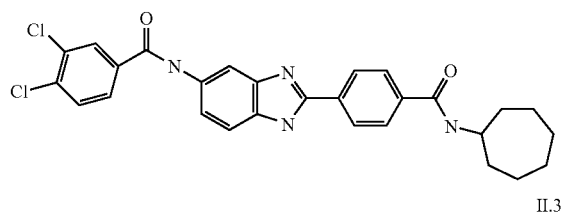
II.35
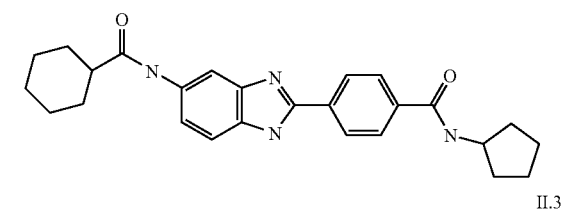
II.36
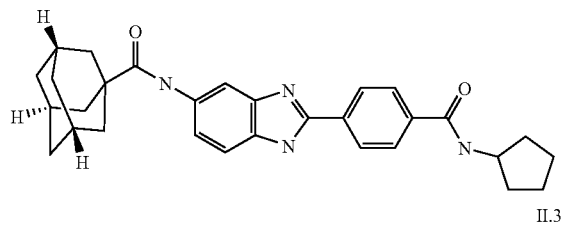
II.37
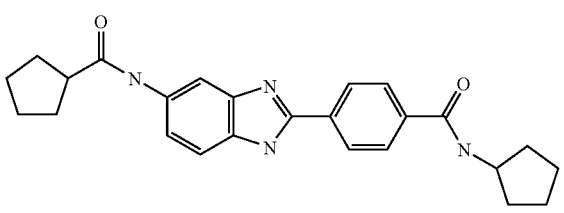
II.38
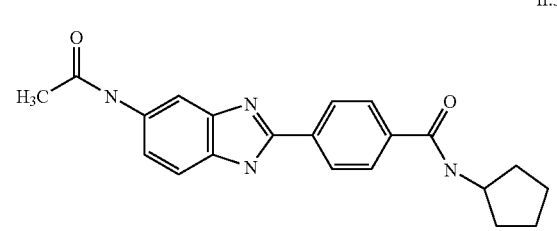
II.39
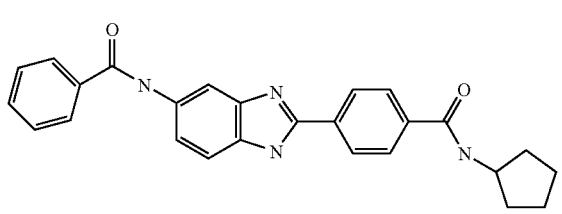
II.40
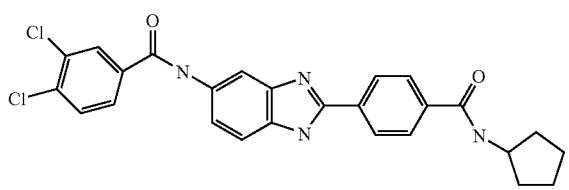
II.41
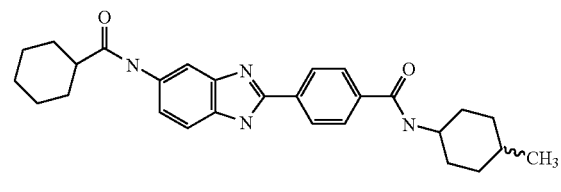
II.42
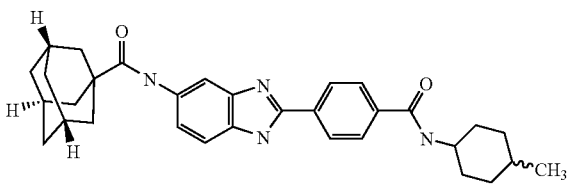
II.43
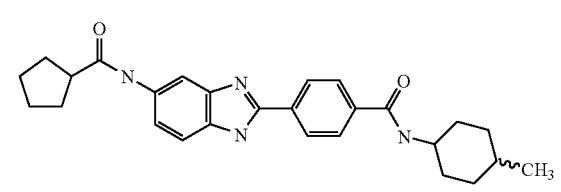
II.44
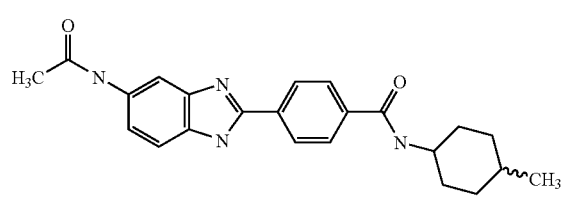
II.45
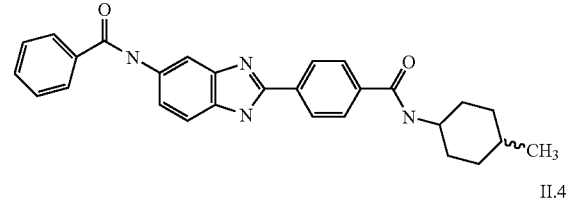
II.46
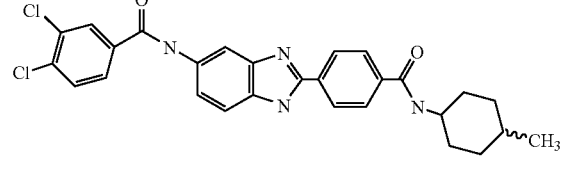

II.47
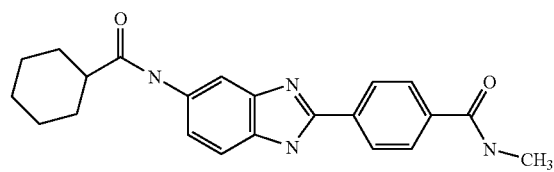
II.48
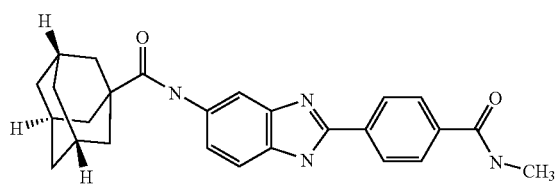
II.49
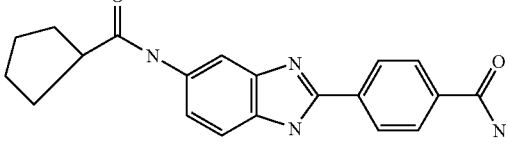
II.50
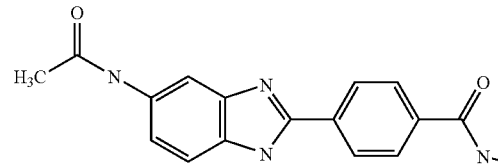
II.51
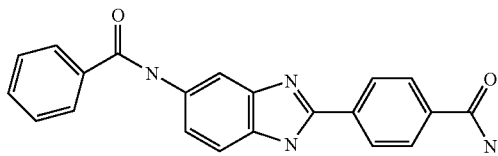
II.52
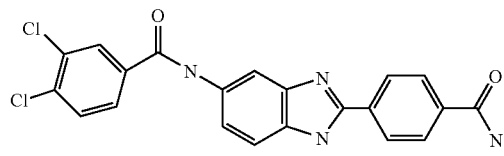
II.53
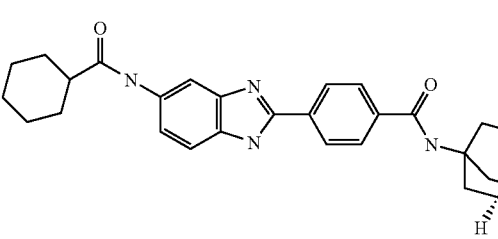
II.54
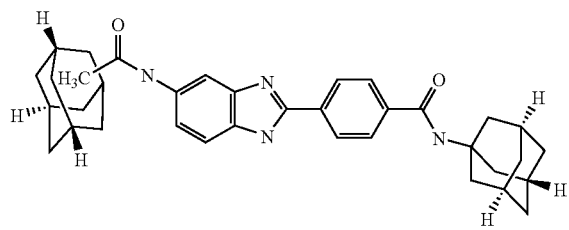
II.55
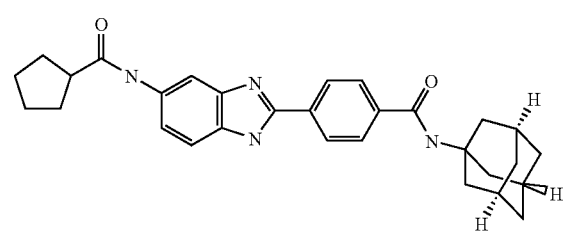
II.56
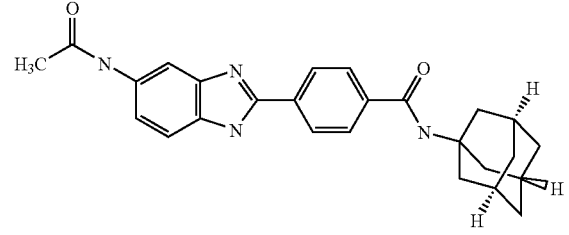
II.57
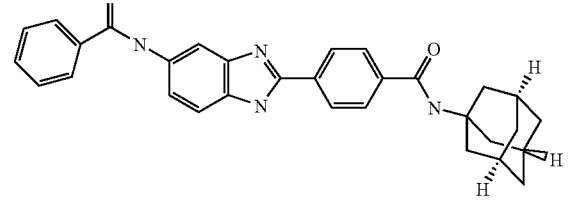
II.58
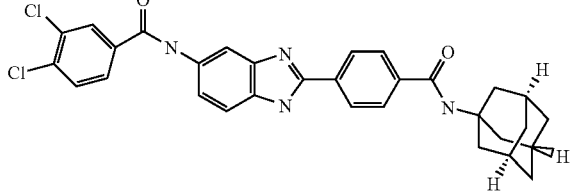
II.59

II.60
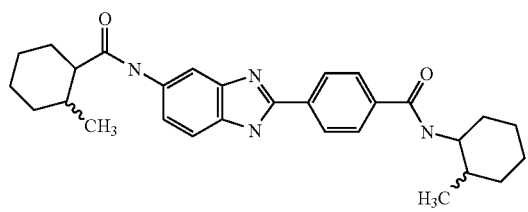
II.61
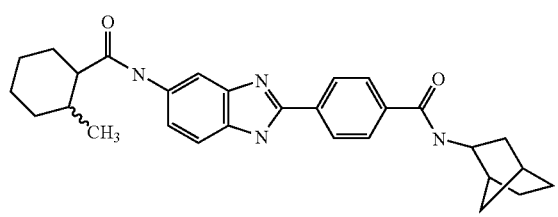
II.62
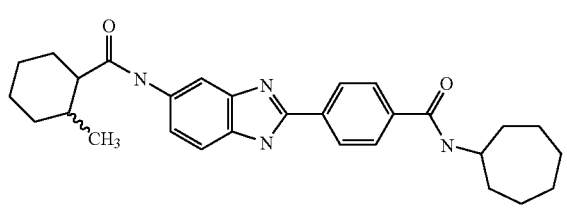
II.63
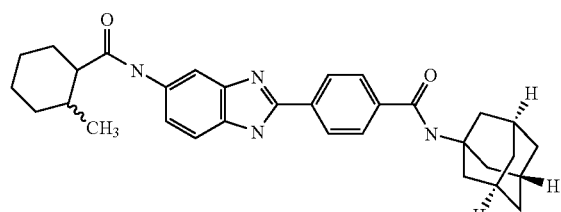
II.64
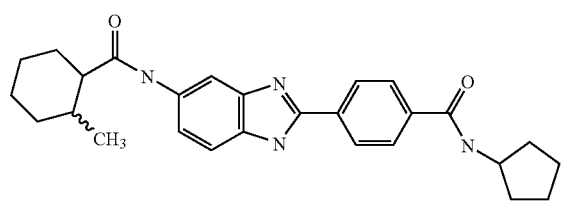
II.65
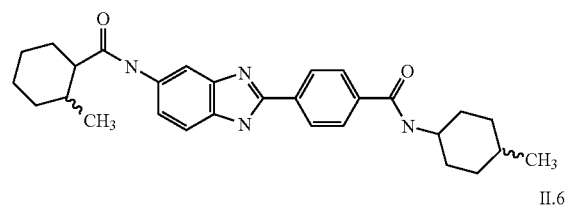
II.66
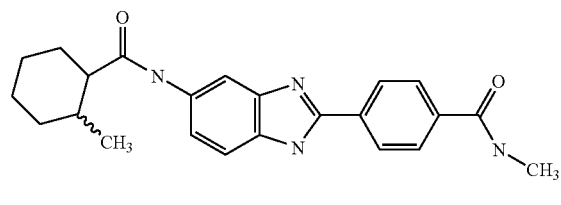
II.67
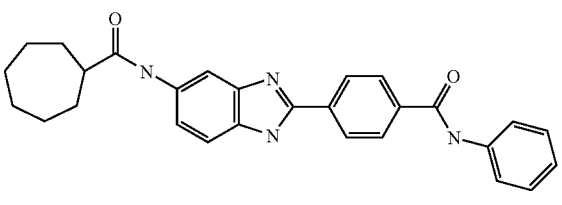
II.68
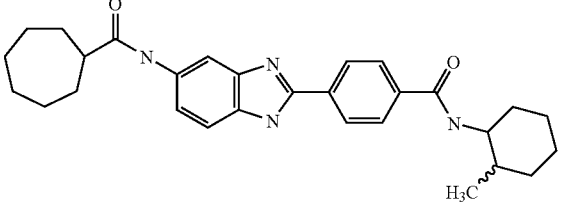
II.69
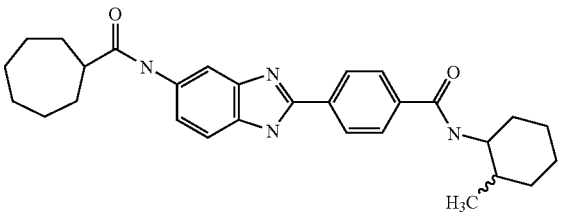
II.70
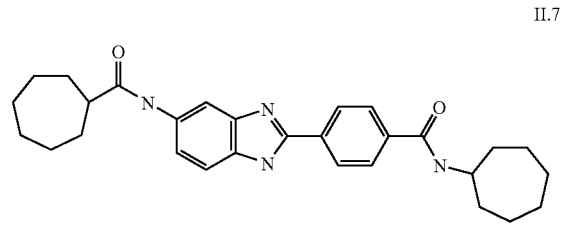
II.71
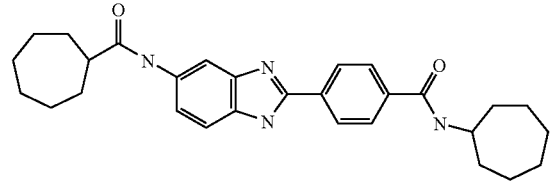
II.72
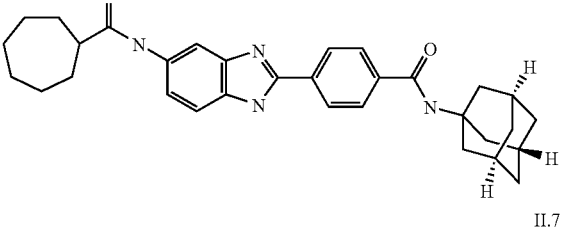
II.73
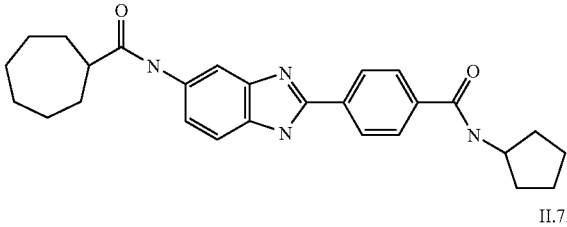
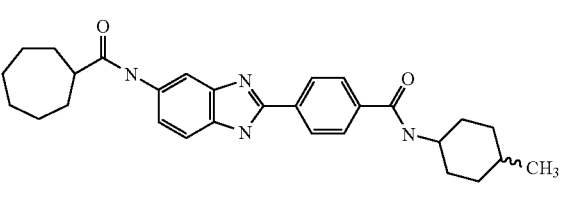

-continued
II.74
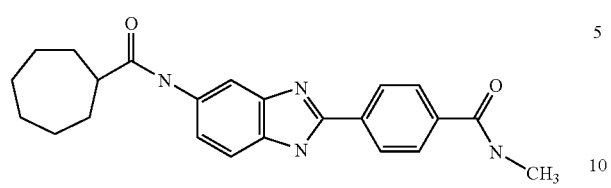
II.75
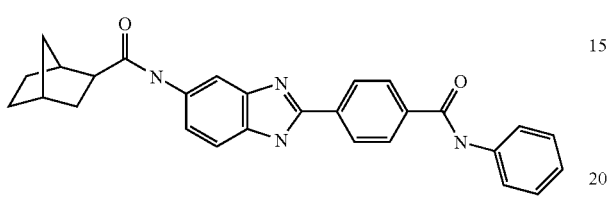
II.76
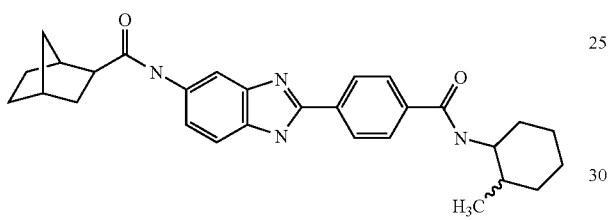
II.77
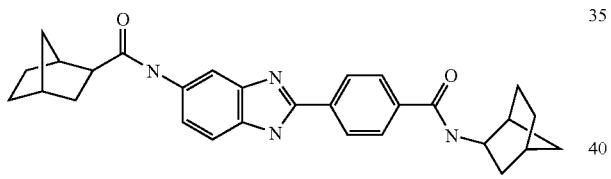
II.78
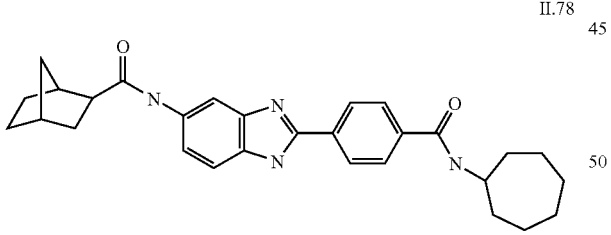
II.79
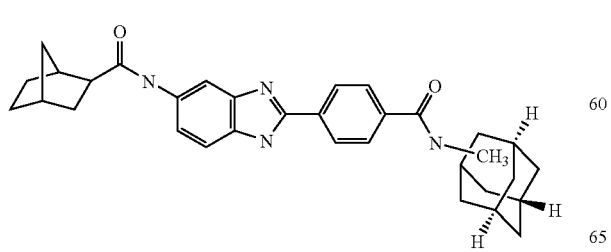
-continued
II.80
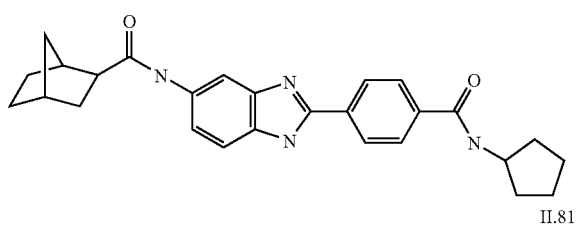
II.81
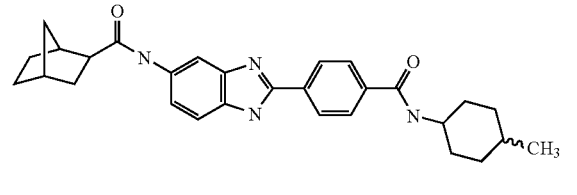
II.82
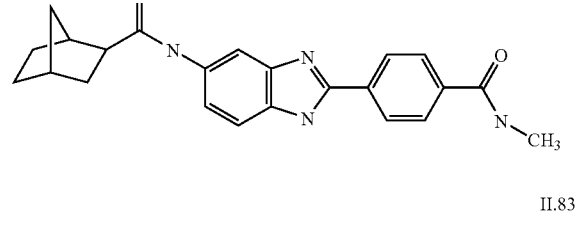
II.83
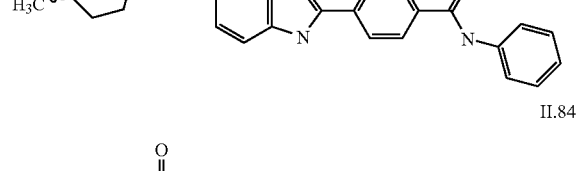
II.84
II.85
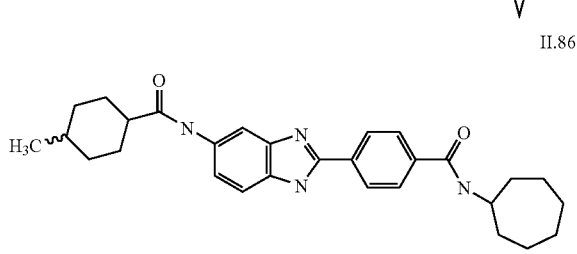

63
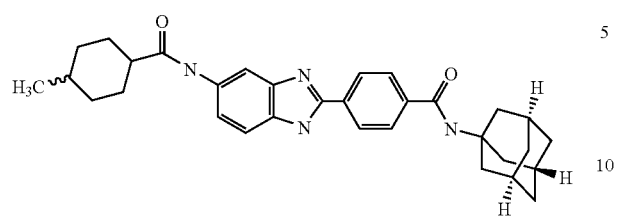
II.87
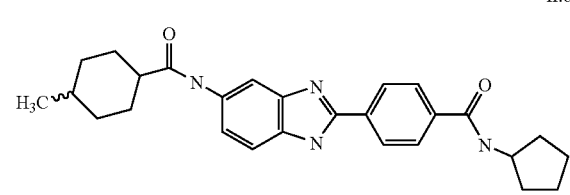
II.88
64
II.89
II.90
Compounds of Genus II may be synthesized by any conventional reactions known in the art. Examples of syntheses include the following reactions, designated Synthetic Scheme II:
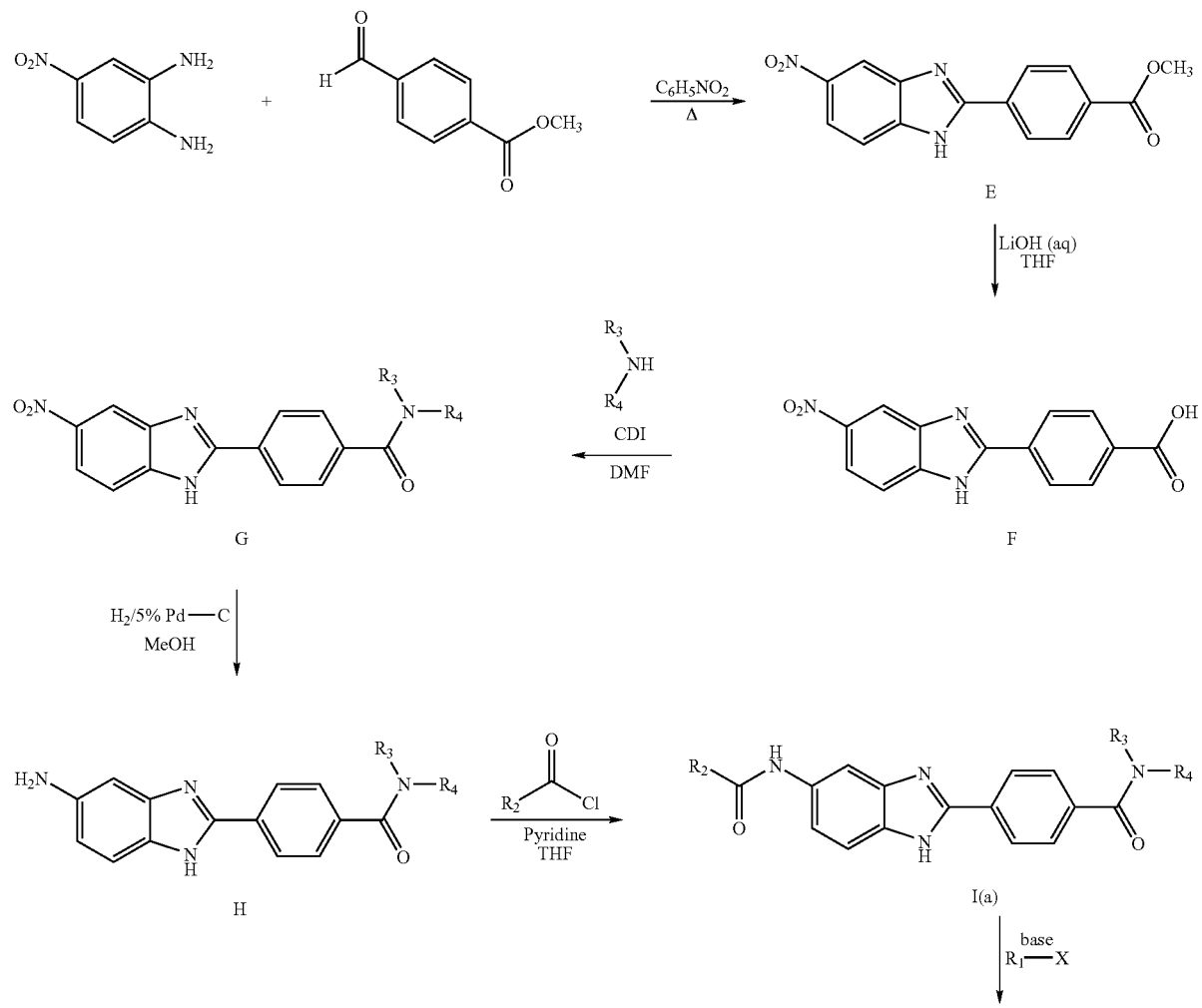
Synthetic Scheme II

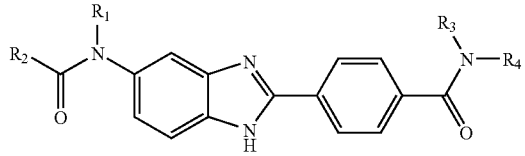

I(b)

Synthesis of the Compounds of Genus II

Synthetic Scheme II shows one method that can be used to prepare the compounds of Genus II. One skilled in the art will appreciate that a number of different syntheses reactions may be used to synthesize the compounds of Genus II. Further, one skilled in the art will understand that a number of different solvents, coupling agents and reaction conditions can be used in the syntheses reactions to yield comparable results.

In step one, compound E or salt thereof is prepared from a cyclocondensation reaction of 4-nitro-1,2-phenylenediamine or salt thereof and an alkyl (such as methyl 4-formylbenzoate) The cyclocondensation reaction may be carried out in a solvent with heat. Examples of solvents include nitrobenzene or other solvents with an oxidizing agent to convert imidazolines to imidazoles. The same compound can be prepared by a two-step process, as follows: reacting the diamine with p-carboalkoxy benzoyl chloride in presence of a base such as tri-ethylamine, DIEP, DMAP or pyridine or such other base; and, cyclizing the resulting amide (by elimination of a mole of water) with PPA, $H_2SO_4$ or other dehydrating agents at an ambient temperature to generate the benzimidazole ring.

In step 2, compound E or salt thereof is treated with a base to hydrolyze the ester to the acid with a base such as a lithium hydroxide solution or an aqueous sodium hydroxide, and the like, thereby obtaining compound F or salt thereof. The deprotection reaction may occur in the presence of solvents such as water or alcohol such as methanol or ethanol, THF, and the like.

In step 3, compound F or salt thereof is treated with ammonia or an amine to obtain compound G or salt thereof. The amide formation reaction may occur in the presence of a coupling agent or by converting it to an acid chloride and then reacting it with an amine, such as aromatic amines, aliphatic amines, heterocyclic amines, and the like, in a solvent in the presence of another base to absorb the acid produced. This reaction can be carried out with or without heating. Examples of the coupling agent include 1,1'-carbonyldiimidazole (CDI), EDC and other similar coupling agents. Examples of solvents include N,N-dimethylformamide (DMF), THF, pyridine, triethylamine, or mixed solvent systems such as DMF and THF, and the like.

In step 4, compound G or salt thereof can undergo reduction to yield compound H or salt thereof. The reduction may be accomplished by catalytic hydrogenation, preferably in the presence of a catalyst in a solvent system. The catalysts are Pd, Ni, Pt, and the like. An example of the agent used for catalytic hydrogenation is hydrogen in the presence of 5% Pd—C. The reduction can occur in a hydroxylic solvent, such as methanol, ethanol, in a mixed solvent system, such as DMF-MeOH, in acetic acid, or in the presence of some acid in a hydroxylic solvent, and the like.

In step 5, compound H or salt thereof is treated with an acyl halide to obtain compound I or salt thereof. The acylation reaction may occur in the presence of a base, such as tri-ethylamine, DIEP, DMAP or pyridine, and the like, in a solvent such as THF, DMF or Et3N, pyridine, and the like. The reaction may occur with or without heating. One specific example of the base is pyridine. One specific example of the solvent is tetrahydrofuran (THF).

If necessary, in step 6, compound I or salt thereof is treated with an alkyl halide in the presence of a base to perform N-alkylation of the amide. Secondary amides can be alkylated by the use of a base, such a sodium hydride, for proton abstraction, followed by reaction with an alkyl halide. This reaction can be run in a convention solvent system or under phase transfer conditions. Amides can also be alkylated with diazo compounds. In another method, N-alkyl amides can also be prepared starting from alcohols by treatment of the latter with equimolar amounts of the amide, $Ph_3P$, and diethyl azodicarboxylate (EtOOCN=NCOOEt) at room temperature.

Compound I(b) is representative of the compounds in Genus II.

One skilled in the art will appreciate variations in the sequence and further, will recognize variations in the appropriate reaction conditions from the analogous reactions shown or otherwise known which may be appropriately used in the processes above to make compounds of compounds E–I(b).

In the processes described herein for the preparation of compounds E–I(b) of this invention, the requirements for protective groups are generally well-recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds E–I(b) described above are prepared by reacting the appropriate base or acid with a stoichiometric equivalent of the compounds of compounds E–I(b).

Compounds of Genus III

Another family of small molecule IgE inhibitors in accordance with the present invention include benzimidazole-bis-carboxamides, defined by the following genus (Genus III):

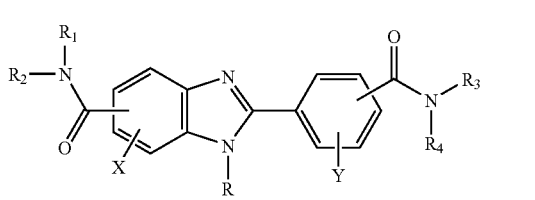

Genus III wherein R is selected from the group consisting of H, $C_1$–$C_5$ alkyl, benzyl, p-fluorobenzyl and di-alkylamino alkyl, wherein said $C_1$–$C_5$ alkyl is selected from the group consisting of a straight chain, branched or cyclic alkyl;

wherein $R_1$ and $R_2$ are independently selected from the group consisting of H, alkyl, substituted alkyl, $C_3$–$C_9$ cycloalkyl, substituted $C_3$–$C_9$ cycloalkyl, polycyclic aliphatic groups, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein said substituted phenyl, substituted naphthyl and substituted heteroaryl contain 1–3 substituents, wherein said substituent is selected from the group consisting of H, halogens, polyhalogens, alkoxy group, substituted alkoxy, alkyl, substituted alkyl, dialkylaminoalkyl, hydroxyalkyl, OH, $OCH_3$, COOH, COOR' COR', CN, $CF_3$, $OCF_3$, $NO_2$, NR'R', NHCOR' and CONR'R';

wherein $R_3$ and $R_4$ are independently selected from the group consisting of H, alkyl, aryl, heteroaryl and COR';

wherein R' is selected from the group consisting of H, alkyl, substituted alkyl, $C_3$–$C_9$ cycloalkyl, substituted $C_3$–$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1–3 heteroatoms, wherein said heteroatom is independently selected from the group consisting of nitrogen, oxygen and sulfur;

wherein X and Y are independently selected from the group consisting of H, halogens, alkoxy, substituted alkoxy, alkyl, substituted alkyl, dialkylaminoalkyl, hydroxyalkyl, OH, $OCH_3$, COOH, CN, $CF_3$, $OCF_3$, $NO_2$, COOR", CHO and COR"; and wherein R" is a $C_1$–$C_8$ alkyl, wherein said $C_1$–$C_8$ alkyl is selected from the group consisting of a straight chain, branched or cyclic alkyl.

The following specific compounds are encompassed within the definition of Genus III:

III.1

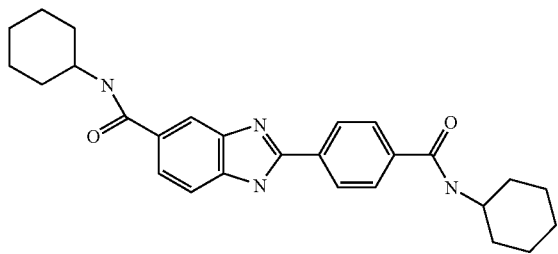

III.2

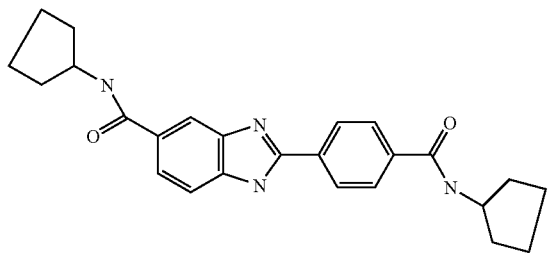

III.3

III.4

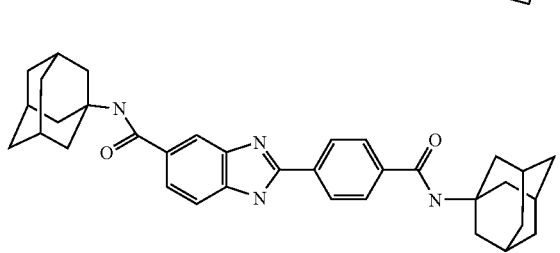

III.5

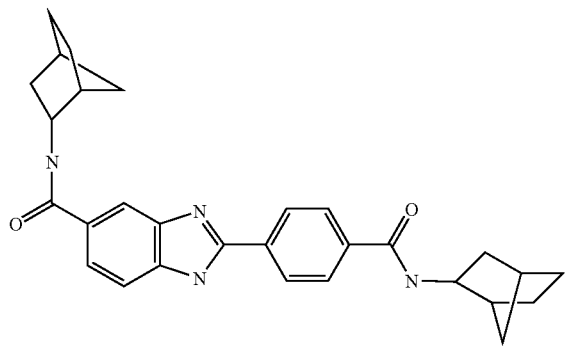

III.6

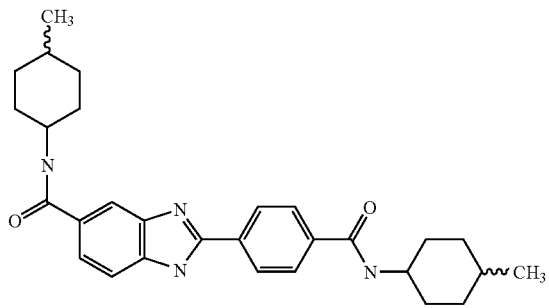

-continued
III.7
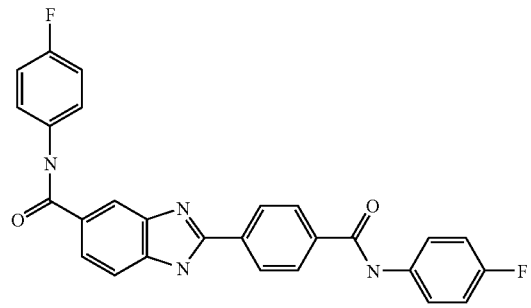
III.8
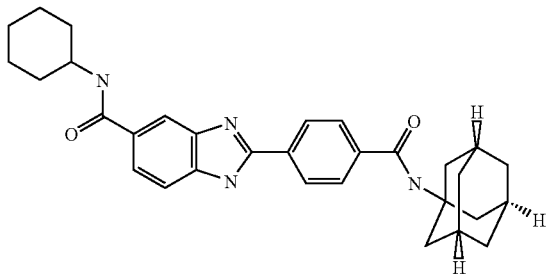
III.9
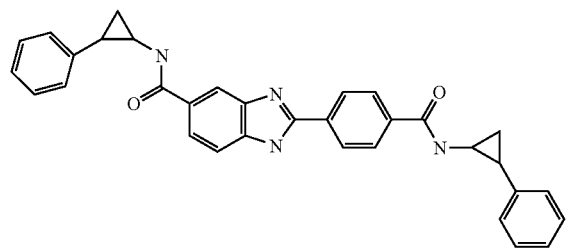
III.10
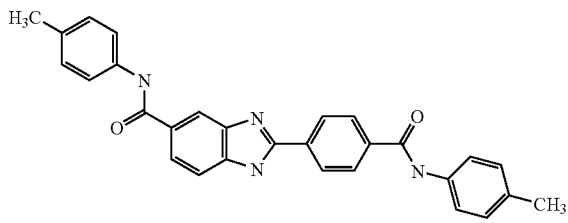
III.11
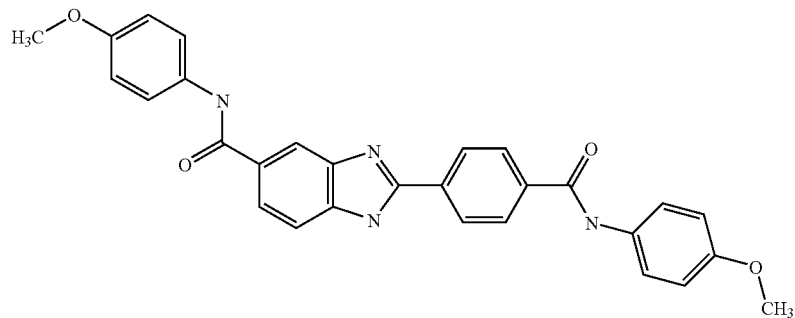
III.12
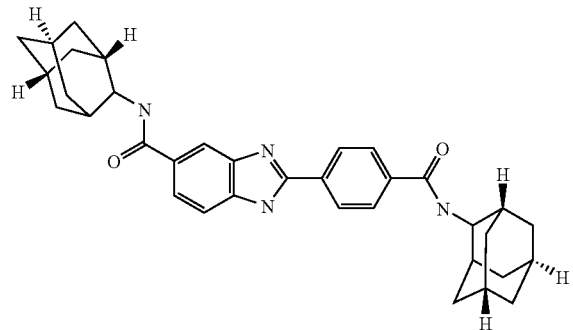
III.13
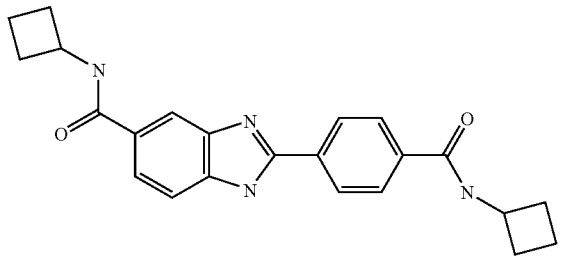

-continued
III.14
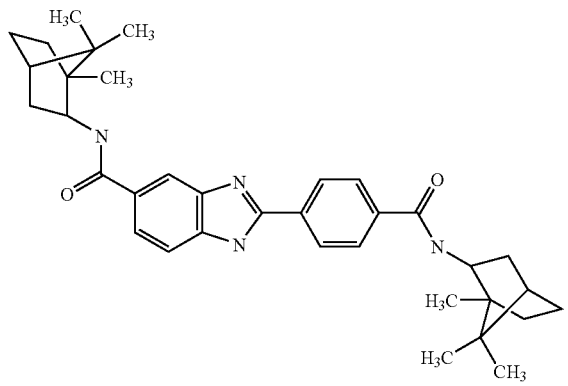
III.15
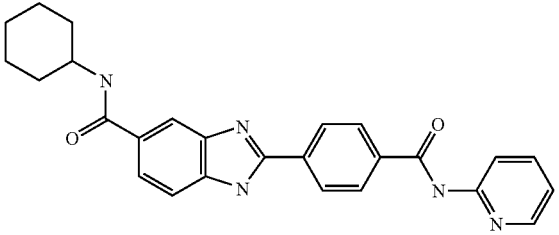
III.16
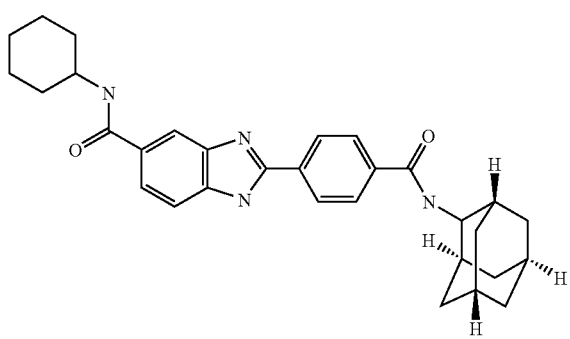
III.17
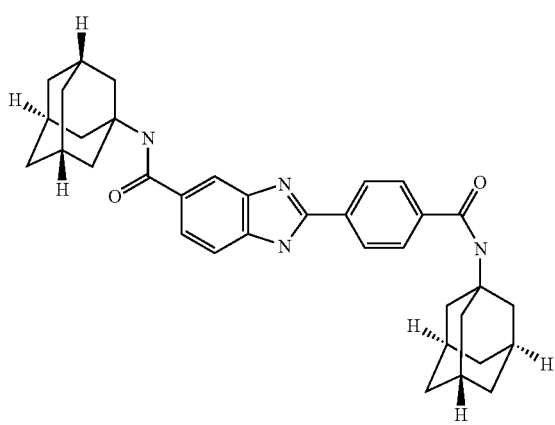
III.18
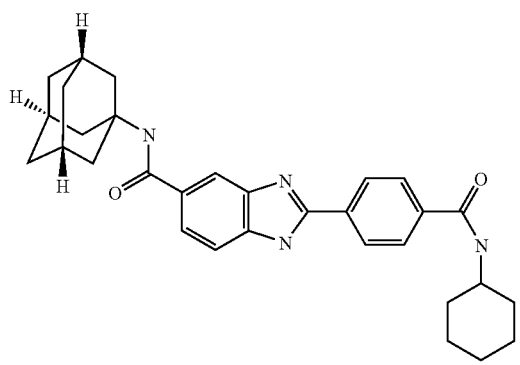
III.19
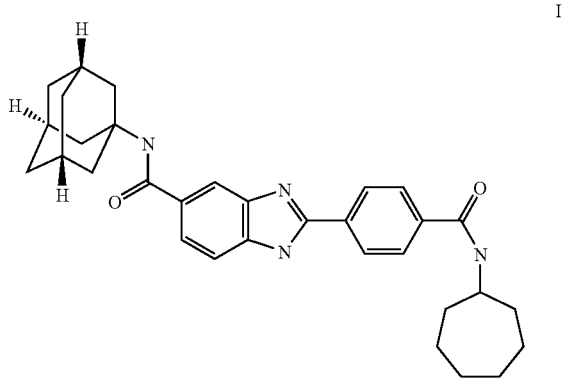
III.20
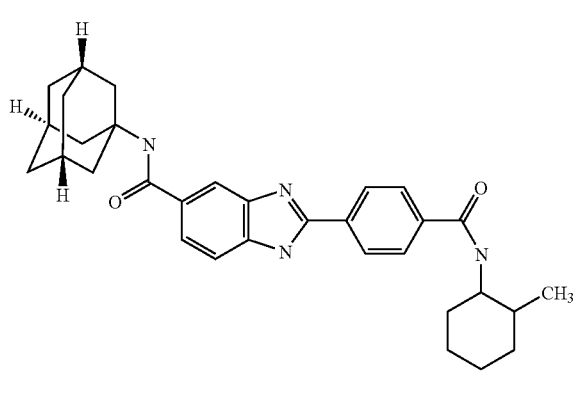
III.21
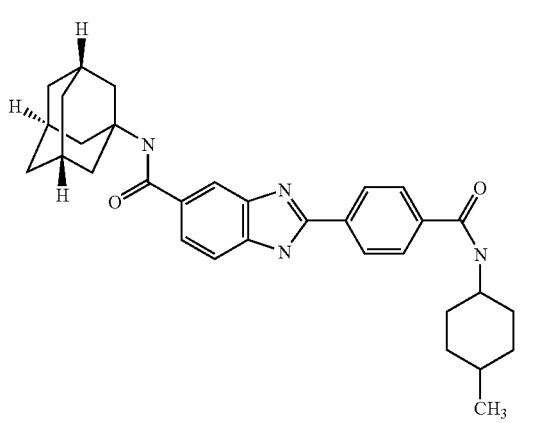

-continued
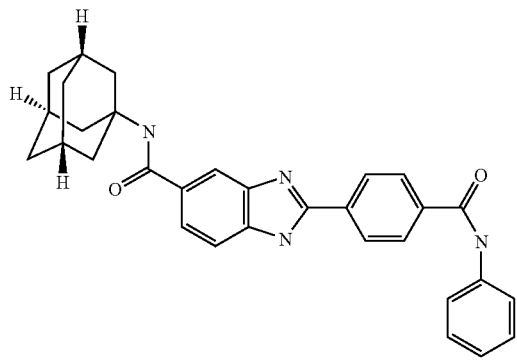
III.22
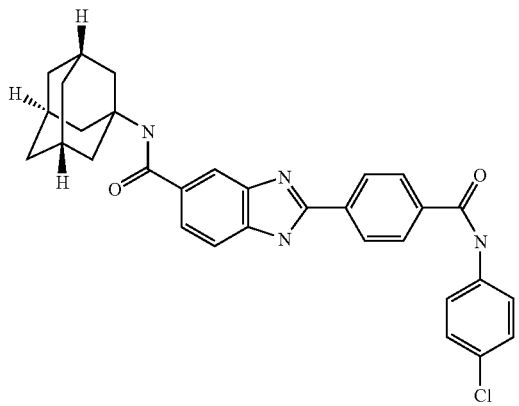
III.23
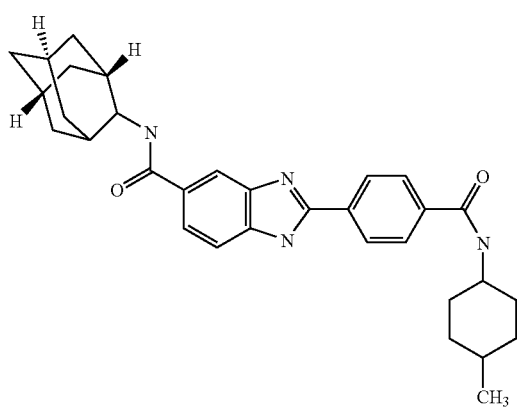
III.24
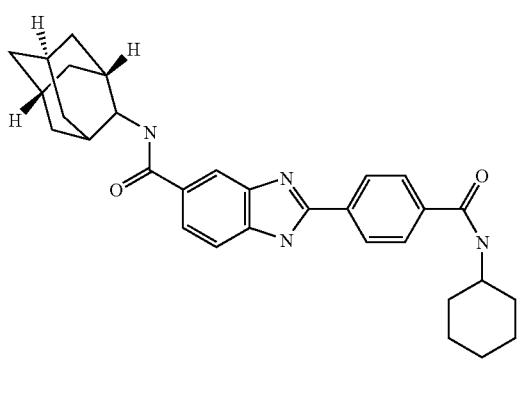
III.25
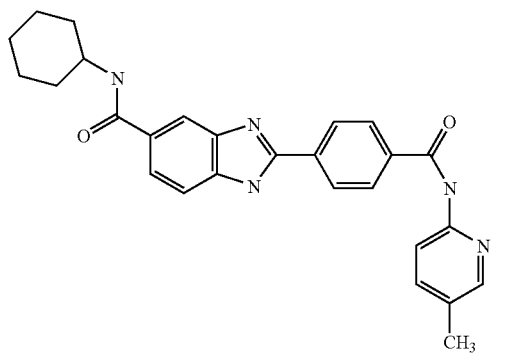
III.26
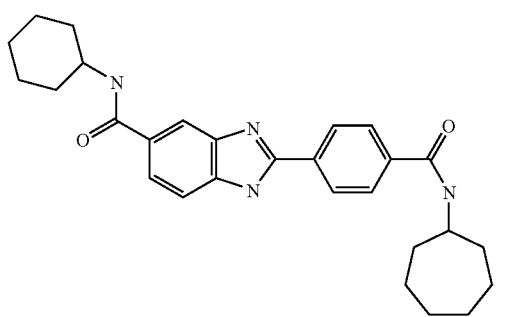
III.27
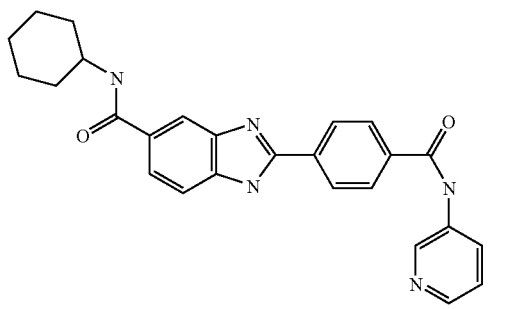
III.28
III.29

-continued
III.30
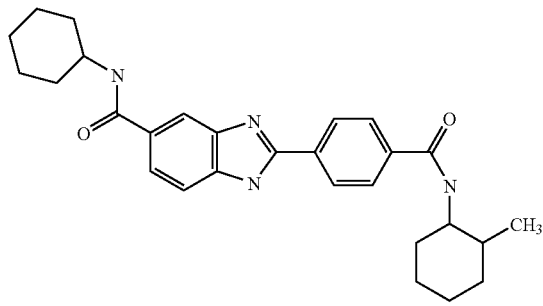
III.31
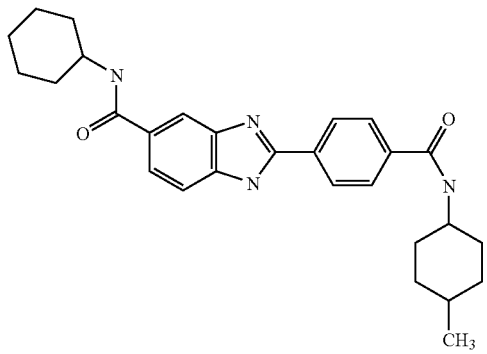
III.32
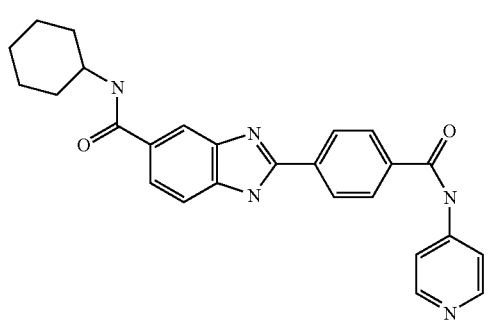
III.33
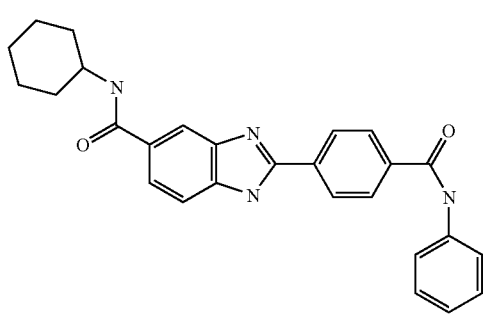
III.34
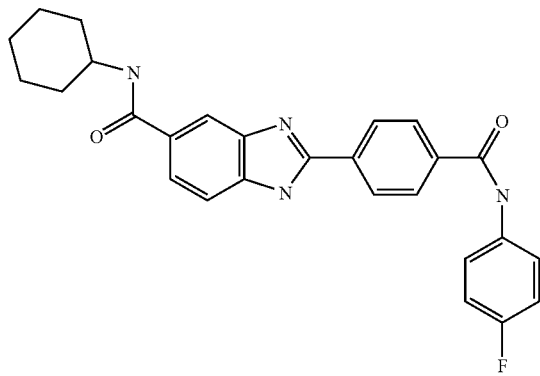
III.35
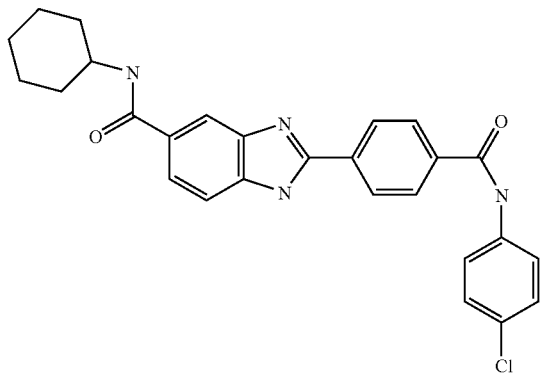
III.36
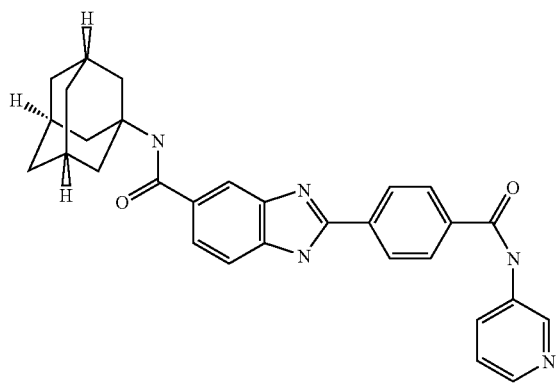
III.37
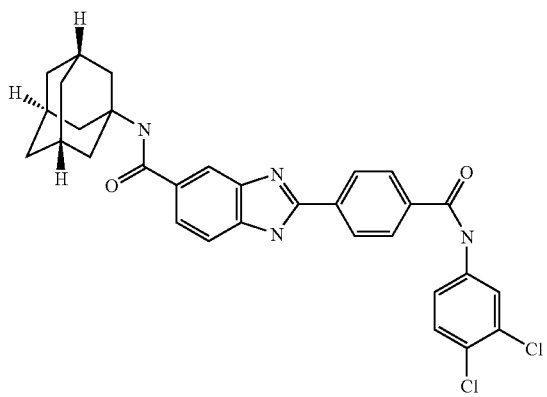

III.38
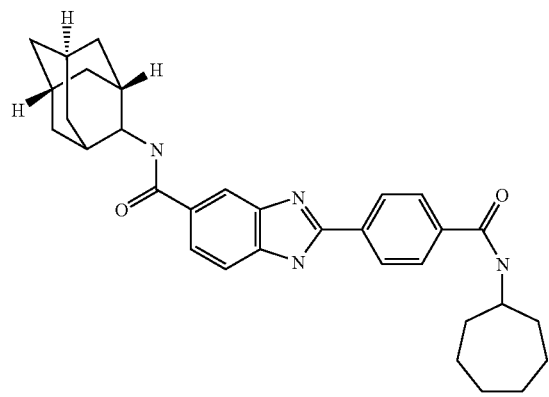
III.39
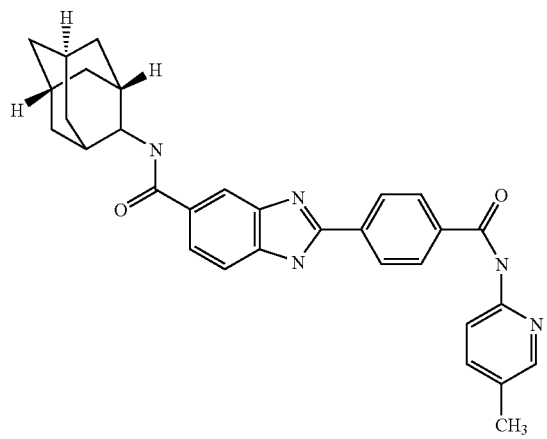
III.40
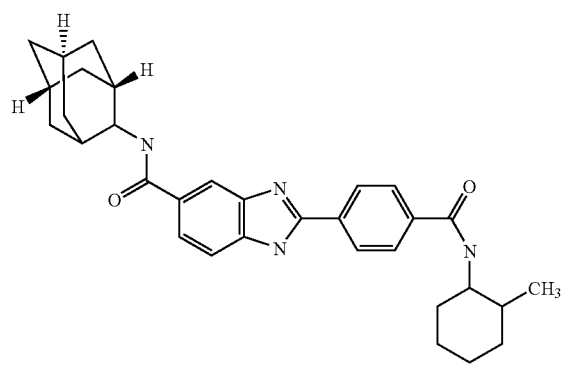
III.41
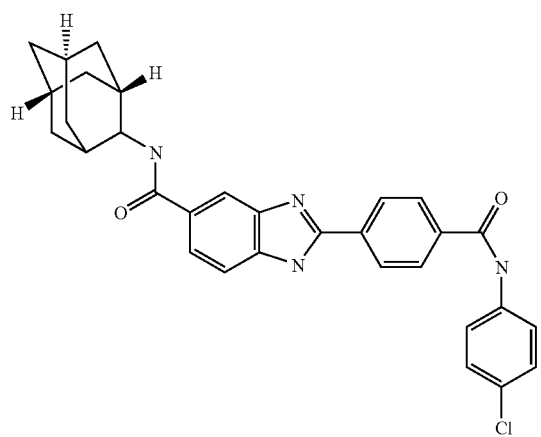
III.42
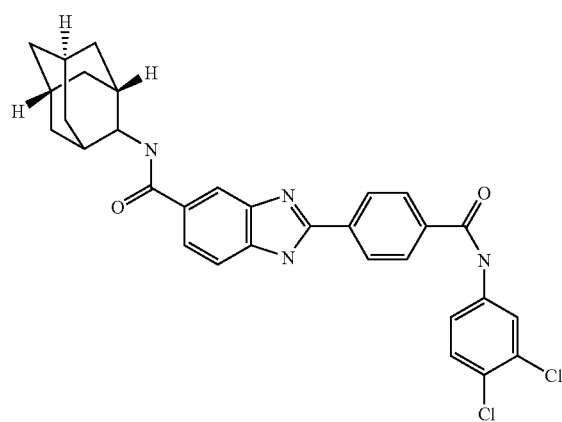
III.43
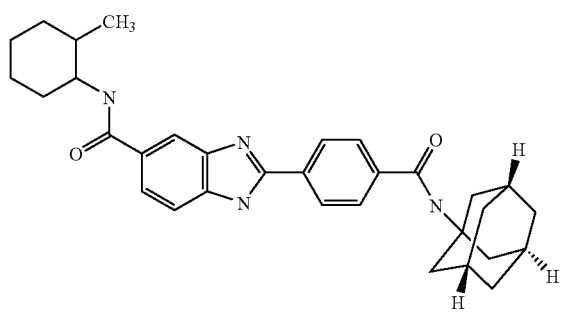

-continued
III.44
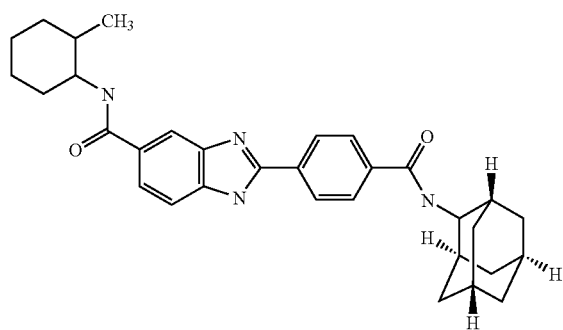
III.45
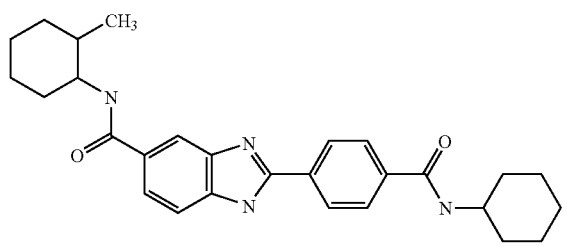
III.46
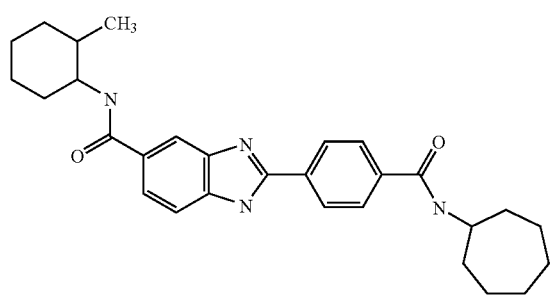
III.47
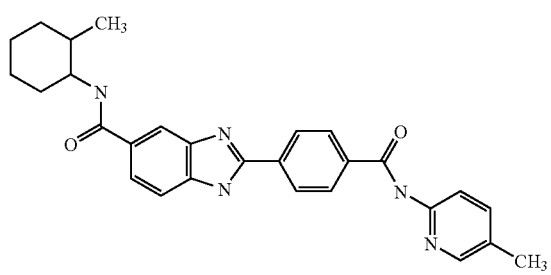
III.48
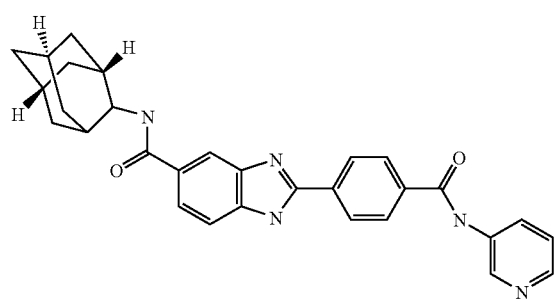
III.49
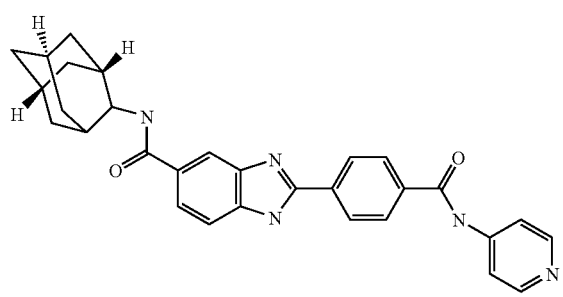
III.50
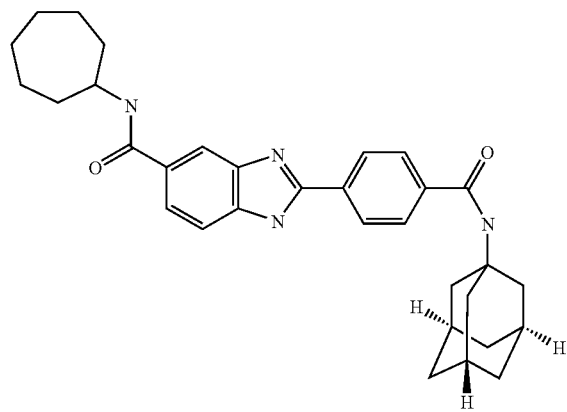
III.51
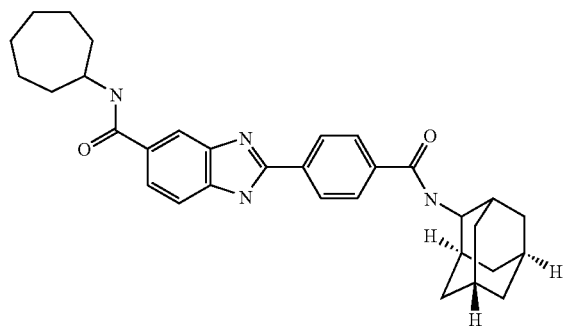

-continued
III.52
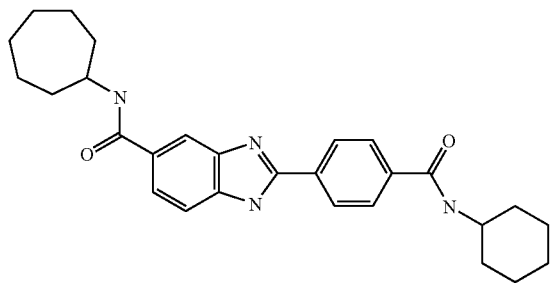
III.53
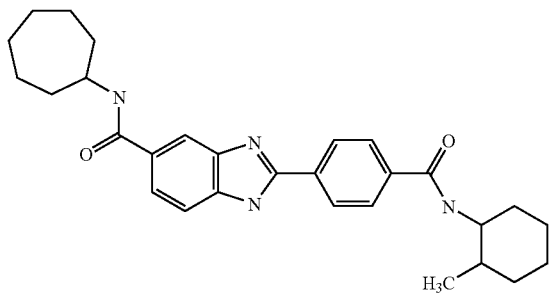
III.54
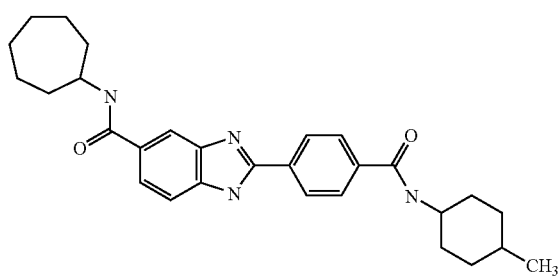
III.55
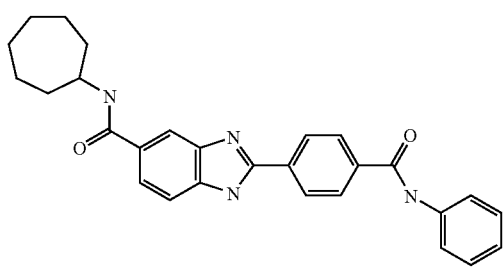
III.56
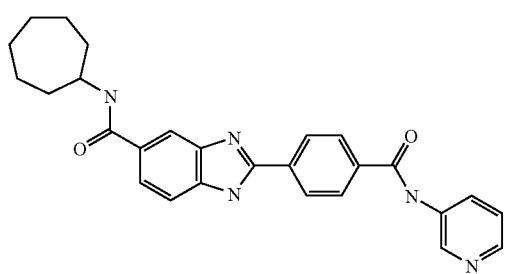
III.57
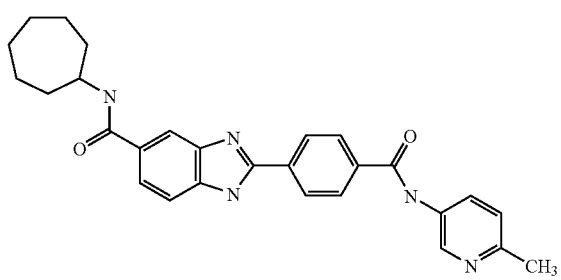
III.58
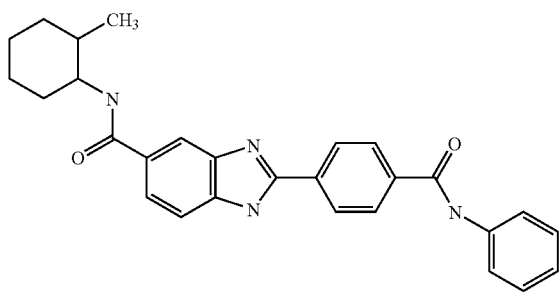
III.59
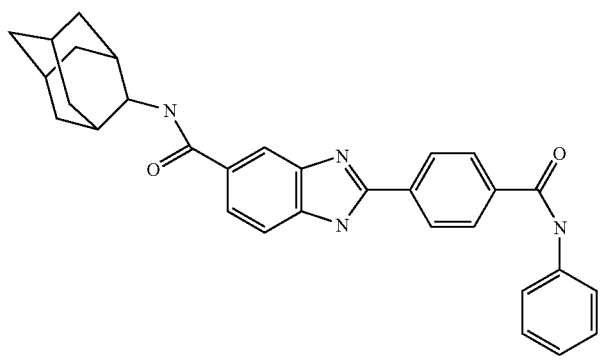

-continued
III.60
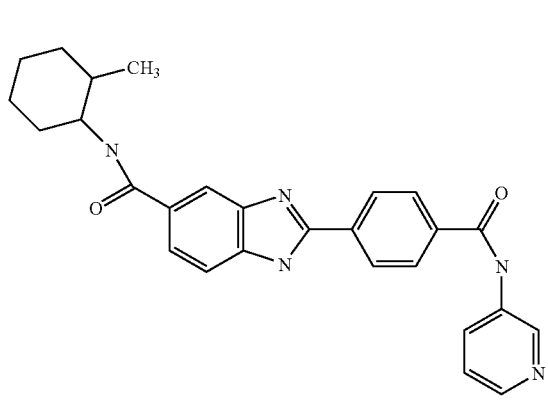
III.61
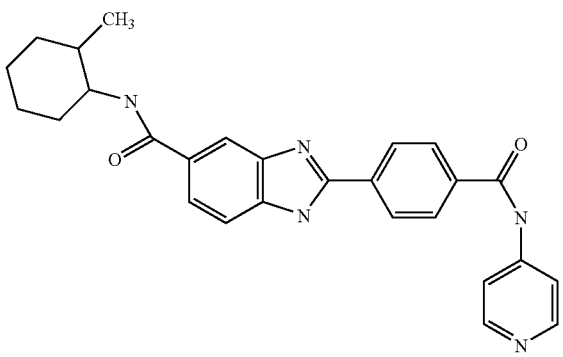
III.62
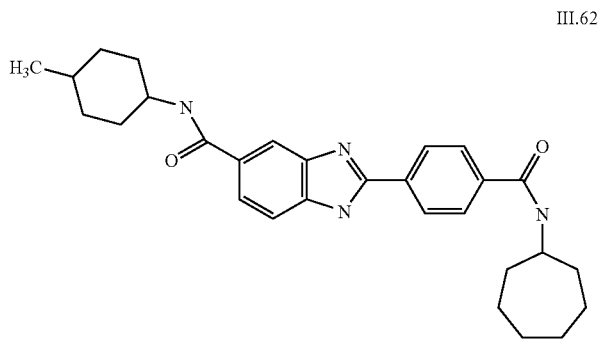
III.63
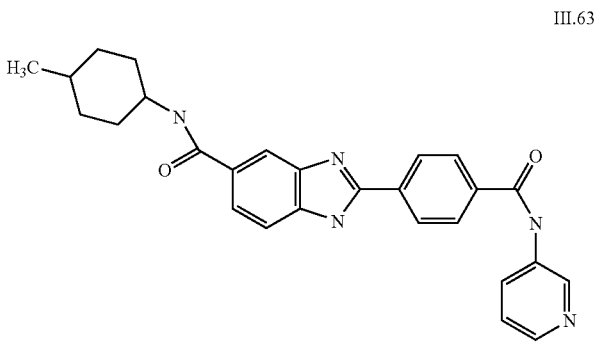
III.64
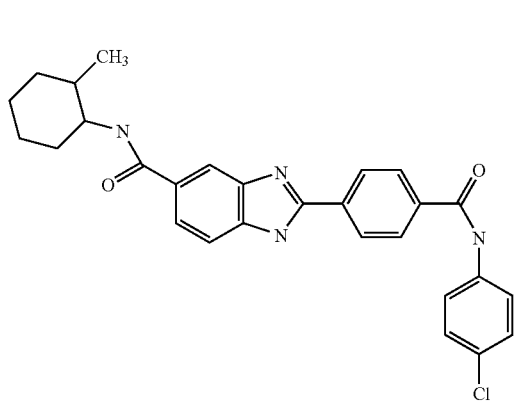
III.65
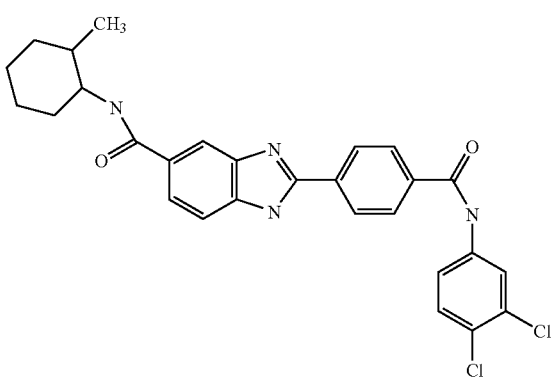
III.66
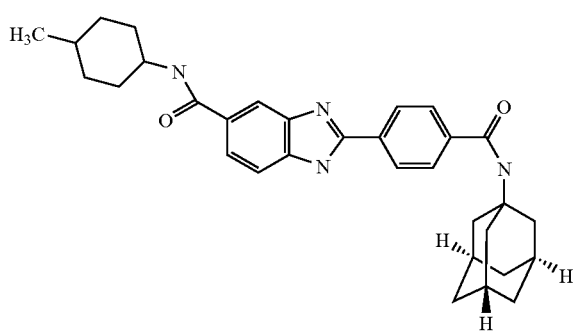
III.67
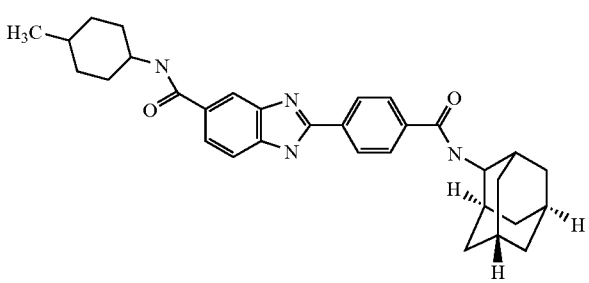

-continued
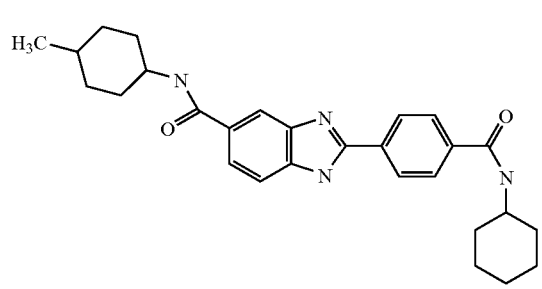
III.68
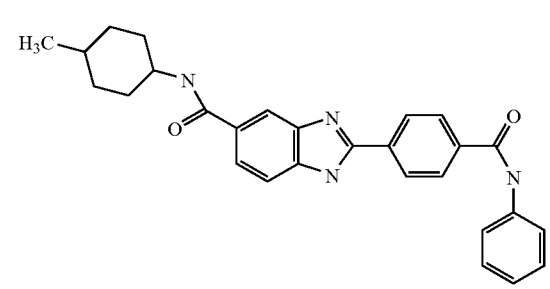
III.69
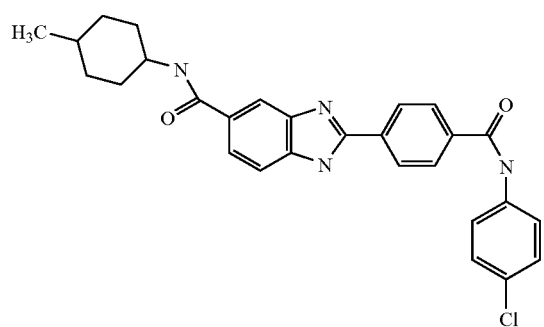
III.70
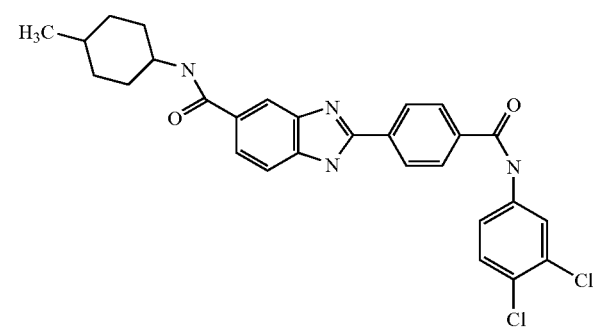
III.71
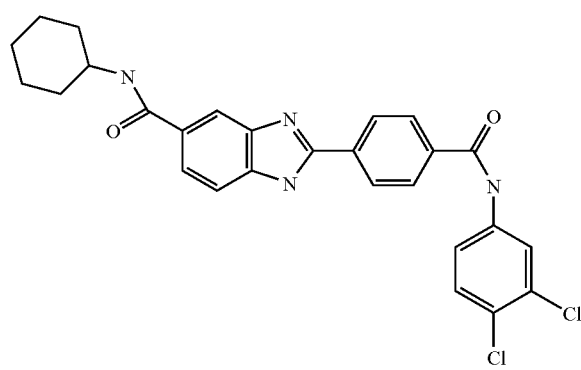
III.72
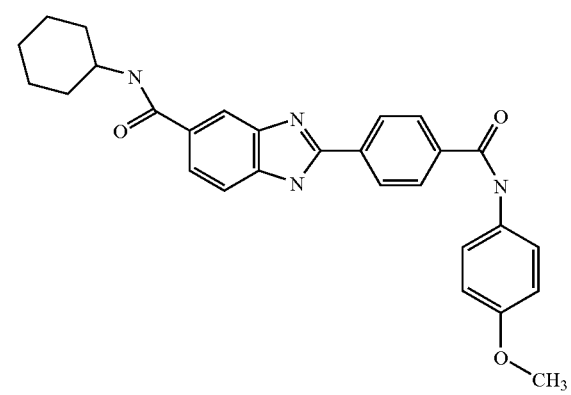
III.73
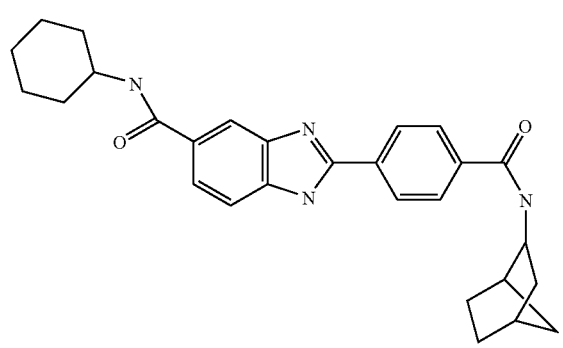
III.74
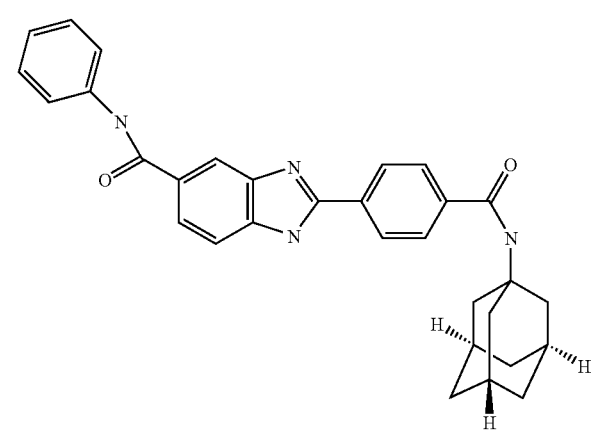
III.75

-continued
III.76
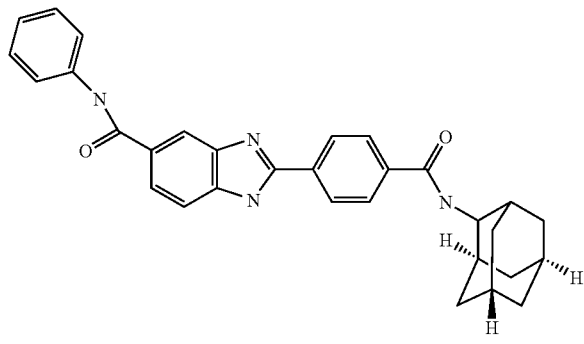
III.77
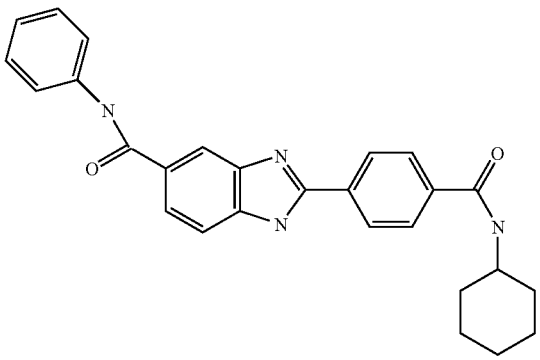
III.78
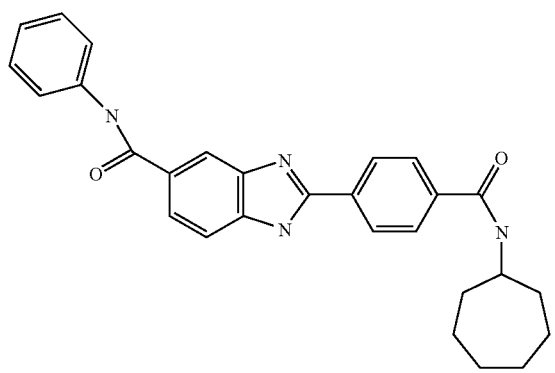
III.79
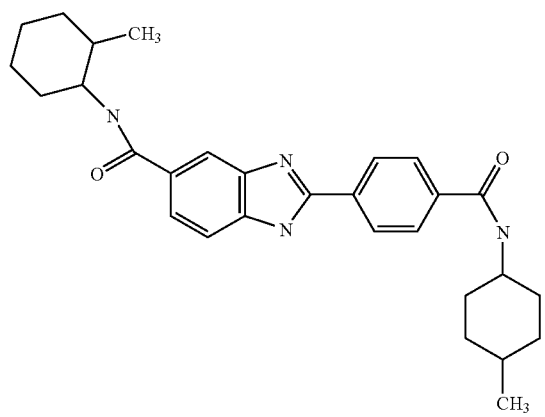
III.80
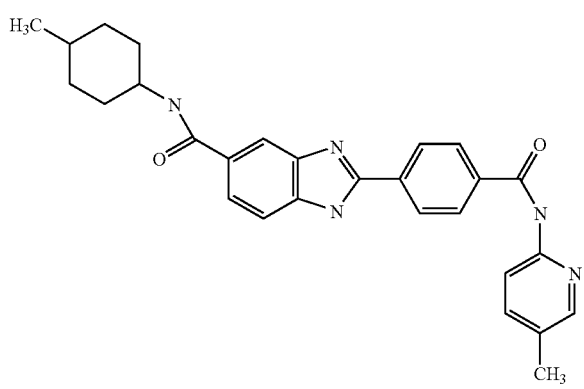
III.81
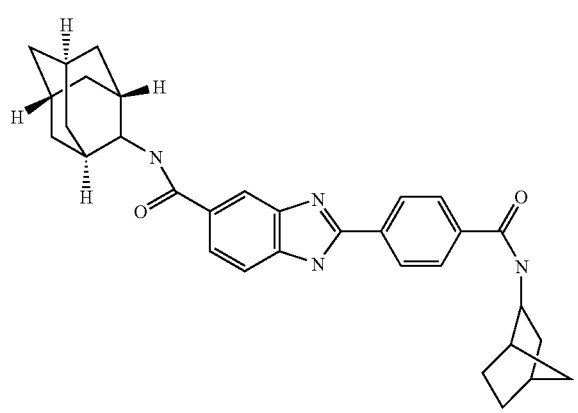

-continued
III.82
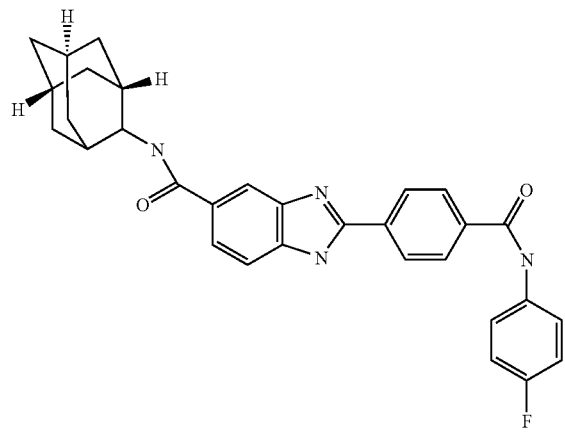
III.83
III.84
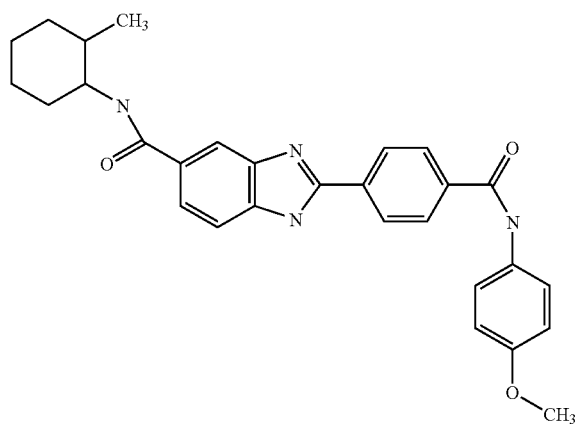
III.85
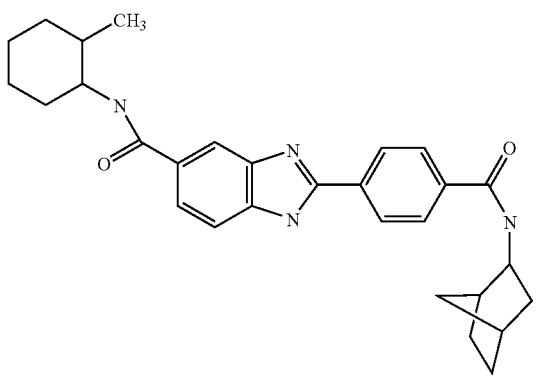
III.86
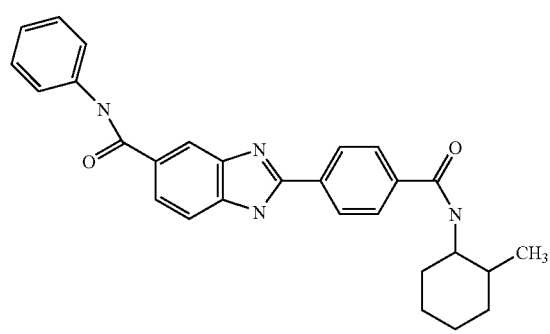
III.87
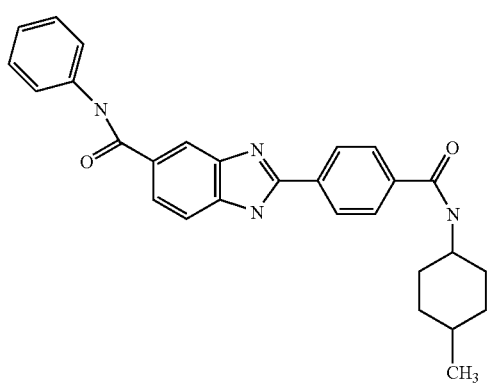

-continued
III.88
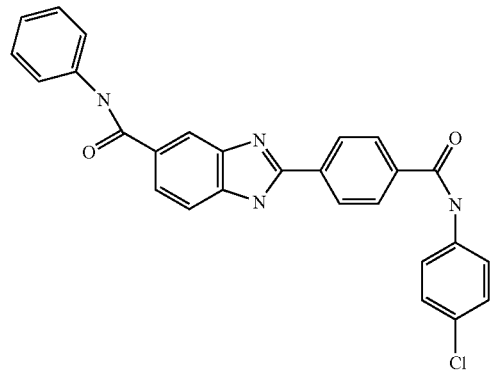
III.89
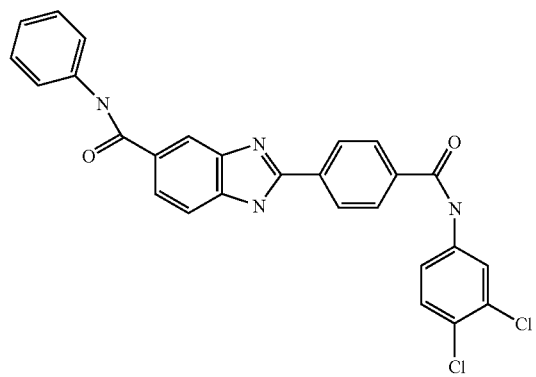
III.90
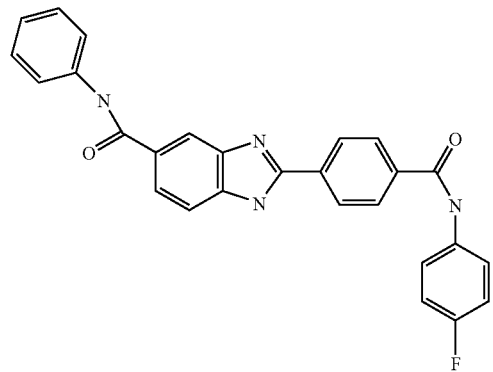
III.91
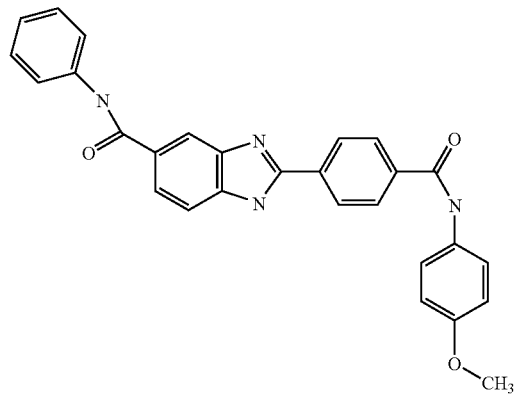
III.92
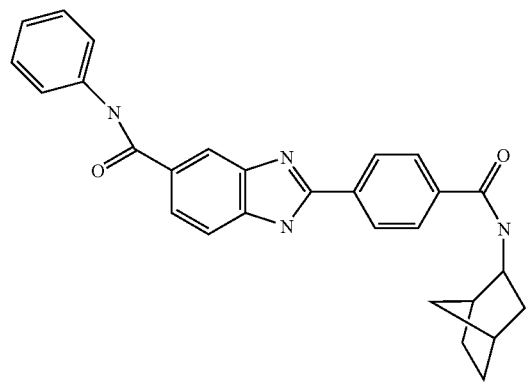
III.93
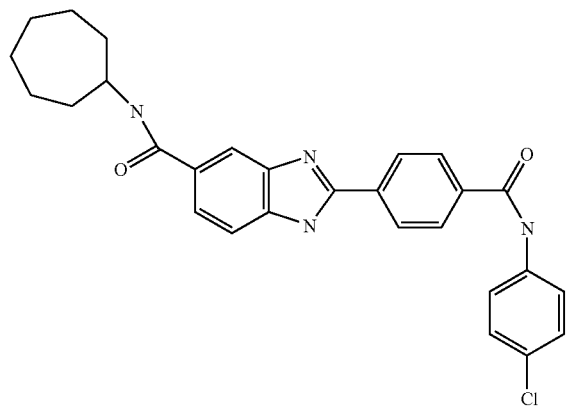
III.94
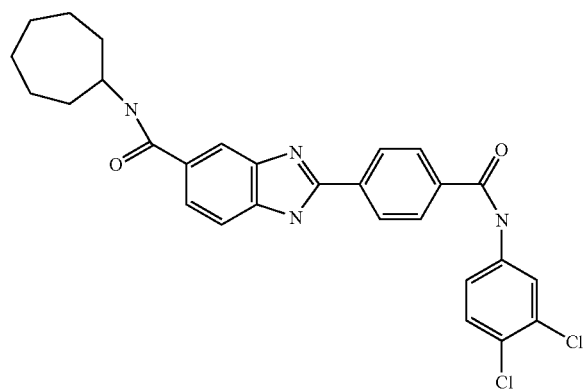
III.95
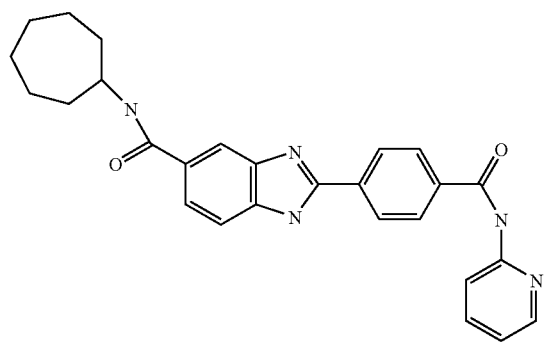

-continued
III.96
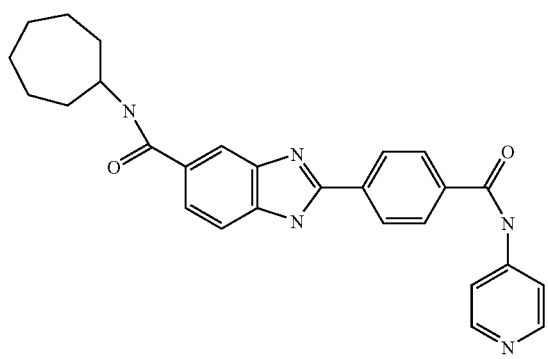
III.97
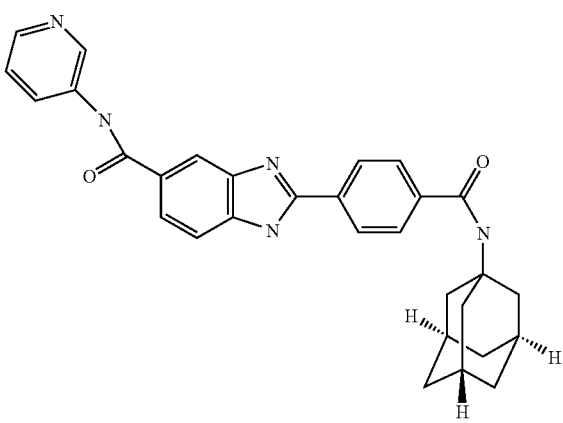
III.98
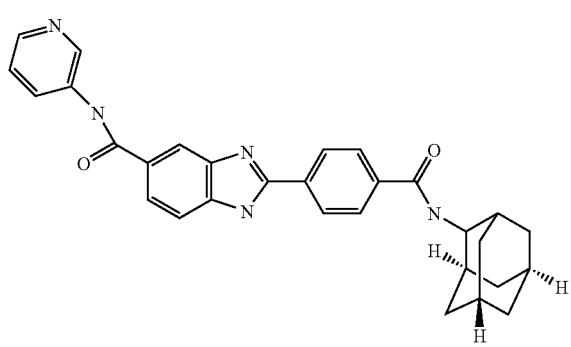
III.99
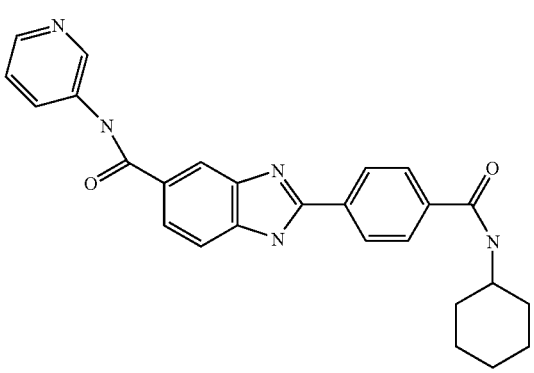
III.100
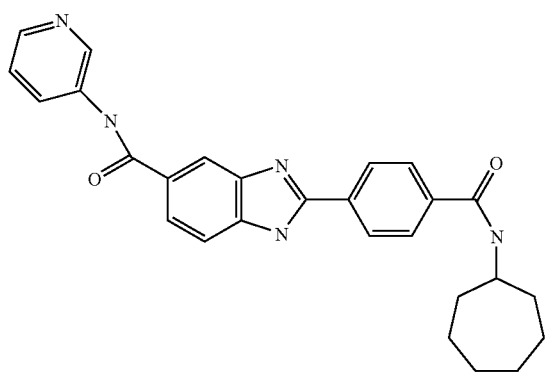
III.101
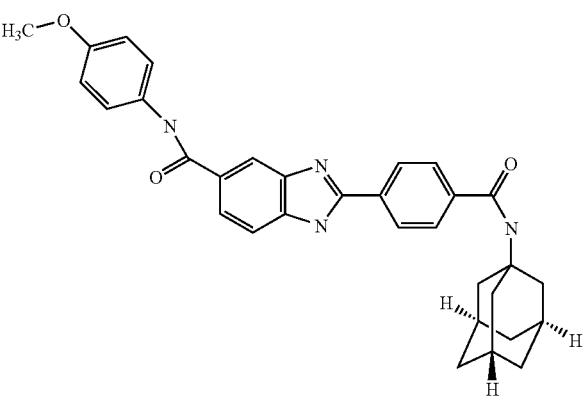
III.102
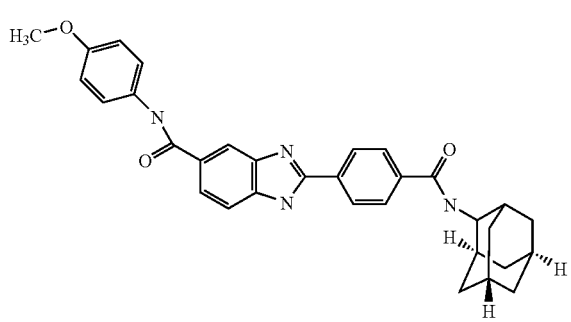
III.103
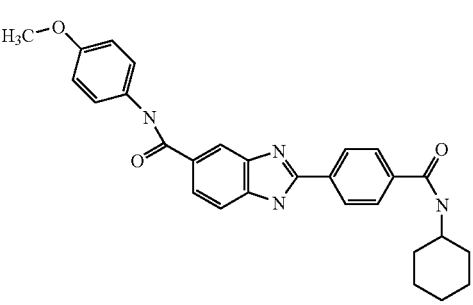

III.104
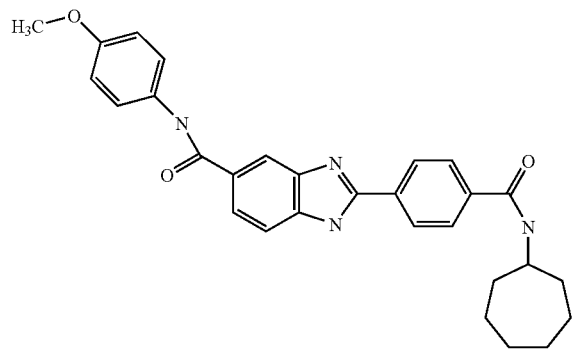
III.105
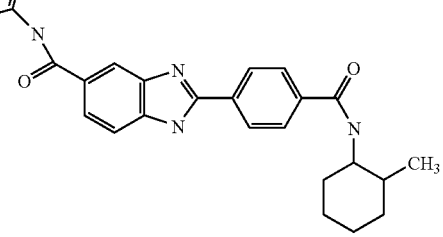
III.106
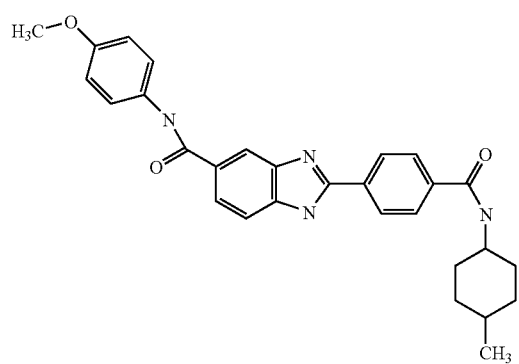
III.107
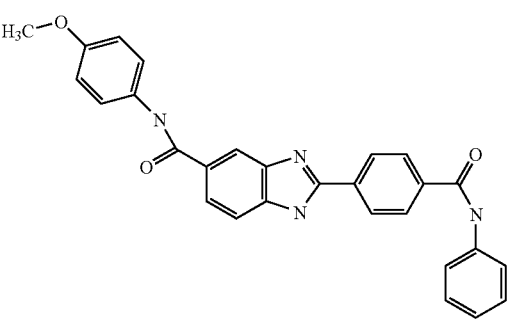
III.108
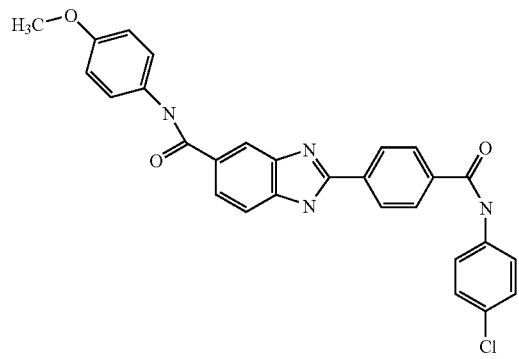
III.109
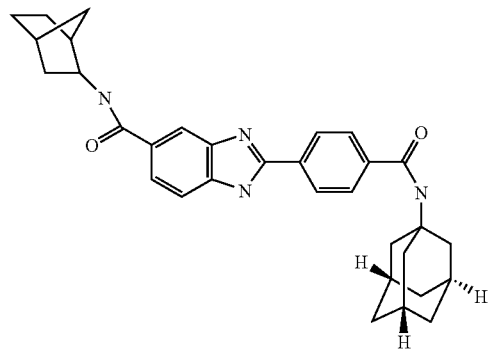
III.110
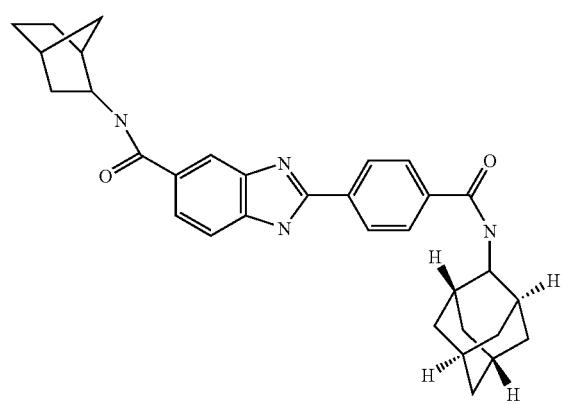
III.111
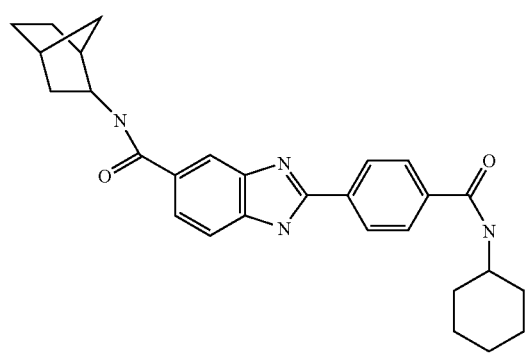

-continued
III.112
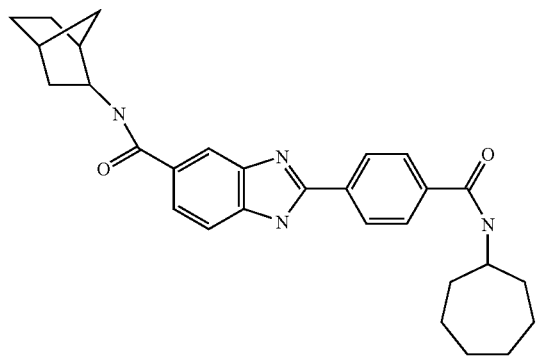
III.113
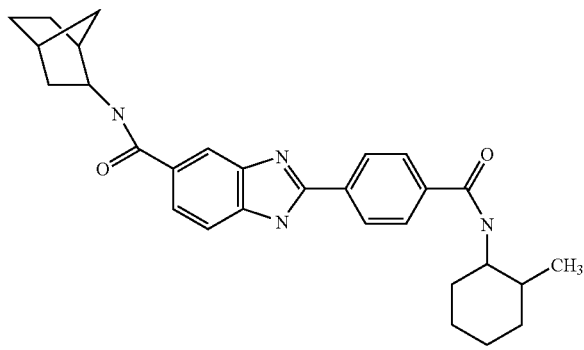
III.114
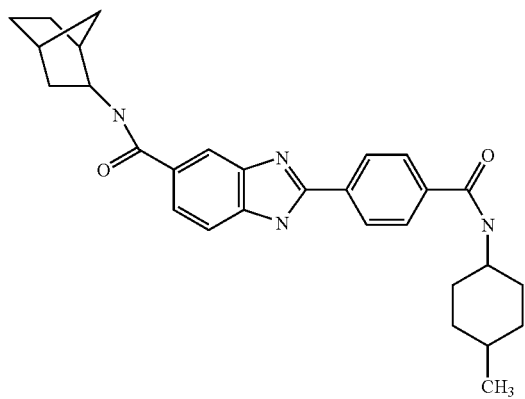
III.115
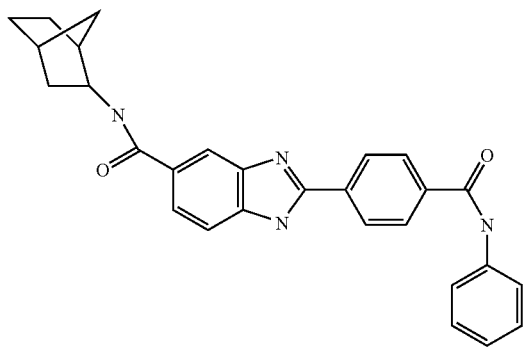
III.116
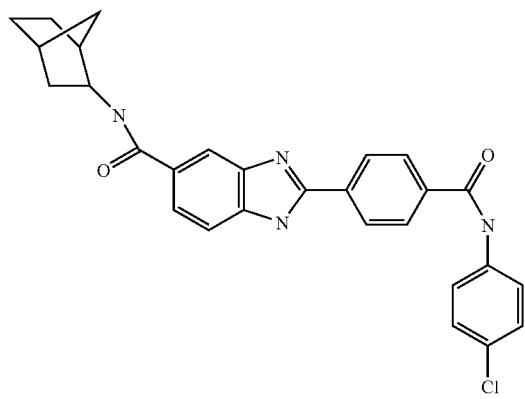
III.117
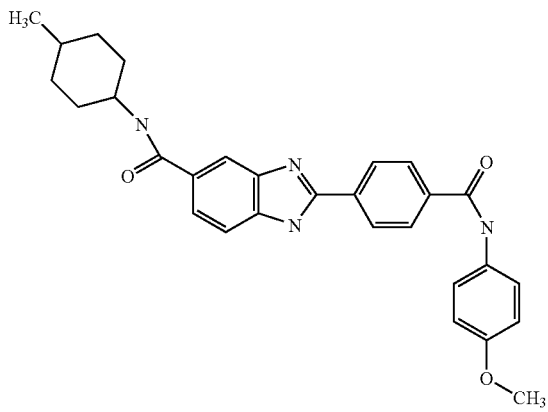
III.118
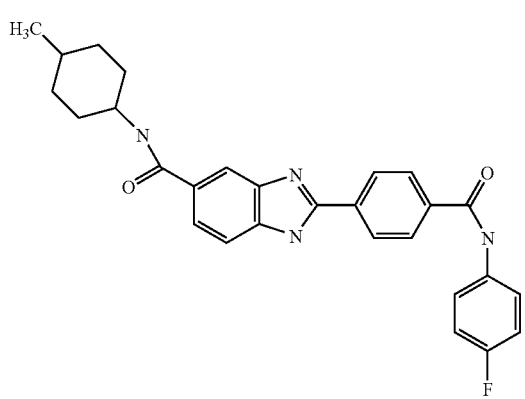
III.119
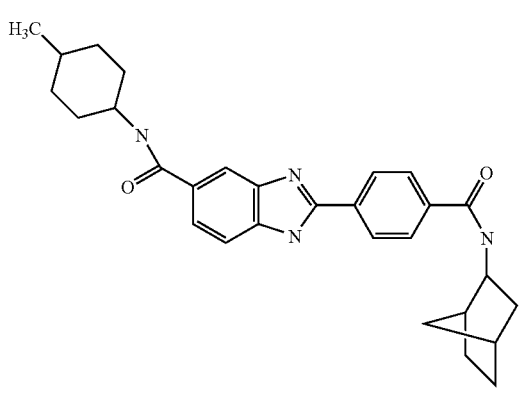

-continued
III.120
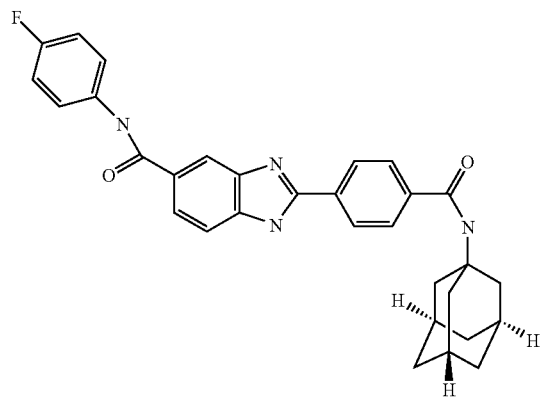
III.121
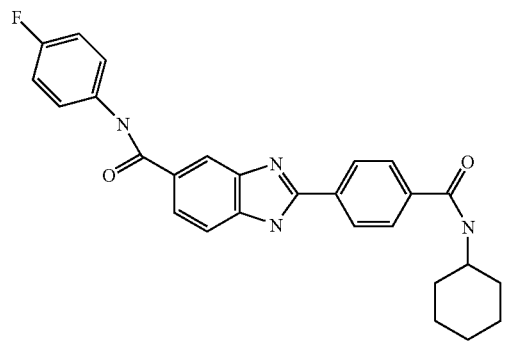
III.122
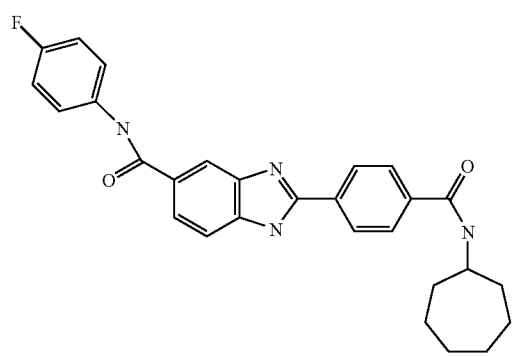
III.123
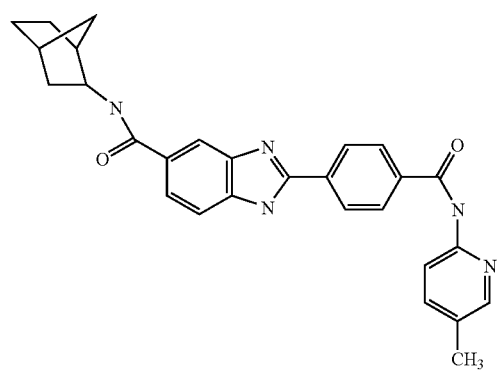
III.124
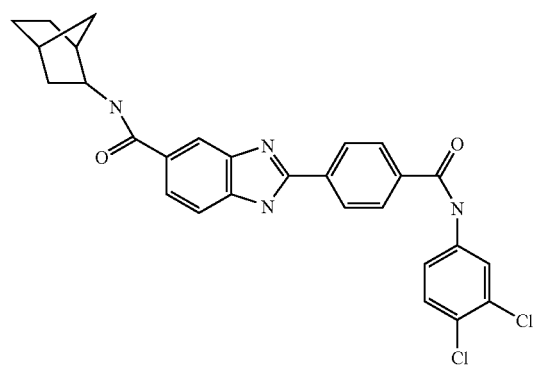
III.125
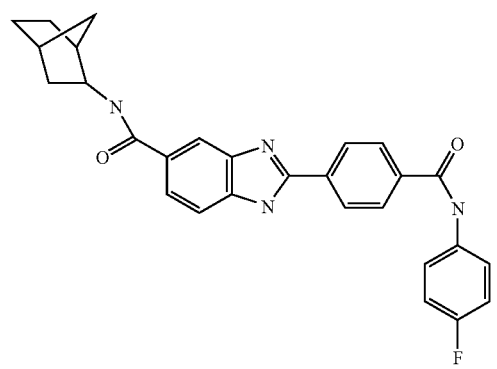
III.126
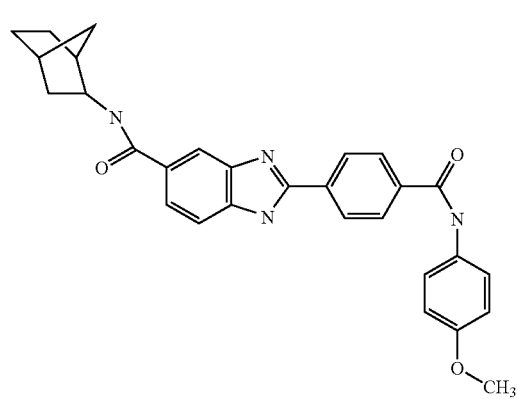
III.127
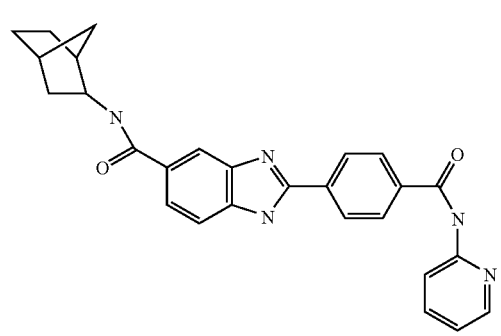

-continued
III.128
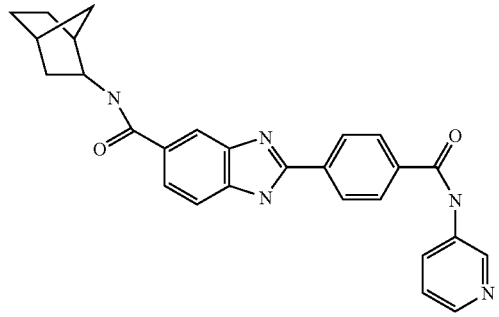
III.129
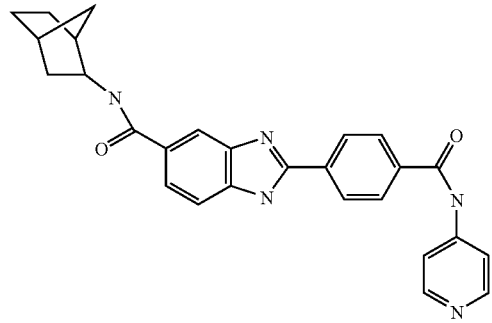
III.130
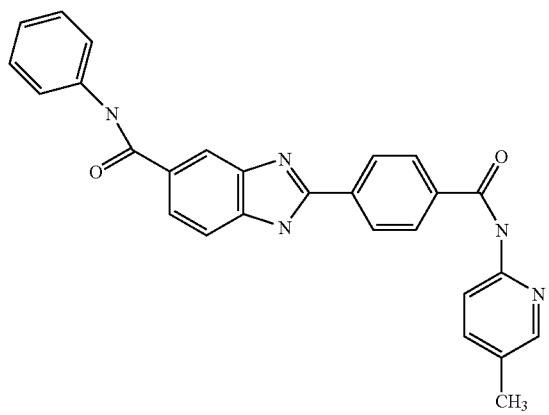
III.131
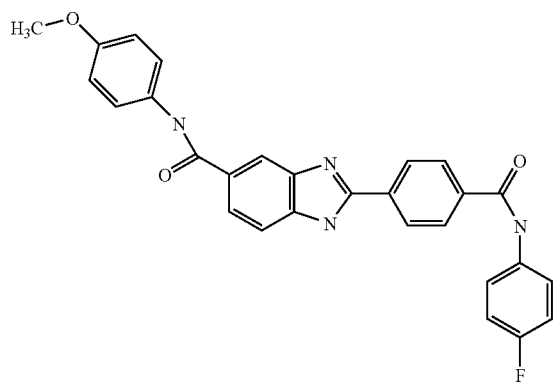
III.132
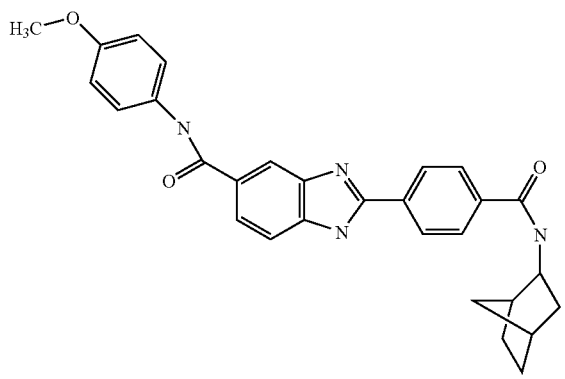
III.133
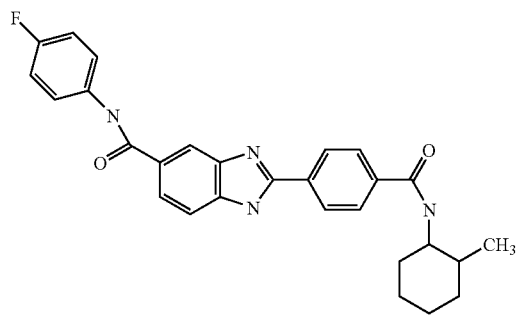
III.134
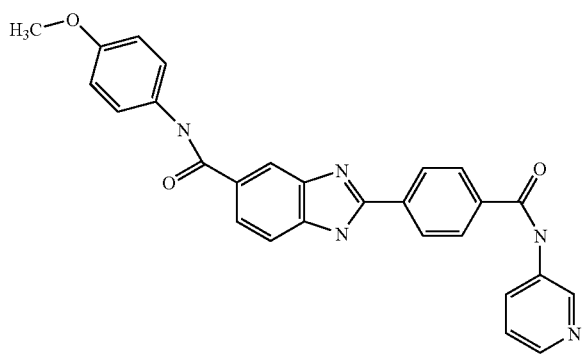
III.135
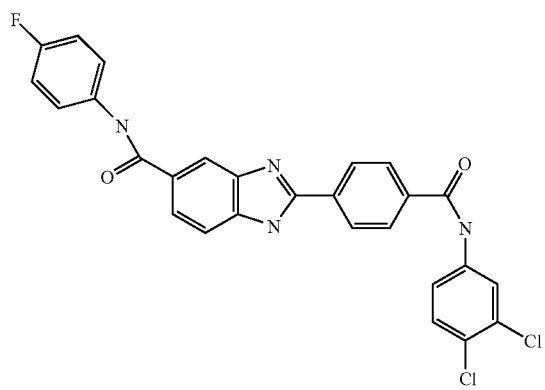

-continued
III.136
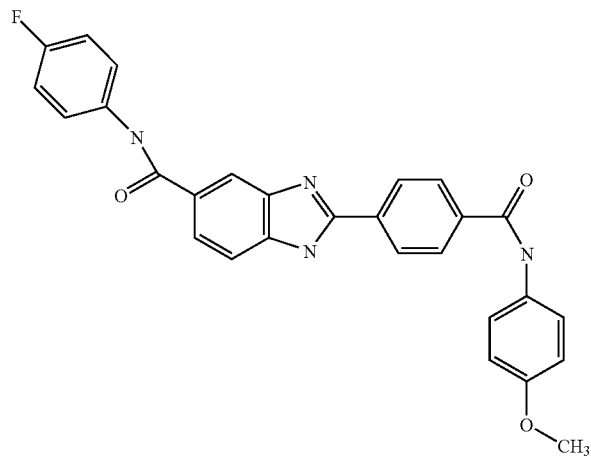
III.137
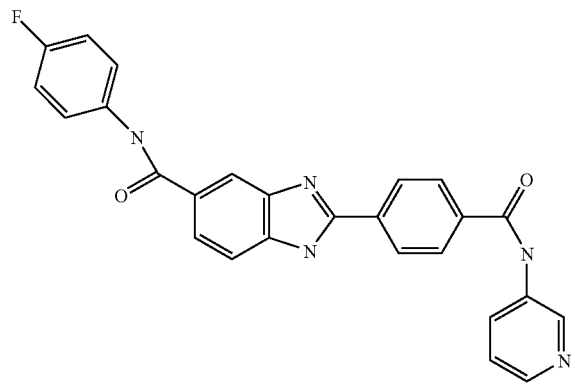
III.138
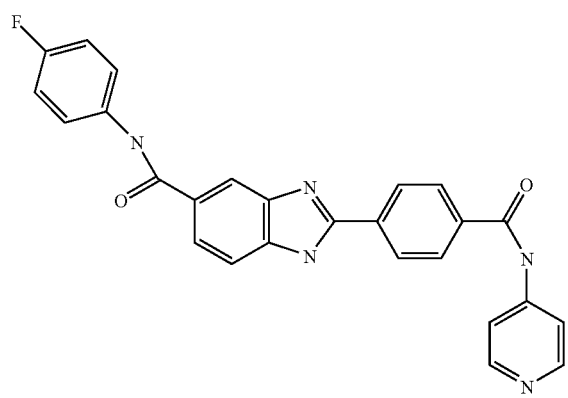
III.139
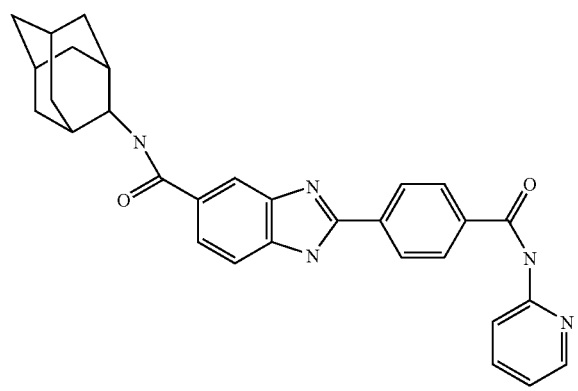
III.140
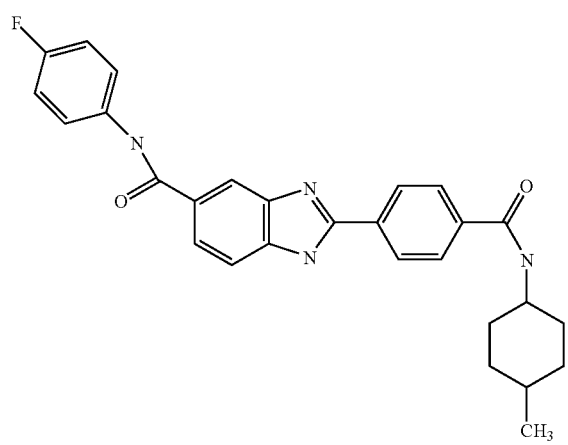
III.141
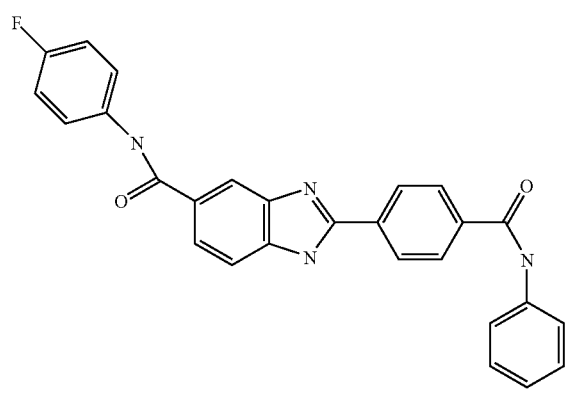

-continued
III.142
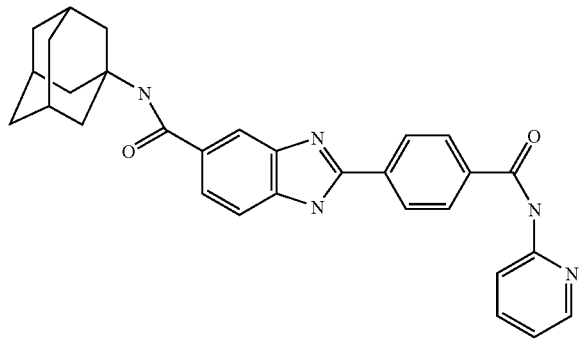
III.143
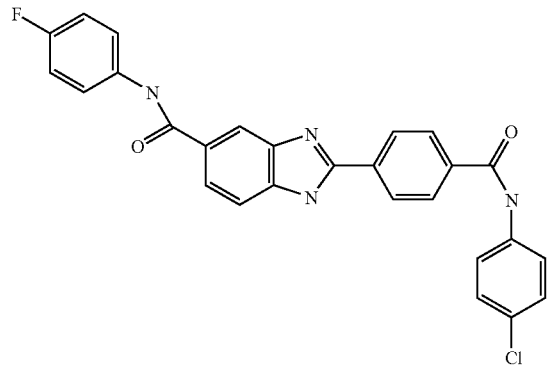
III.144
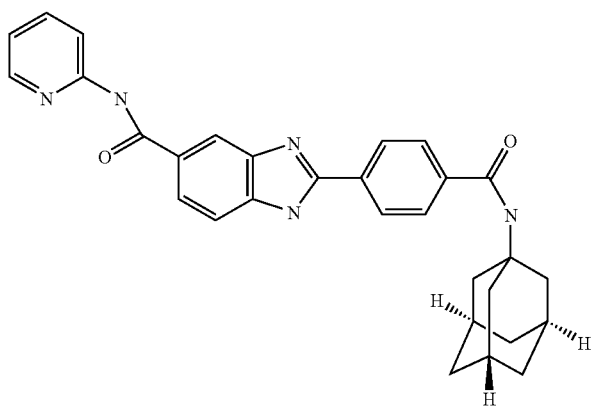
III.145
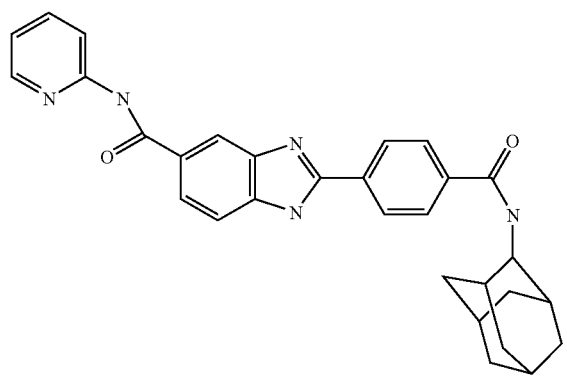
III.146
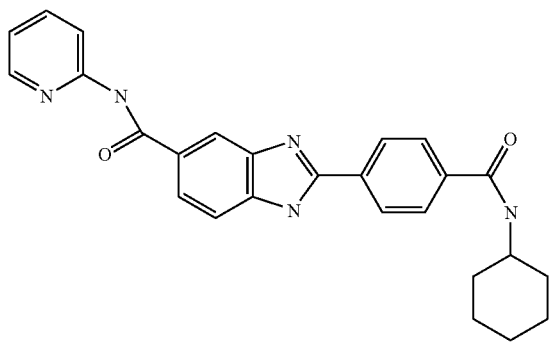
III.147
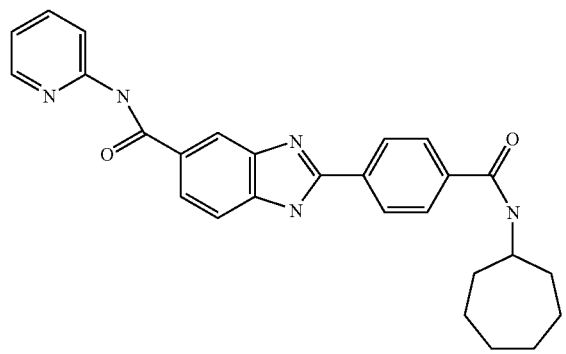

-continued
III.148
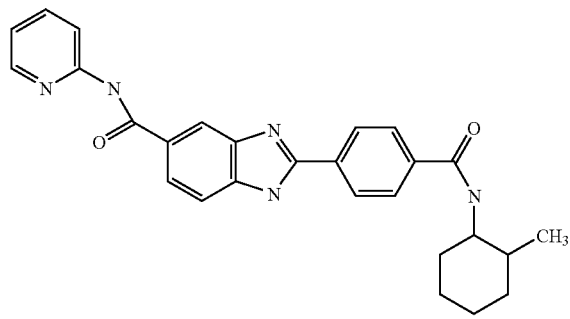
III.149
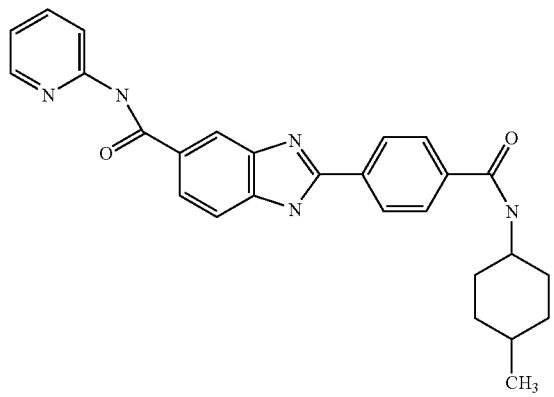
III.150
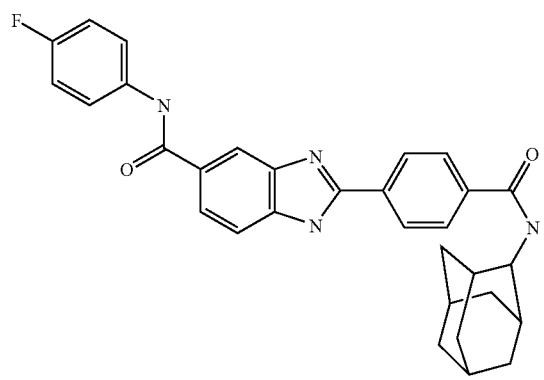
III.151
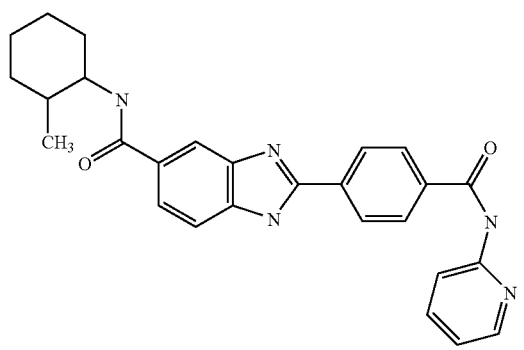
III.152
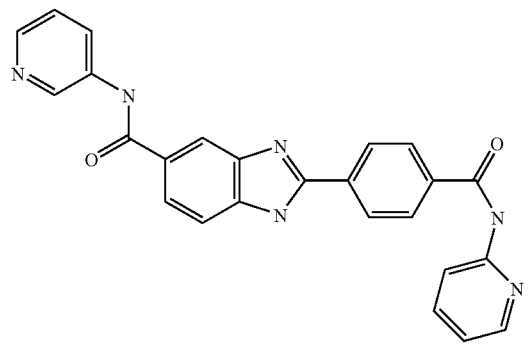
III.153
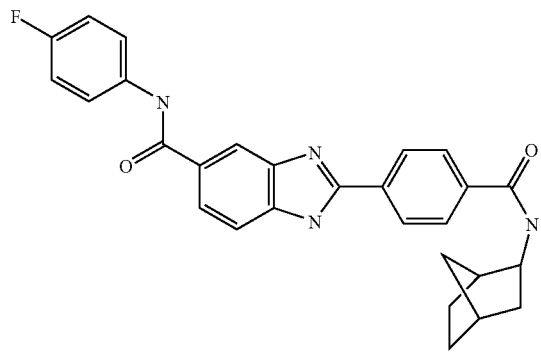
III.154
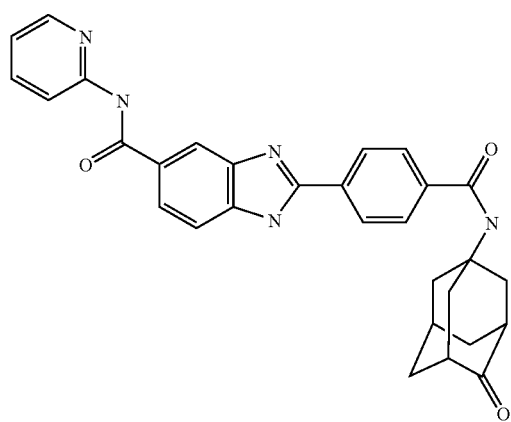

Compounds of Genus III may be synthesized by any conventional reactions known in the art. Examples of syntheses include the following reactions, designated Synthetic Scheme III:

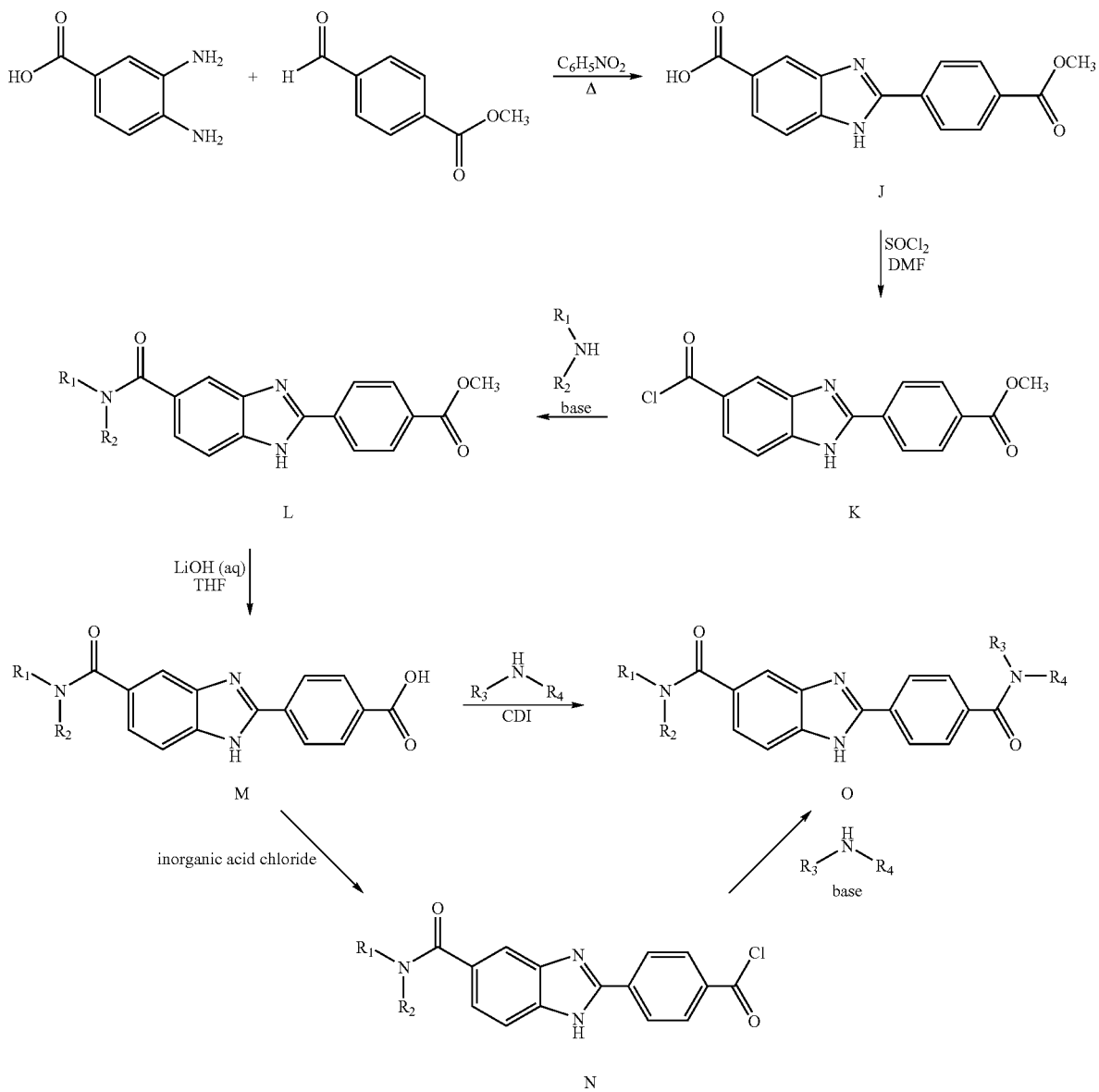

Synthesis of the Compounds of Genus III

Synthetic Scheme 3 shows one method that can be used to prepare the compounds of Genus III. One skilled in the art will appreciate that a number of different syntheses reactions may be used to synthesize the compounds of Genus III. Further, one skilled in the art will understand that a number of different solvents, coupling agents and reaction conditions can be used in the syntheses reactions to yield comparable results.

In step 1, compound J is prepared from a cyclocondensation reaction of 3,4-diaminobenzoic acid or salt thereof and 4-alkoxycarbonyl benzaldehyde. The cyclocondensation reaction may be carried out in a solvent with heat. Examples of solvents are nitrobenzene and other solvents with an oxidizing agent to convert imidazolines to imidazoles. The same compound can be prepared by two-step process, as follows: reacting the diamine with p-carboalkoxy benzoyl chloride in the presence of a base such as triethylamine, DIEP, DMAP or pyridine or other such base; and, cyclizing the resulting amide (by elimination of a mole of water) with PPA, $H_2SO_4$ or other dehydrating agents at an ambient temperature to generate the benzimidazole ring.

In step 2, compound J or salt thereof is treated with an inorganic acid halide such as thionyl chloride, $POCl_3$, $PCl_5$, and the like, or an organic acid chloride such as oxalyl chloride, and the like, or a mixed anhydride, such as t-butyl chloroformate, and the like, to obtain compound K, or similar reactive intermediates, and salt thereof. The reaction may occur in the presence of an inorganic acid halide agent or organic acid chlorides or mixed anhydrides, and the like in a solvent. One specific example of the inorganic acid halide agent is thionyl chloride. One example of the solvent is DMF.

In step 3, compound K or salt thereof is treated with ammonia or an amine to obtain compound L or salt thereof. The amide formation reaction may occur in the presence of a coupling agent, or by converting it to an acid chloride or mixed anhydride and then reacting it with an amine, such as aromatic amines, aliphatic amines, heterocyclic amines, and the like, in a solvent in the presence of another base to absorb the acid produced. This can be carried out with or without heating. Examples of the coupling agents are 1,1'-carbonyldiimidazole (CDI), EDC, and other similar coupling agents. The amide formation reaction may occur in the presence of a base in a solvent. Examples of the solvent include N, N-dimethylformamide (DMF), THF, pyridine, triethylamine or mixed solvent system such as DMF and THF, and the like.

In step 4, compound L or salt thereof is treated with a base to hydrolyze the ester to the acid, with a base such as a lithium hydroxide solution or an aqueous sodium hydroxide, and the like, thereby obtaining compound M or salt thereof. The deprotection reaction may occur in the presence of solvents such as water or alcohol, and the like, including methanol, ethanol, THF, and the like.

In step 5, compound M or salt thereof is treated with ammonia or an amine to obtain compound O or salt thereof. The amide formation reaction may occur in the presence of a coupling agent or by converting it to an acid chloride or mixed anhydride and then reacting with an amine, including aromatic amines, aliphatic amines, heterocyclic amines, and the like, in a solvent in the presence of another base to absorb the acid produced. This can be carried out with or without heating. An example of the coupling agent is 1,1'-carbonyldiimidazole (CDI), EDC and other similar coupling agents. The amide formation reaction may occur in the presence of a base in a solvent. An example of the solvent is N,N-dimethylformamide (DMF), THF, pyridine, triethylamine, and the like, or a mixed solvent system such as DMF and THF, and the like.

Alternatively, compound M or salt thereof is treated with an inorganic acid halide to obtain compound N or salt thereof. The reaction may occur in the presence of an inorganic acid halide agent in a solvent. An example of the inorganic acid halide agent is thionyl chloride. An example of the solvent is DMF.

Then, compound N or salt thereof is treated with ammonia or an amine to obtain compound O or salt thereof. The amide formation reaction may occur in the presence of a base in a solvent.

Compound O is representative of the compounds in Genus III.

One skilled in the art will appreciate variations in the sequence and further, will recognize variations in the appropriate reaction conditions from the analogous reactions shown or otherwise known which may be appropriately used in the processes above to make compounds of compounds J–O.

In the processes described herein for the preparation of compounds J–O of this invention, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of compounds J–O described above are prepared by reacting the appropriate base or acid with a stoichiometric equivalent of the compounds of compounds J–O.

EXAMPLE 1

Preparation of Compounds of Genus I

A. Preparation of Benzimidazole Carboxamides

Preparation of 2-[4-Nitrophenyl]benzimidazole-5-carboxylic acid:

A mixture of 3,4-diamino benzoic acid (300 g; 1.97 mol) and p-nitro benzaldehyde (298 g; 1.97 mol) in nitrobenzene (15 L) were heated around 155° C.–160° C. overnight. The reaction mixture was cooled to room temperature and the precipitated solid was filtered, washed with ether several time to remove all nitrobenzene. The product was treated with charcoal in hot DMF (2 L), filtered and then stirred at RT and diluted with ether (6 L) to give 393 g of solid. The crude solid was again treated with charcoal in hot DMF (1 L), filtered and then diluted with methanol (5 L) and cooled around 0° C. The product was then crystallized again from DMF and ether to give 225 g of the pure product. This was used in the next step.

Preparation of 2-[4-Nitrophenyl]benzimidazole-5-(N-cyclohexyl)carboxylamide:

The carboxylic acid was then converted to the cyclohexyl amide as follows. A mixture of the acid (1.0 g; 3.53 mmol) and CDI (0.6 g, 4.24 mmol) in DMF (20 mL) was stirred at RT for 3 h and then cooled to 0° C. and treated with cyclohexyl amine (0.36 g, 0.42 mL; 3.65 mmol) and stirred for 1 h and then filtered. The crude product was recrystallized from DMF and ether to yield 0.68 g of the desired product. This was used in the next step without any further purification. The product showed a single spot on TLC and different from the starting material.

Preparation of 2-[4-Amino-phenyl]benzimidazole-5-(N-cyclohexyl)carboxylamide:

A mixture of the above carboxylamide (0.5 g; 1.37 mmol), 5% Pd—C (0.35 g) and methanol was stirred in an atmosphere of hydrogen gas until the required amount of hydrogen was taken up. The catalyst was filtered off and the filtrate was concentrated to give a solid (430 g). The product showed a TLC single spot, different from the starting material.

Preparation of 2-[4-((5-methyl isoxazolyl)-3-carbamido) phenyl]benzimidazole-5-(N-cyclohexyl)carboxylamide:

A mixture of 5-methyl isoxazole-3-carboxylic acid (0.23 g; 1.80 mmol), oxalyl chloride (0.46 g; 3.58 mmol) and a drop of DMF in $CH_2Cl_2$ (10 mL) was heated to reflux for an hour. The reaction mixture was concentrated to dryness and the crude acid chloride was used as is in the next reaction. A mixture of the amine above (0.5 g; 1.50 mmol), the crude acid chloride, THF (50 mL) and pyridine (0.54 g) was refluxed overnight. The reaction mixture was poured into water (600 mL). The crude product was filtered, washed with water and hexane and dried. The yield was 380 mg, with a melting point >310° C. The product showed a single spot on TLC.

B. Preparation of 2-[4-(N-(1-adamantyl-carboxamido)phenyl]benzimidazole-5-(N-2-pyridyl)carboxylamide Preparation of 2-[4-Nitrophenyl]benzimidazole-5-(N-2-pyridyl)carboxylamide:

A mixture of 2-[4-Nitrophenyl]benzimidazole-5-carboxylic acid (20.0 g; 0.071 mol) and CDI (17.2 g; 0.11 mol) in DMF was stirred at RT for three hours and then cooled to 0° C. and then added 2-amino pyridine (7.3 g; 0.078 mol) and continued to stir at RT overnight. HPLC showed incomplete reaction. Additional CDI (17.2 g) and 2-aminopyridine (7.3 g) were added and then heated to make a clear solution and stirred an additional 24 hours. TLC analysis showed the reaction to be incomplete, so additional amount of 2-aminopyridine (7.3 g) was added along with DMAP (13.4 g; 0.11 mol) and stirred overnight. TLC showed the reaction was complete, the reaction mixture was poured on into water (3.0 L), stirred for an hour, filtered, washed with water and ether (3×100 mL) and dried. The yield was 17 g (67%). This was used in the next step without any other purification. TLC showed one spot (CH2Cl2-CH3OH: 9:1).

Preparation of 2-[4-Amino-phenyl]benzimidazole-5-(N-2-pyridyl)carboxylamide:

A mixture of 2-[4-Nitrophenyl]benzimidazole-5-(N-2-pyridyl)carboxyl amide (17 g; 0.47 mol) and 5% Pd—C 93.0 g) in methanol; (1.0 L) and DMF (200 mL) was stirred under hydrogen until the reaction is complete. The catalyst was filtered off and concentrated and then poured into water (5.0 L), filtered, washed with water and ether (3×100 mL) and oven dried under vacuum at 80° C. The yield was 10 g, with a melting point of 260° C.–265° C. TLC showed a single spot with $CH_2Cl_2$—$CH_3OH$ (9:1) as eluents. 2-[4-(N-(1-adamantyl-carboxamido)phenyl]benzimidazole-5-(N-2-pyridyl)carboxylamide:

A mixture of 2-[4-Amino-phenyl]benzimidazole-5-(N-2-pyridyl)carboxyl amide (2.6 g; 0.7.89 mmol) and pyridine (2.9 mL) in THF (250 mL) was heated to make a clear solution. The reaction mixture was then treated with 1-adamantylcarbonyl chloride (1.88 g; 9.47 mmol) in THF (10 mL) and the mixture was heated to reflux for 24 hours. The mixture was poured into water (1.5 L) and stirred for one hour, filtered, washed with water (3×50 mL) and ether (3×50 mL) and dried. It was treated with charcoal and re-crystallized from THF and methanol. The filtrate was diluted with ether (150 mL) and cooled to −70° C. for 4 hours when the product crystallized out. It was filtered, washed with ether and dried. The yield was 2.9 g, with a melting point of 333° C.–336° C. TLC showed one spot with $CH_2Cl_2$—$CH_3OH$ (9:1) as eluent.

EXAMPLE 2

Preparation of Compounds of Genus II

A. Preparation of 2-(4-N-(2-methyl-cyclohexyl)benzamido)-5-(benzamido) benzimidazole:

Preparation of 2-(4-carbomethoxy-phenyl)-5-nitro-benzimidazole:

A mixture of 4-nitrophenylene-1,2-diamine (634 g) and methyl-4-formyl benzoate (680 g) was heated in nitrobenzene (17 L) at 150–155° C. for 24 hours, cooled to RT and the product filtered, washed with ether (3×1.0 L) and dried to give the desired product. Yield 800 g. TLC one spot: (9:1)—$CH_2Cl_2$—$CH_3OH$.

Preparation of 2-(4-carboxy-phenyl)-5-nitro-benzimidazole:

A mixture of the above ester (800 g), THF (2.7 L) and water (2.6 L) was treated with LiOH (339 g) and stirred at RT. The progress of the reaction was followed by TLC until the hydrolysis was complete. The reaction mixture was diluted with hot water (2.0 L), charcoal and then filtered. The filtrate was diluted with 2.0 kg of ice and water (1.0 L) and acidified with conc. HCl. The product was filtered, washed with water and then recrystallized from hot DMF (7.0 L) (with charcoal treatment) and filtered. The filtrate was diluted with ether (7.0 L) and chilled to 4.0° C. The product was filtered, washed with ether and dried. Yield 537 g; m.p. >355° C. TLC one spot: (9:1)-$CH_2Cl_2$—$CH_3OH$.

Preparation of 2-(4-N-(2-methyl-cyclohexyl)benzamido)-5-nitro-benzimidazole:

A mixture of the above acid (20.0 g) in DMF (400 mL) was treated with CDI (13.7 g) and the mixture was stirred at RT for 2.0 hours and then treated with 2-methyl-cyclohexyl amine (11.2 g). The reaction mixture was heated to reflux for 16 hours. It was poured into ice-water (3.0 L) and stirred at RT for 16 hours. The crude product was filtered, washed with water (3×100 mL) and ether and dried. Yield 19 g; TLC one spot: (9:1)-$CH_2Cl_2$—$CH_3OH$.

Preparation of 2-(4-N-(2-methyl-cyclohexyl)benzamido)-5-amino-benzimidazole:

The above nitro amide (19.0 g) was hydrogenated in presence of 5% Pd—C (4.0 g) in MeOH (600 mL). The catalyst was filtered off and the filtrate was concentrated under vacuum and the residue was treated with ether (200 mL) and filtered. The residue was then recrystallized from THF, MeOH and hexane. The product was filtered, washed with hexane and oven dried. Yield 10.5 g; TLC one spot: (9:1)-$CH_2Cl_2$—$CH_3OH$.

Preparation of 2-(4-N-(2-methyl-cyclohexyl)benzamido)-5-(benzamido)-benzimidazole:

A mixture of the above amine (0.5 g) in THF (50 mL) and pyridine (0.53 mL) was heated to a clear solution and the solution was treated drop wise with benzoyl chloride (0.24 g) in 10 mL THF. The reaction mixture was heated to reflux for 24 hours, cooled and then poured into water (600 mL). The product was filtered, washed with water, ether and dried. The crude product was treated with charcoal in hot THF-methanol and filtered. The filtrate was diluted with ether and chilled. The product was filtered, washed with ether and dried. Yield 338 mg; m.p. 285–289° C.; TLC one spot: (9:1)-$CH_2Cl_2$—$CH_3OH$.

EXAMPLE 3

Preparation of Compounds of Genus III

A. Preparation of 2-(4-Cyclohexylcarbamoyl-phenyl)-3H-benzoimidazole-5-carboxylic acid cyclohexyamide:

Preparation of 2-(4-methoxycarbonyl-phenyl)-3H-benzoimidazole-5-carboxylic acid:

A mixture of 3,4-diaminobenzoic acid (300 g) and methyl-4-formyl benzoate (324 g) in nitrobenzene (8.0 L) was heated at 150–155° C. for 24 hours and then cooled to <10° C. when the product crystallized out. It was filtered and then washed with ether (3×200 mL) and vacuum dried. Yield 320 g, m.p. 308–309° C. This was used in the next step without any additional purification.

Preparation of 2-(4-carboxy-phenyl)-3H-benzoimidazole-5-carboxylic acid:

A mixture of 2-(4-methoxycarbonyl-phenyl)-3H-benzoimidazole-5-carboxylic acid (4.1 g) in THF (15 mL) and water (18 mL) and LiOH (1.74 g) was stirred for 16 hours at room temperature and then mixed with hot water (100 mL) and charcoal. The mixture was filtered and the filtrate was diluted with ice and water (100 mL) and acidified with conc. HCl. The crude diacid was filtered, washed with water and ether and then recrystallized from THF and MeOH. Yield 3.3 g; TLC single spot [$CH_2Cl_2$—$CH_3OH$ (9:1)].

Preparation of 2-(4-Cyclohexylcarbamoyl-phenyl)-3H-benzoimidazole-5-carboxylic acid cyclohexyamide:

A mixture of 2-(4-carboxy-phenyl)-3H-benzoimidazole-5-carboxylic acid (0.50 g) in DMF (50 mL) and N-methylmorpholine (0.72 g) was chilled to −10°–20° C. and then added isobutyl chloroformate (0.60 g) dropwise maintaining the temperature. After 10 min, cyclohexylamine (0.53 g) in DMF (10 mL) was added dropwise. The mixture was then slowly allowed to come to room temperature and stirred for 48 hours. The reaction was followed by TLC for completion. The mixture was then poured in water (600 mL), filtered, washed with water and ether and recrystallized from THF and MeOH. A second recrystallization was done using charcoal to give pure product. Yield 270 mg, m.p. 334–337° C.

B. Preparation of 2-(4-Carbomethoxy-phenyl)-5-(N-cyclohexyl-carboxamido) benzimidazole:

A mixture of 2-(4-methoxycarbonyl-phenyl)-3H-benzoimidazole-5-carboxylic acid (5.0 g) in DMF (250 mL) and CDI (7.1 g) was stirred at RT for 3.0 hours and then treated with cyclohexyl amine (2.0 g) and refluxed for 96 hours. The reaction mixture was cooled and then poured into water (2.0 L) and stirred at RT for 16 hours. The product was filtered, washed with water and ether and then recrystallized from THF, methanol and ether. Yield 0.4 g. TLC one spot (9:1)-$CH_2Cl_2$—$CH_3OH$.

This ester was hydrolyzed to give the acid which was used to couple with various amines to give the unsymmetrical bis amides.

C. Preparation of 2-(4-(N-cyclohexyl)-benzamido)-benzimidazole-5-carboxylic acid and unsymmetrical bis-amides:

A mixture of 3,4-diaminobenzoic acid (1.71 g) and 4-(N-cyclohexyl)-benzamido)-benzaldehyde (2.6 g) in 200 mL nitrobenzene was heated at 150 155° C. for 16 hours. It was cooled, filtered, washed with ether and dried. Yield 1.9 g; TLC one spot (9:1)-$CH_2Cl_2$—$CH_3OH$.

The acid was then coupled with various amines with CDI in DMF and/or THF to give the unsymmetrical bis amides.

D. Preparation of 2-(4-carboxy-phenyl)-5-(N-cyclohexyl-carboxamido)-benzimidazole:

A mixture of 5.2 g of 2-(4-carbomethoxy-phenyl)-5-(N-cyclohexyl-carboxamido)-benzimidazole in THF (50 mL) and water (40 mL) was added LiOH (1.73 g). The mixture was stirred at RT for 2 hours and then mixed with charcoal and stirred with slight heating and then filtered. The filtrate was chilled in ice and then acidified with conc. HCl to pH 1.0. The acid was filtered, washed with water and ether and dried. Yield 4.7 g, HPLC 95%, m.p. 311–314° C. This was coupled with various amines to give unsymmetrical bis amides using CDI or isobutyl chloroformate as coupling agent. One such example is as follows: A mixture of the acid (0.5 g) in THF (50 mL) and N-methyl morpholine (0.64 g) was cooled to −10–20° C. and then drop wise treated with isobutyl chloroformate (0.3 g). The reaction mixture was stirred for 10 min and then 1-adamantane amine was added to the mixture and the reaction mixture was stirred for 15 hours. The reaction mixture was poured into water and ice and then filtered, washed with water, ether and then recrystallized from THF/MeOH to give the desired product. Yield 320 mg, m.p. >355° C.

EXAMPLE 4

Suppression of IgE Response

The inhibitory activity of the small molecules of the present invention were assayed using both the ex vivo and in vivo assays as described above. All of the compounds presented above were active in suppressing the IgE response. In the ex vivo assay, compounds in Genuses I-III produced 50% inhibition at concentrations ranging from 1 pM to 100 µM. In the in vivo assay, the compounds were effective at concentrations ranging from less than about 0.01 mg/kg/day to about 100 mg/kg/day, when administered in divided doses (e.g., two to four times daily) for at least two to seven consecutive days. Thus, the small molecule inhibitors of the present invention are disclosed as being useful in lowering the antigen-induced increase in IgE concentration, and consequently, in the treatment of IgE-dependent processes such as allergies in general and allergic asthma in particular.

EXAMPLE 5

Effects on Cellular Proliferation

A variety of experiments were performed in an effort to determine the effect of the benzimidazole compounds on cellular proliferation. These experiments ultimately measured $^3H$-thymidine incorporation into proliferating cell DNA. The specific procedure varied with the cells and the stimuli. Cells derived from mouse spleen were cultured at 3 million per ml; cell lines were seeded at 0.1 to 1 million per ml. Splenic B cells were isolated by T cell depletion and stimulated with phorbol myristate acetate (PMA) (10 ng/ml) plus ionomycin (100 nM), or IL-4 (10 ng/ml) plus anti-CD40 Ab (100 ng/ml). T cells were depleted prior to culture by incubating spleen cells first with a cocktail of anti-Thy1 ascites (10%), anti-CD4 Ab (0.5 µg/ml) and anti-CD8 Ab (0.5 µg/ml), followed by guinea pig complement (adsorbed). Cell lines were unstimulated or stimulated with Human Epidermal Growth Factor (EGF) (100 ng/ml). All cells were cultured in 96-well plates for 2–3 days and pulsed for 6 to 14 hours with 50 µl of 3H-thymidine (50 µCi/ml).

In spleen cells, Compound I.82 suppressed B cell proliferation responses to PMA/ionomycin and IL-4/anti-CD40 Ab (FIG. 1) with approximately the same potencies as it suppressed in vitro IgE responses to IL-4/anti-CD40 Ab. Similar inhibition potencies were obtained for Compound I.82 in ConA-stimulated T cell proliferation and LPS-stimulated B cell proliferation (preformed by MDS Pharma), suggesting a lack of specificity in the action of these drugs. On the other hand, a battery of immunological tests performed with Compound I.82 demonstrated little other effects other than inhibition of ConA-stimulated cytokine release.

In tumor cells, the results with splenic lymphocytes led to a further analysis of cellular proliferation by measuring the growth of tumor cells in the presence of these drugs. The initial analysis was performed with murine M12.4.1 lymphoma cells, either un-stimulated or stimulated with IL-4/anti-CD40 Ab. Compound I.82 suppressed the proliferation of M12.4.1 cells but with lower potency that observed in stimulated spleen cells. However, the potency of Compound I.82 increased when the cells were cultured with IL-4/anti-CD40 Ab. This stimulation is known to induce the activity of NF-κB in M12.4.1 cells.

A similar approach was used to establish selectivity of the anti-proliferative activity by testing a battery of tumor lines derived from a variety of tissues, mostly human in origin. An attempt was made to generate proliferation data from at least 2 cell lines from each tissue selected. Only a handful of cell lines were inhibited by 100 nM or less of each compound while most the balance of the cells required much higher concentrations. Because of the known character of some of the tested cell lines and previous Western blot results with the compounds, there is evidence to suggest a link between NF-κB inhibition and the action of the drugs. Breast cancer cells offer a good model for testing this phenomenon because they are predominantly of 2 types; estrogen receptor (ER)-positive and ER-negative. The latter cells tend to be less differentiated, have a higher density of EGF receptor expression, and are more resilient to treatment. Proliferation of ER-negative/EGFR-positive cells also tends to be driven by NF-κB and thus a selection of these cells were tested for proliferation responses to drug in vitro. The proliferation of all of the EGF-responsive cell lines was potently inhibited by Compound I.82 in vitro. Conversely, only 2 of the 5 ER-positive cell lines were potently inhibited by drug.

Compound I.82 exert an anti-proliferative activity to T and B lymphocytes exposed to a variety of immunogenic stimuli in vitro. These actions are highly potent and parallel their IgE-suppression activity. Although the mechanism of this action is unresolved, much is known about the mechanism of IL-4/anti-CD40 Ab-induced IgE production. A major factor in this response is the transcription activator, NF-κB. This factor has been implicated in the proliferation of a number of tumor cells and thus these drugs were tested for activity on the proliferation of various tumor cell lines in vitro. Our experiments revealed that a number of tumor cell lines are sensitive to the effects of Compound I.82, and that proliferation of many of the sensitive lines may be driven by NF-κB factors. However, other cell lines known to be driven by factors other than NF-κB (e.g., the ER-positive HCC 1500 and ZR-75-1). Thus, Compound I.82 appears to selectively act on certain tumor cells. Other compounds disclosed in accordance with the present invention are also expected to exhibit similar characteristics, particularly those compounds which are structurally similar to Compound I.82.

Treatment Regimens

The amount of the benzimidazole compounds which may be effective in treating a particular allergy or used as an anti-proliferation agent will depend on the nature of the disorder, and can be determined by standard clinical techniques. The precise dose to be employed in a given situation will also depend on the choice of compound and the seriousness of the condition, and should be decided according to the judgment of the practitioner and each patient's circumstances.

As an anti-allergy therapy, appropriate dosages can be determined and adjusted by the practitioner based on dose response relationships between the patient's IgE levels as well as standard indices of pulmonary and hemodynamic changes. Moreover, those skilled in the art will appreciate that dose ranges can be determined without undue experimentation by following the protocol(s) disclosed herein for ex vivo and in vivo screening (See for example Hasegawa et al., *J. Med. Chem.* 40: 395–407 (1997) and Ohmori et al., *Int. J. Immunopharmacol.* 15:573–579 (1993); employing similar ex vivo and in vivo assays for determining dose-response relationships for IgE suppression by naphthalene derivatives; incorporated herein by reference).

Initially, to exert anti-allergic or anti-asthmatic effects, suitable dosages of the compounds will generally range from about 0.001 mg to about 300 mg per kg body weight per day in divided doses, more preferably, between about 0.01 mg and 100 mg per kg body weight per day in divided doses. The compounds are preferably administered systemically as pharmaceutical formulations appropriate to such routes as oral, aerosol, intravenous, subcutaneously, or by any other route which may be effective in providing systemic dosing of the active compound. The compositions of pharmaceutical formulations are well known in the art. The treatment regimen preferably involves periodic administration. Moreover, long-term therapy may be indicated where allergic reactions appear to be triggered by continuous exposure to the allergen(s). Daily or twice daily administration has been effective in suppressing the IgE response to a single antigen challenge in animals when carried out continuously from a period of two to seven consecutive days. Thus, in a preferred embodiment, the compound is administered for at least two consecutive days at regular periodic intervals. However, the treatment regimen, including frequency of dosing and duration of treatment may be determined by the skilled practitioner, and modified as needed to provide optimal IgE down-regulation, depending on nature of the allergen, the dose, frequency, and duration of the allergen exposure, and the standard clinical indices.

In one embodiment of the present invention, an IgE-suppressing compound may be administered in conjunction with one or more of the other small molecule inhibitors disclosed, in order to produce optimal down-regulation of the patient's IgE response. Further, it is envisioned that one or more of the compounds of the present invention may be administered in combination with other drugs already known or later discovered for treatment of the underlying cause as well as the acute symptoms of allergy or asthma. Such combination therapies envisioned within the scope of the present invention include mixing of one or more of the small molecule IgE-inhibitors together with one or more additional ingredients, known to be effective in reducing at least one symptom of the disease condition. In a variation, the small molecule IgE-inhibitors herein disclosed may be administered separately from the additional drugs, but during the same course of the disease condition, wherein both the IgE-inhibitor(s) and the palliative compounds are administered in accordance with their independent effective treatment regimens.

As an anti-proliferative therapy, the appropriate dose of the benzimidazole compounds disclosed herein may be determined by one skilled in the art. Pharmacologists and oncologists can readily determine the appropriate dose required for each individual patient without undue experimentation, based upon standard treatment techniques used for other anti-proliferation and chemotherapeutic agents.

Initially, suitable dosages of the anti-proliferation benzimidazole compounds will generally range from about 0.001 mg to about 300 mg per kg body weight per day in divided doses, more preferably, between about 0.01 mg and 100 mg per kg body weight per day in divided doses. Most preferably, to exert anticancer effects, the dose will range from about 1 mg to 100 mg per kg body weight per day. The compounds are preferably administered systemically as pharmaceutical formulations appropriate to such routes as oral, aerosol, intravenous, subcutaneously, or by any other route which may be effective in providing systemic dosing of the active compound.

Ideally one or more benzimidazole compounds of the present invention should be administered to achieve peak plasma concentrations of the active agent, as determined by one of skill in the art. To achieve adequate plasma levels, the pharmaceutical formulation may be injected intravenously in an appropriate solution, such as a saline solution or administered as a bolus of the active ingredient.

The treatment regimen used in accordance with several embodiments of the current invention preferably involves periodic administration. Moreover, as with other chemotherapeutic agents, long-term therapy may be indicated. Weekly, daily or twice daily administration for a period of one to three years may be required for some patients. Thus, in a preferred embodiment, the compound is administered for at least six months at regular periodic intervals. However, the treatment regimen, including frequency of dosing and duration of treatment may be determined by the skilled practitioner, and modified as needed to provide optimal anti-proliferation effects, depending on nature of the disease, the extent of abnormal cell growth, the type of cancer, the tissues affected, and standard clinical indices.

One skilled in the art will understand that the ideal concentration of the anti-proliferation compounds in the formulation depends upon several pharmacokinetic parameters, such as, absorption, inactivation, metabolism and clearance rates of the drug as well as other known factors. One skilled in the art will also appreciate that the concentration will vary with the severity of the condition to be treated. Other factors which may affect the treatment dose include, tumor location, age and gender of the patient, other illnesses, prior exposure to other drugs, and the like. One skilled in the art will appreciate that for any particular patient, specific treatment regimens will be evaluated and adjusted over time according to the individual patient's requirements and according to the professional judgment of the medical practitioner administering the treatment.

In one preferred embodiment, compounds of the current invention are orally administered. Preferably, oral formulations will include inert diluents or edible carriers. Oral dosages may be encapsulated in gelatin or formed into tablets. Oral administration may also be accomplished by using granules, grains or powders, syrups, suspensions, or solutions. One skilled in the art will understand that many acceptable oral compositions may be used in accordance with several embodiments of the present invention. For example, the active compound may be combined with standard excipients, adjuvants, lubricants, sweetening agents, enteric coatings, buffers, stabilizing agents and the like.

In one embodiment of the present invention, the active compound may be modified to include a targeting moiety that targets or concentrates the compound at the active site. Targeting moieties include, but are not limited to, antibodies, antibody fragments or derivatives, cytokines, and receptor ligands expressed on the cells to be treated.

In several embodiments, compounds of the current invention are administered in conjunction with other active agents, which either supplement or facilitate the action of the benzimidazole compound or cause other independent ameliorative effects. These additional active agents include, but are not limited to, antifungals, antivirals, antibiotics, anti-inflammatories, and anticancer agents. Protectants, which include carriers or agents which protect the active benzimidazole compound from rapid metabolism, degradation or elimination may also be used. Controlled release formulations can also be used in accordance with several embodiments of the current invention.

In one embodiment of the present invention, one or more anti-proliferation compounds may be administered in conjunction with one or more other anti-cancer agents or treatments to produce optimal anti-proliferative effects. Anti-cancer agents include, but are not limited to, alkylating agents (lomustine, carmustine, streptozocin, mechlorethamine, melphalan, uracil nitrogen mustard, chlorambucil cyclophosphamide, iphosphamide, cisplatin, carboplatin mitomycin thiotepa dacarbazine procarbazine, hexamethyl melamine, triethylene melamine, busulfan, pipobroman, and mitotane); antimetabolites (methotrexate, trimetrexate pentostatin, cytarabine, ara-CMP, fludarabine phosphate, hydroxyurea, fluorouracil, floxuridine, chlorodeoxyadenosine, gemcitabine, thioguanine, and 6-mercaptopurine); DNA cutters (bleomycin); topoisomerase I poisons (topotecan irinotecan and camptothecin); topoisomerase II poisons (daunorubicin, doxorubicin, idarubicin, mitoxantrone, teniposide, and etoposide); DNA binders (dactinomycin, and mithramycin); and spindle poisons (vinblastine, vincristine, navelbine, paclitaxel, and docetaxel).

Further, it is envisioned that one or more of the compounds of the present invention can be administered in combination with other therapies, such as radiation, immunotherapy, gene therapy and/or surgery, in order to treat hyperproliferative diseases, including cancer. Such combination therapies envisioned within the scope of the present invention include mixing of one or more of the benzimidazole compounds together with one or more additional ingredients, known to be effective in reducing at least one symptom of the disease condition. In a variation, the benzimidazole compounds herein disclosed may be administered separately from the additional drugs, but during the same course of the disease condition, wherein both the benzimidazole compound and the palliative compounds are administered in accordance with their independent effective treatment regimens.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A compound or salt thereof having the formula:

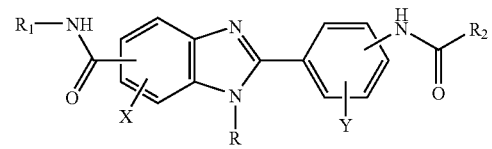

Genus I wherein R₁ is pyridyl;

wherein R₂ is selected from $C_3$–$C_9$ cycloalkyl, substituted $C_3$–$C_9$ cycloalkyl, phenyl, substituted phenyl, naphthyl and substituted naphthyl;

wherein the substituent on R₂ is selected from the group consisting of H, halogens, polyhalogens, alkoxy group, substituted alkoxy, alkyl, substituted alkyl, dialkylaminoalkyl, hydroxyalkyl, carbonyl, OH, OCH₃, COOH OCOR', COOR', COR', CN, CF₃, OCF₃, NO₂, NHCOR' and CONR' R';

wherein R' is selected from H, alkyl, substituted alkyl, $C_3$–$C_9$ cycloalkyl, substituted $C_3$–$C_9$ cycloalkyl, polycyclic aliphatics, substituted polycyclic aliphatics, aryl and substituted aryl, wherein X and Y are independently selected from the group consisting of H, halogens, alkoxy, substituted alkoxy, alkyl, substituted alkyl, dialkylaminoalkyl, hydroxyalkyl, OH, OCOR", OCH₃, COOH, CN, CF₃, OCF₃, NO₂, COOR", CHO and COR"; and wherein R" is a $C_1$–$C_8$ alkyl, wherein said $C_1$–$C_8$ alkyl is selected from the group consisting of a straight chain, branched or cyclic alkyl.

2. A method for treating an allergic reaction in a mammal wherein said reaction is caused by an increase in IgE levels comprising administering an IgE-suppressing amount of at least one compound or salt thereof of claim 1.

3. The method of claim 2 further comprising administering at least one additional ingredient which is active in reducing at least one symptom associated with said allergic reaction.

4. The method of claim 3, wherein said at least one additional ingredient is selected from the group consisting of a short-acting β₂-adrenergic agonist, a long-acting β₂-adrenergic agonist, an antihistamine, a phosphodiesterase inhibitor, an anticholinergic agent, a corticosteroid, an inflammatory mediator release inhibitor and a leukotriene receptor antagonist.

5. The method of claim 3, wherein said at least one additional ingredient is combined with said at least one IgE-suppressing compound in a pharmaceutically acceptable diluent and co-administered to the mammal.

6. The method of claim 5, wherein said at least one IgB-suppressing compound is administered at a dose of about 0.01 mg to about 100 mg per kg body weight per day.

7. The method of claim 6, wherein said dose is administered in divided doses at regular periodic intervals.

8. The method of claim 7, wherein said regular periodic intervals occur daily.

9. A method for treating asthma in a mammal comprising administering an IgE-suppressing amount of at least one compound or salt thereof of claim 1.

10. The method of claim 9 further comprising administering at least one additional ingredient which is active in reducing at least one symptom associated with said asthma.

11. The method of claim 10, wherein said additional ingredient is selected from the group consisting of a short-acting β₂-adrenergic agonist, a long-acting β₂-adrenergic agonist, an antihistamine, a phosphodiesterase inhibitor, an anticholinergic agent, a corticosteroid, an inflammatory mediator release inhibitor and a leukotriene receptor antagonist.

12. A compound or salt thereof selected from the group consisting of:

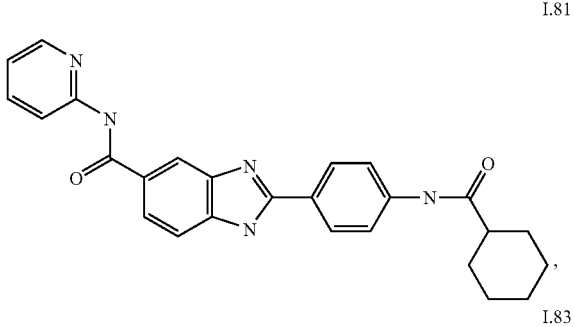

I.81

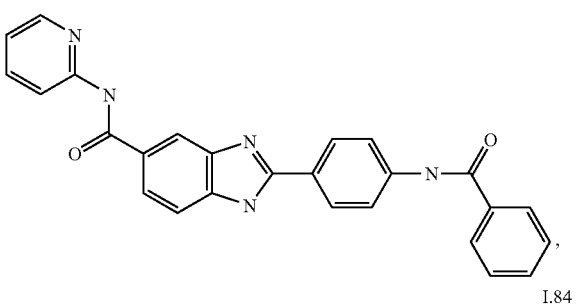

I.83

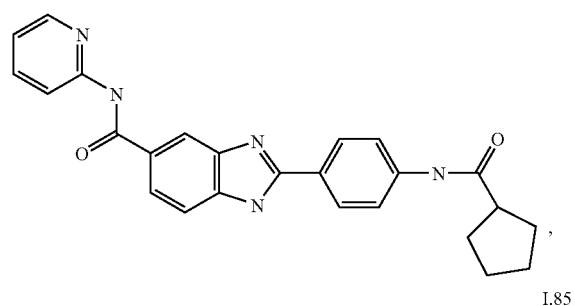

I.84

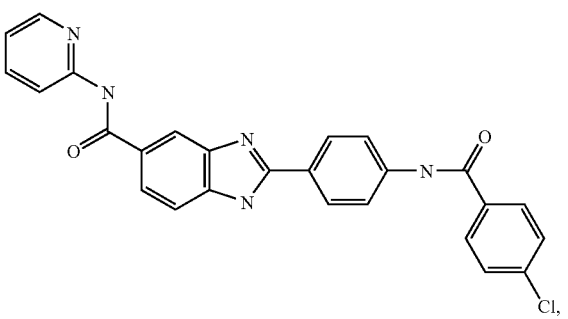

I.85

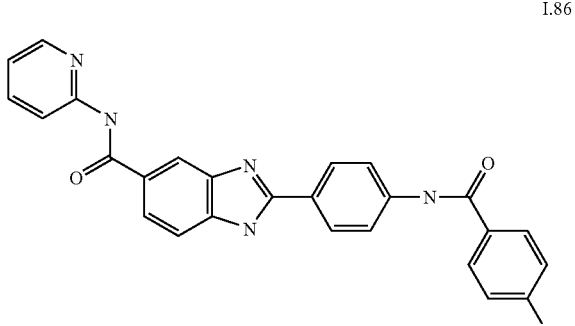

I.86

-continued
I.87
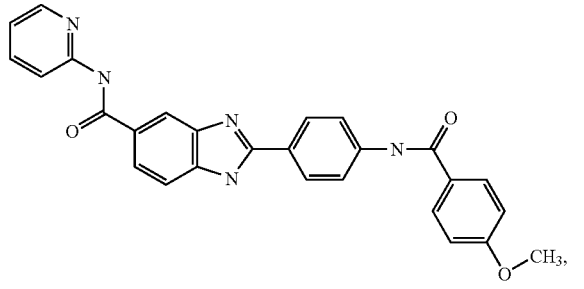
I.88
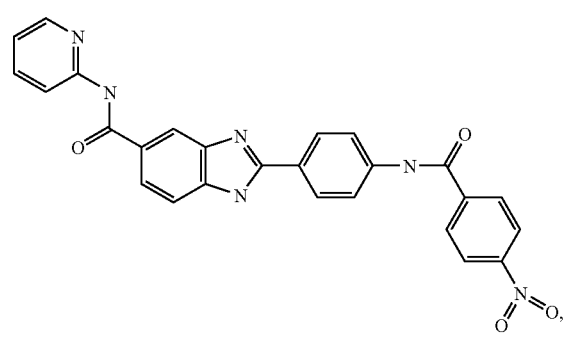
I.89
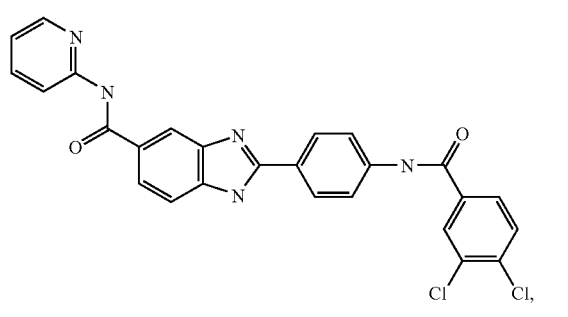
I.90
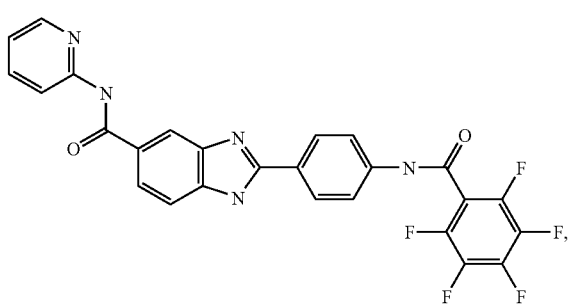
I.131
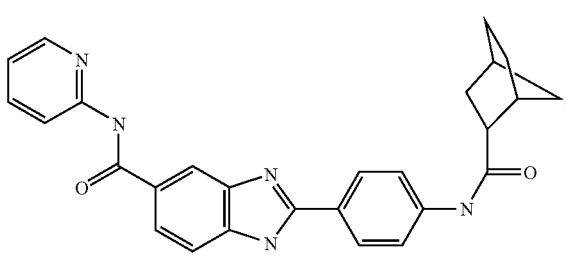
-continued
I.148
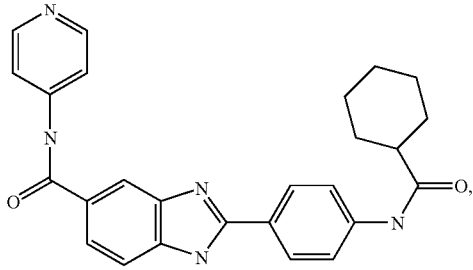
I.149
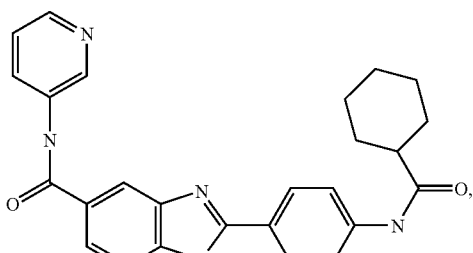
I.163
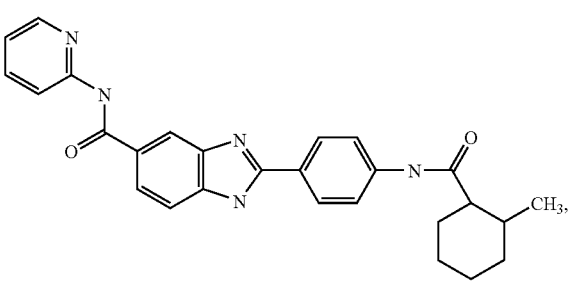
I.164
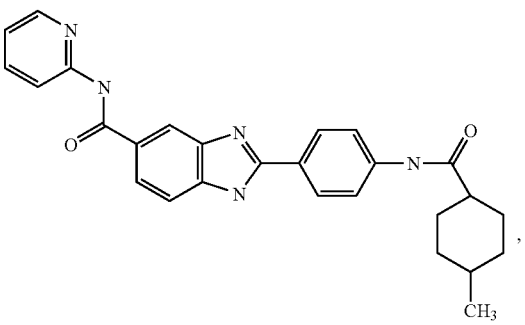
I.165
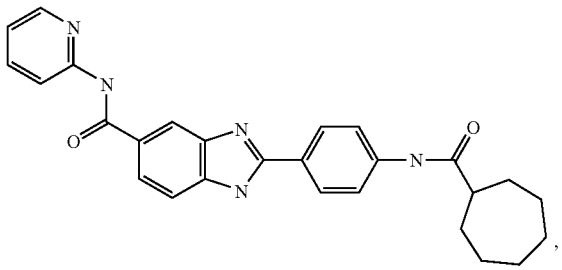

-continued

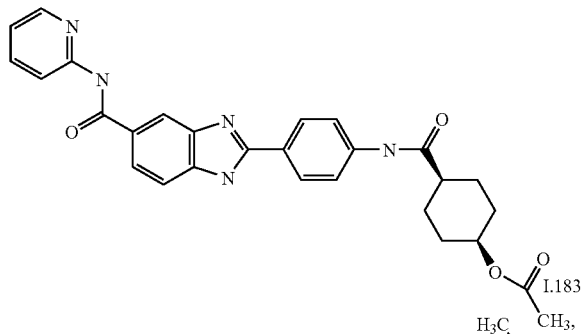
I.180

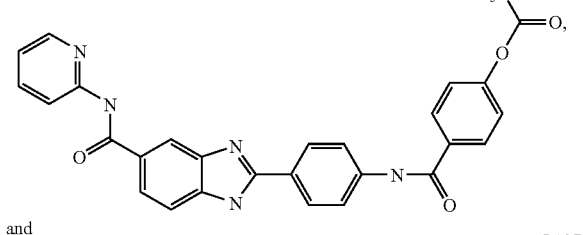
I.183 and

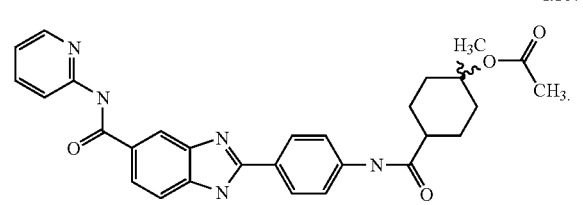
I.187

-continued

13. A method of preparing a compound or salt thereof of claim 1, wherein said method comprises:
  reacting a 3,4-diaminobenzoic acid with a 4-nitrobenzaldehyde to yield a first intermediate or salt thereof;
  aminating said first intermediate or salt thereof to yield a second intermediate or salt thereof;
  reducing said second intermediate or salt thereof to yield a third intermediate or salt thereof; and
  acylating said third intermediate or salt thereof to obtain said compound or salt thereof.

14. A pharmaceutical composition for treating asthma or an allergic reaction associated with an increase in IgE levels in a mammal comprising a compound or salt thereof of claim 1.

15. A method for inhibiting IgE response or lowering IgE levels in a mammal comprising administering an IgE-suppressing amount of at least one compound or salt thereof of claim 1.

16. The pharmaceutical composition of claim 14 further comprising at least one additional ingredient which is active in reducing at least one symptom associated with said allergic reaction.

* * * * *